United States Patent
Shi et al.

(10) Patent No.: US 11,352,345 B2
(45) Date of Patent: *Jun. 7, 2022

(54) CYCLOHEXYL ACID PYRAZOLE AZOLES AS LPA ANTAGONISTS

(71) Applicant: BRISTOL-MYERS SQUIBB COMPANY, Princeton, NJ (US)

(72) Inventors: Yan Shi, Flourtown, PA (US); Peter Tai Wah Cheng, Princeton, NJ (US); Hao Zhang, Belle Mead, NJ (US); Jun Li, Pittsburgh, PA (US); Tianan Fang, Newtown, PA (US); James R. Corte, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/954,320

(22) PCT Filed: Dec. 18, 2018

(86) PCT No.: PCT/US2018/066136
§ 371 (c)(1),
(2) Date: Jun. 16, 2020

(87) PCT Pub. No.: WO2019/126103
PCT Pub. Date: Jun. 27, 2019

(65) Prior Publication Data
US 2021/0078982 A1    Mar. 18, 2021

Related U.S. Application Data

(60) Provisional application No. 62/607,391, filed on Dec. 19, 2017.

(51) Int. Cl.
C07D 403/14 (2006.01)
C07D 413/14 (2006.01)
C07D 417/14 (2006.01)

(52) U.S. Cl.
CPC ......... *C07D 403/14* (2013.01); *C07D 413/14* (2013.01); *C07D 417/14* (2013.01)

(58) Field of Classification Search
CPC ..................... C07D 401/14; C07D 403/14
See application file for complete search history.

(56) References Cited

U.S. PATENT DOCUMENTS

| | | |
|---|---|---|
| 10,071,078 B2 | 9/2018 | Cheng et al. |
| 10,576,062 B2 | 5/2020 | Cheng et al. |
| 10,662,172 B2 | 5/2020 | Shi et al. |
| 2005/0070589 A1 | 3/2005 | Ngu et al. |
| 2014/0031353 A1 | 1/2014 | An et al. |
| 2014/0329871 A1 | 11/2014 | Mishira et al. |
| 2017/0360759 A1 | 12/2017 | Cheng et al. |
| 2020/0138789 A1 | 5/2020 | Cheng et al. |
| 2020/0148665 A1 | 5/2020 | Shi et al. |

FOREIGN PATENT DOCUMENTS

| | | |
|---|---|---|
| WO | WO2002062389 A1 | 8/2002 |
| WO | WO2011017350 A2 | 2/2011 |
| WO | WO2011041461 A2 | 4/2011 |
| WO | WO2011041694 A2 | 4/2011 |
| WO | WO2012078593 A2 | 6/2012 |
| WO | WO2012138648 A1 | 10/2012 |
| WO | WO2013070879 A1 | 5/2013 |
| WO | WO2013189864 A1 | 12/2013 |
| WO | WO2013189865 A1 | 12/2013 |
| WO | WO2014145873 A2 | 9/2014 |
| WO | WO2016044556 A2 | 3/2016 |
| WO | WO2017/223016 A1 | 12/2017 |

OTHER PUBLICATIONS

Harper et al. Molecular Cancer Research, p. 1601-1613. (Year: 2018).*
U.S. Appl. No. 16/772,825, filed Jun. 15, 2020, Shi et al.
U.S. Appl. No. 16/772,842, filed Jun. 15, 2020, Shi et al.
U.S. Appl. No. 16/954,221, filed Jun. 16, 2020, Cheng et al.
U.S. Appl. No. 16/954,310, filed Jun. 16, 2020, Shi et al.
U.S. Appl. No. 16/954,325, filed Jun. 16, 2020, Shi et al.
U.S. Appl. No. 16/954,546, filed Jun. 17, 2020, Cheng et al.
U.S. Appl. No. 16/954,550, filed Jun. 17, 2020, Cheng et al.
U.S. Appl. No. 16/954,552, filed Jun. 17, 2020, Shi et al.
U.S. Appl. No. 16/954,556, filed Jun. 17, 2020, Cheng et al.
Amishima, et al., "Expression of Epidermal Growth Factor and Epidermal Growth Factor Receptor Immunoreactivity in the Asthmatic Human Airway", Am. J. Respir. Critical Care Medicine, vol. 157, pp. 1907-1912 (1998).

(Continued)

Primary Examiner — Erich A Leeser
(74) Attorney, Agent, or Firm — Jing G. Sun

(57) ABSTRACT

The present invention provides compounds of Formula (I) or a stereoisomer, tautomer, or pharmaceutically acceptable salt or solvate thereof, wherein all the variables are as defined herein. These compounds are selective LPA receptor inhibitors.

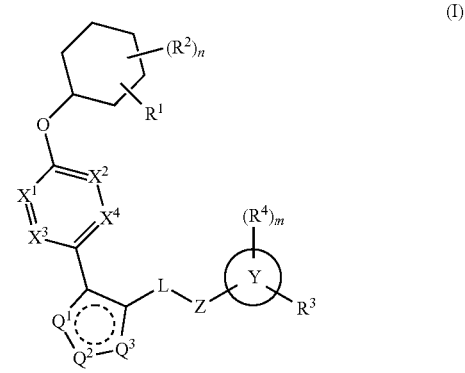

(I)

3 Claims, No Drawings

(56) References Cited

OTHER PUBLICATIONS

Boucharaba, et al., "Platelet-derived lysophosphatidic acid supports the progression of osteolytic bone metastases in breast cancer", J. Clin. Invest., vol. 114(12), pp. 1714-1725 (2004).
Boucharaba, et al., "The type 1 lysophosphatidic acid receptor is a target for therapy in bone metastases", PNAS, vol. 103(25), pp. 9643-9648 (2006).
Chen, et al., "Specific receptor subtype mediation of LPA-induced dual effects incardiac fibroblasts", FEBS Letters, vol. 580(19), pp. 4737-4745 (2006).
Choi, et al., "Biological roles of lysophospholipid receptors revealedby genetic null mice: An update", Biochemica et Biophysica Acta, vol. 1781, pp. 531-539 (2008).
Contos, et al., "Lysophosphatidic Acid Receptors", Mol. Pharmacology, vol. 58(6), pp. 1188-1196 (2000).
Ediger, et al., "Transcription factor activation and mitogenic synergism in airway smooth muscle cells", Eur Respir Journal, vol. 21, pp. 759-769 (2003).
Gardell, et al., "Emerging medicinal roles for lysophospholipid signaling", Trends in Molecular Medicine, vol. 12(2), pp. 65-75 (2006).
Geoetzl, et al., "Lysophosphatidic Acid and Sphingosine 1-PhosphateProtection of T Cells from Apoptosis in Association with Suppression of Bax1", Journal of Immunology, vol. 162, pp. 2049-2056 (1999).
Guo, et al., "Mitogenic Signaling in Androgen Sensitive and Insensitive Prostate Cancer Cell Lines", Journal of Urology, vol. 163(3), pp. 1027-1032 (2000).
Hashimoto, et al., "Lysophosphatidic Acid (LPA) Induces Plasma Exudation and Histamine Release in Mice via LPA Receptors", J Pharmacol Science, vol. 100, pp. 82-87 (2006).
Holtsberg, et al., "Lysophosphatidic Acid Induces Necrosis and Apoptosis in Hippocampal Neurons", J. Neurochemistry, vol. 70, pp. 66-76 (1998).
Imamura, "Induction of In Vitro Tumor cell invasion of cellular monolayers by lysophosphatidic acid or phospholupase D", Biochem Biophys Res Commun., vol. 193(2), pp. 497-503 (1993).
Inoue, et al., "Initiation of neuropathic pain require lysophosphatidic acid receptor signaling" Nature Medicine, vol. 10, pp. 712-718 (2004).
Inoue, et al., "Lysophosphatidic acid and mesangial cells: implications for renal diseases", Clinical Science, vol. 96(4), pp. 431-436 (1999).
Ishii, et al., "Lysophospholipid Receptors:Signaling and Biology", Annu Rev Biochemistry, vol. 73, pp. 321-354 (2004).
Kantarci, et al., "Epithelial and connective tissue cell CTGF/CCN2 expression in gingival fibrosis", J Pathol., vol. 210, pp. 59-66 (2006).
Koh, et al., "Lysophosphatidic Acid Is a Major Serum Noncytokine Survival Factor for Murine Macrophages Which Acts via the Phosphatidylinositol 3-Kinase Signaling Pathway", J Clin Invest., vol. 102, pp. 716-727 (1998).
Kropp, et al., "Characterization of Cultured Bladder Smooth Muscle Cells: Assessment of in Vitro Contractility", Journal of Urology, vol. 162(5), pp. 1779-1784 (1999).
Kuroda, et al., "Phospholipid Concentration in Lung Lavage Fluid as Biomarker for Pulmonary Fibrosis", Inhalation Toxicology, vol. 18(5), pp. 389-393 (2006).
Lin, et al., "Lysophosphatidic acid regulates inflammation-related genes in human endothelial cells through LPA1 and LPA3", Biochem Biophys Res Communication, vol. 363(4), pp. 1001-1008, (2007).
Maguire, et al., "Regulation of vascular reactivity by established and emerging GPCRs", Trends in Pharmacological Sciences, vol. 26(9), pp. 448-454 (2005).
Mills, et al., "The Emerging Role of Lysophosphatidic Acid in Cancer", Nat Rev Cancer, vol. 3, pp. 582-591 (2003).
Moolenaar, "Lysophosphatidic acid signalling", Curr. Opin. Cell Biology, vol. 7, pp. 203-210 (1995).
Mototani, et al., "A functional SNP in EDG2 increases susceptibilityto knee osteoarthritis in Japanese", Hum. Mol. Genetics, vol. 17(12), pp. 1790-1797 (2008).
Munger, et al., "The Integrin avb6 Binds and Activates Latent TGFb1:A Mechanism for Regulating Pulmonary Inflammation and Fibrosis", Cell, vol. 96, pp. 319-328 (1999).
Murph, et al., "Sharpening the edges of understanding the structure/function of the LPA1 receptor: Expression in cancer and mechanisms of regulation", Biochimica et Biophysica Acta, vol. 1781, pp. 547-557 (2008).
Nakagawa, et al. "Molecular Liver Cancer Prevention in Cirrhosis byOrgan Transcriptome Analysis and Lysophosphatidic Acid Pathway Inhibition" Cancer Cell, vol. 30, pp. 879-890 (2016).
Osborne, et al., "Lipid Receptors in Cardiovascular Development", Annual Rev. Physiol., vol. 65, pp. 23-43 (2003).
Palmer, et al. "Randomized, Double-Blind, Placebo Controlled, Phase 2 Trial of BMS-986020, a Lysophosphatidic Acid Receptor Antagonist for the Treatment of Idiopathic Pulmonary Fibrosis" Chest, vol. 154, pp. 1061-1069 (2018).
Pradere, et al "LPA1 Receptor Activation Promotes Renal Interstitial Fibrosis", J Am Soc Nephrol, vol. 18, pp. 3110-3118 (2007).
Pradere, et al., "Lysophosphatidic acid and renal fibrosis", Biochimica et Biophysica Acta, vol. 1781, pp. 582-587 (2008).
Rother, et al., "Subtype-Selective Antagonists of Lysophosphatidic Acid Receptors Inhibit Platelet Activation Triggered by the LipidCore of Atherosclerotic Plaques", Circulation, vol. 108, pp. 741-747 (2003).
Saunders, et al., "Identification of small-molecule inhibitors of autotaxin that inhibit melanoma cell migration and invasion", Mol Cancer Ther., vol. 7(10), pp. 3352-3362 (2008).
Siess, "Athero- and thrombogenic actions of lysophosphatidic acid and sphingosine-1-phosphate", Biochimica et Biophysica Acta, vol. 1582, pp. 204-215 (2002).
Simon, et al., "Lysophosphatidic Acid 1 Receptor-dependent Down-regulation of Peroxisome Proliferator-activated Receptor $\gamma 2$*" J.Biol. Chemistry, vol. 280(15) pp. 14656-14662 (2005).
Smalheiser, "Acute Neurite Retraction Elicited by Diverse Agents Is Prevented by Genistein, a Tyrosine Kinase Inhibitor", J. Neurochemistry, vol. 61(1), pp. 340-343 (1993).
Sutphen, et al., "Lysophospholipids Are Potential Biomarkers of Ovarian Cancer", Cancer Epidemiol. Biomarkers Prev. 13, pp. 1185-1191 (2004).
Tager, et al., The lysophosphatidic acid receptor LPA1 links pulmonaryfibrosis to lung injury by mediating fibroblast recruitmentand vascular leak, Nature Medicine, vol. 14, pp. 45-54 (2008).
Watanabe, et al., "Both Plasma Lysophosphatidic Acid and Serum Autotaxin Levels are Increased in Chronic Hepatitis C", J Clinical Gastroenterology, vol. 41, pp. 616-623 (2007).
Watanabe, et al., "Plasma lysophosphatidic acid level and serum autotaxin activity are increased in liver injury in rats in relation to its severity", Life Science, vol. 81, pp. 1009-1015 (2007).
Wiedmaier, et al., "Bacteria induce CTGF and CYR61 expression in epithelial cells ina lysophosphatidic acid receptor-dependent manner", Int J Med Microbiology, vol. 298(3-4), pp. 231-243 (2008).
Xu, et al., "Lysophosphatidic Acid Induces $\alpha v \beta 6$ Integrin-Mediated TGF-$\beta$ Activation via the LPA2 Receptor and the Small G Protein G$\alpha$q", Am J Pathology, vol. 174(4), pp. 1264-1279 (2009).
Yamada, et al., "Lysophosphatidic Acid (LPA) in Malignant Ascites Stimulates Motility of Human Pancreatic Cancer Cells through LPA1*", J Biol Chemistry, vol. 279, pp. 6596-6605 (2004).
Yamada, et al., "Lysophosphatidic acid stimulates the proliferation and motility of malignant pleural mesothelioma cells through lysophosphatidic acid receptors, LPA1 and LPA2", Cancer Science, vol. 99(8), pp. 1603-1610 (2008).
Yasuda, et al., "Phospholipid Analysis of Alveolar Macrophagesand Bronchoalveolar Lavage Fluid Following Bleomycin Administration to Rabbits", Lung, vol. 172, pp. 91-102 (1994).
Zhao, et al., "Regulation of Lysophosphatidic Acid Receptor Expression and Function in Human Synoviocytes: Implications for Rheumatoid Arthritis" Mol. Pharmacology, vol. 73(2), pp. 587-600 (2008).

* cited by examiner

CYCLOHEXYL ACID PYRAZOLE AZOLES AS LPA ANTAGONISTS

CROSS-REFERENCE TO RELATED APPLICATIONS

This application is a 371 of International Application No. PCT/US2018/066136 filed on Dec. 18, 2018, which claims the priority benefit of U.S. Provisional Application 62/607,391, filed Dec. 19, 2017; each of which is incorporated herein by reference in its entirety.

FIELD OF THE INVENTION

The present invention relates to novel substituted pyrazole compounds, compositions containing them, and methods of using them, for example, for the treatment of disorders associated with one or more of the lysophosphatidic acid (LPA) receptors.

BACKGROUND OF THE INVENTION

Lysophospholipids are membrane-derived bioactive lipid mediators, of which one of the most medically important is lysophosphatidic acid (LPA). LPA is not a single molecular entity but a collection of endogenous structural variants with fatty acids of varied lengths and degrees of saturation (Fujiwara et al., *J Biol. Chem.*, 2005, 280, 35038-35050). The structural backbone of the LPAs is derived from glycerol-based phospholipids such as phosphatidylcholine (PC) or phosphatidic acid (PA).

The LPAs are bioactive lipids (signaling lipids) that regulate various cellular signaling pathways by binding to the same class of 7-transmembrane domain G protein-coupled (GPCR) receptors (Chun, J., Hla, T., Spiegel, S., Moolenaar, W., Editors, *Lysophospholipid Receptors: Signaling and Biochemistry*, 2013, Wiley; ISBN: 978-0-470-56905-4 & Zhao, Y. et al, *Biochim. Biophys. Acta (BBA)-Mol. Cell Biol. Of Lipids*, 2013, 1831, 86-92). The currently known LPA receptors are designated as $LPA_1$, $LPA_2$, $LPA_3$, $LPA_4$, $LPA_5$ and $LPA_6$ (Choi, J. W., *Annu. Rev. Pharmacol. Toxicol.*, 2010, 50, 157-186; Kihara, Y., et al, *Br. J Pharmacol.*, 2014, 171, 3575-3594).

The LPAs have long been known as precursors of phospholipid biosynthesis in both eukaryotic and prokaryotic cells, but the LPAs have emerged only recently as signaling molecules that are rapidly produced and released by activated cells, notably platelets, to influence target cells by acting on specific cell-surface receptors (see, e.g., Moolenaar et al., *BioEssays*, 2004, 26, 870-881, and van Leewen et al., *Biochem. Soc. Trans.*, 2003, 31, 1209-1212). Besides being synthesized and processed to more complex phospholipids in the endoplasmic reticulum, LPAs can be generated through the hydrolysis of pre-existing phospholipids following cell activation; for example, the sn-2 position is commonly missing a fatty acid residue due to deacylation, leaving only the sn-1 hydroxyl esterified to a fatty acid. Moreover, a key enzyme in the production of LPA, autotaxin (lysoPLD/NPP2), may be the product of an oncogene, as many tumor types up-regulate autotaxin (Brindley, D., *J. Cell Biochem.* 2004, 92, 900-12). The concentrations of LPAs in human plasma & serum as well as human bronchoalveolar lavage fluid (BALF) have been reported, including determinations made using sensitive and specific LC/MS & LC/MS/MS procedures (Baker et al. *Anal. Biochem.*, 2001, 292, 287-295; Onorato et al., *J. Lipid Res.*, 2014, 55, 1784-1796).

LPA influences a wide range of biological responses, ranging from induction of cell proliferation, stimulation of cell migration and neurite retraction, gap junction closure, and even slime mold chemotaxis (Goetzl, et al., *Scientfic World J.*, 2002, 2, 324-338; Chun, J., la, T., Spiegel, S., Moolenaar, W., Editors, *Lysophospholipid Receptors: Signaling and Biochemistry*, 2013, Wiley; ISBN: 978-0-470-56905-4). The body of knowledge about the biology of LPA continues to grow as more and more cellular systems are tested for LPA responsiveness. For instance, it is now known that, in addition to stimulating cell growth and proliferation, LPAs promote cellular tension and cell-surface fibronectin binding, which are important events in wound repair and regeneration (Moolenaar et al., *BioEssays*, 2004, 26, 870-881). Recently, anti-apoptotic activity has also been ascribed to LPA, and it has recently been reported that PPARγ is a receptor/target for LPA (Simon et al., *J. Biol. Chem.*, 2005, 280, 14656-14662).

Fibrosis is the result of an uncontrolled tissue healing process leading to excessive accumulation and insufficient resorption of extracellular matrix (ECM) which ultimately results in end-organ failure (Rockey, D. C., et al., *New Engl. J. Med*, 2015, 372, 1138-1149). The $LPA_1$ receptor has been reported to be over-expressed in idiopathic pulmonary fibrosis (IPF) patients. $LPA_1$ receptor knockout mice were protected from bleomycin-induced lung fibrosis (Tager et al., *Nature Med*, 2008, 14, 45-54). The $LPA_1$ antagonist BMS-986020 was shown to significantly reduce the rate of FVC (forced vital capacity) decline in a 26-week clinical trial in IPF patients (Palmer et al., *Chest*, 2018, 154, 1061-1069). LPA pathway inhibitors (e.g. an $LPA_1$ antagonist) were shown to be chemopreventive anti-fibrotic agents in the treatment of hepatocellular carcinoma in a rat model (Nakagawa et al., Cancer Cell, 2016, 30, 879-890).

Thus, antagonizing the $LPA_1$ receptor may be useful for the treatment of fibrosis such as pulmonary fibrosis, hepatic fibrosis, renal fibrosis, arterial fibrosis and systemic sclerosis, and thus the diseases that result from fibrosis (pulmonary fibrosis-Idiopathic Pulmonary Fibrosis [IPF], hepatic fibrosis-Non-alcoholic Steatohepatitis [NASH], renal fibrosis-diabetic nephropathy, systemic sclerosis-scleroderma, etc.).

SUMMARY OF THE INVENTION

The present invention provides novel substituted triazole compounds including stereoisomers, tautomers, and pharmaceutically acceptable salts or solvates thereof, which are useful as antagonists against one or more of the lysophosphatidic acid (LPA) receptors, especially the $LPA_1$ receptor.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts or solvates thereof.

The compounds of the invention may be used in the treatment of conditions in which LPA plays a role.

The compounds of the present invention may be used in therapy.

The compounds of the present invention may be used for the manufacture of a medicament for the treatment of a condition in which inhibition of the physiological activity of LPA is useful, such as diseases in which an LPA receptor participates, is involved in the etiology or pathology of the disease, or is otherwise associated with at least one symptom of the disease.

In another aspect, the present invention is directed to a method of treating fibrosis of organs (liver, kidney, lung, heart and the like as well as skin), liver diseases (acute hepatitis, chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease [cancer (solid tumor, solid tumor metastasis, vascular fibroma, myeloma, multiple myeloma, Kaposi's sarcoma, leukemia, chronic lymphocytic leukemia (CLL) and the like) and invasive metastasis of cancer cell, and the like], inflammatory disease (psoriasis, nephropathy, pneumonia and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract, and the like), inflammatory disease of lower urinary tract, dysuria, frequent urination, and the like), pancreas disease, abnormal angiogenesis-associated disease (arterial obstruction and the like), scleroderma, brain-associated disease (cerebral infarction, cerebral hemorrhage, and the like), neuropathic pain, peripheral neuropathy, and the like, ocular disease (age-related macular degeneration (AMD), diabetic retinopathy, proliferative vitreoretinopathy (PVR), cicatricial pemphigoid, glaucoma filtration surgery scarring, and the like).

In another aspect, the present invention is directed to a method of treating diseases, disorders, or conditions in which activation of at least one LPA receptor by LPA contributes to the symptomology or progression of the disease, disorder or condition. These diseases, disorders, or conditions may arise from one or more of a genetic, iatrogenic, immunological, infectious, metabolic, oncological, toxic, surgical, and/or traumatic etiology.

In another aspect, the present invention is directed to a method of treating renal fibrosis, pulmonary fibrosis, hepatic fibrosis, arterial fibrosis and systemic sclerosis comprising administering to a patient in need of such treatment a compound of the present invention as described above.

In one aspect, the present invention provides methods, compounds, pharmaceutical compositions, and medicaments described herein that comprise antagonists of LPA receptors, especially antagonists of $LPA_1$.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

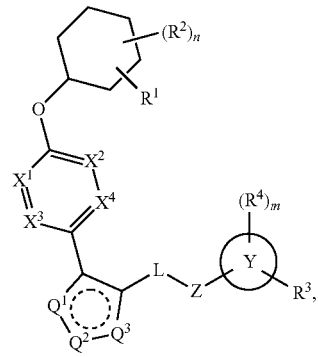

or a stereoisomer, tautomer, or pharmaceutically acceptable salt or solvate thereof, wherein $X^1$, $X^2$, $X^3$, and $X^4$ are each independently $CR^6$ or N; provided that no more than two of $X^1$, $X^2$, $X^3$, or $X^4$ are N;

$Q^2$ is N or $NR^{5b}$;

one of $Q^1$ and $Q^3$ is $CR^{5a}$, and the other is N or $NR^{5b}$;

the dashed circle denotes optional bonds forming an aromatic ring;

L is a covalent bond or $C_{1-4}$ alkylene substituted with 0 to 4 $R^7$;

Z is $CHR^{8a}$, $NR^{8b}$ or O;

the Y ring is a 5-membered heteroaryl or 5-membered heterocyclyl, each of which independently contains one nitrogen atom and at least one other heteroatom selected from nitrogen, oxygen, and sulfur;

$R^1$ is $(-CH_2)_a R^9$;

a is an integer of 0 or 1;

$R^2$ is each independently halo, cyano, hydroxyl, amino, $C_{1-6}$ alkyl, $C_{3-6}$ cycloalkyl, 4 to 6-membered heterocyclyl, alkylamino, haloalkyl, hydroxyalkyl, aminoalkyl, alkoxy, alkoxyalkyl, haloalkoxyalkyl, or haloalkoxy;

n is an integer of 0, 1, or 2;

$R^3$ is halo, cyano, hydroxyl, amino, oxo, $-OR^a$, $-SR^a$, $=S$, $-NR^cR^c$, $=NH$, $=N-OH$, $=NR^a$, $=N-OR^a$, $-NO_2$, $-S(O)_2R^a$, $-S(O)_2NHR^b$, $-S(O)_2NR^cR^c$, $-S(O)_2OR^b$, $-OS(O)_2R^b$, $-OS(O)_2OR^b$, $-P(O)(OR^b)(OR^b)$, $-C(O)R^b$, $-C(NR^b)R^b$, $-C(O)OR^b$, $-C(O)NR^cR^c$, $-C(NR^b)NR^cR^c$, $-OC(O)R^b$, $-NR^bC(O)R^b$, $-OC(O)OR^b$, $-NR^bC(O)OR^b$, $-OC(O)NR^cR^c$, $-NR^bC(O)NR^cR^c$, $-NR^bC(NR^b)R^b$, $-NR^bC(NR^b)NR^cR^c$, $C_{1-6}$ alkyl, $C_{1-6}$ deuterated alkyl, $C_{1-6}$ heteroalkyl, 6- to 10-membered aryl, arylalkyl, 5- to 10-membered heteroaryl, heteroarylalkyl, 3- to 8-membered carbocyclyl, carbocyclylalkyl, 4- to 8-membered heterocyclyl, or heterocyclylalkyl; wherein the alkyl, heteroalkyl, aryl, heteroaryl, carbocyclyl, heterocyclyl, and $R^a$, by themselves or as part of another group, are each independently substituted with 0 to 5 $R^d$;

$R^a$ is selected from $C_{1-6}$ alkyl, $C_{1-6}$ deuterated alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

$R^b$ is each independently hydrogen or $R^a$;

$R^c$ is each independently $R^b$; or alternatively, two $R^c$, taken together with the nitrogen atom to which they are attached, form a 4- to 7-membered heterocyclyl;

$R^d$ is each independently selected from $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —OR$^a$, —SR$^a$, =S, —NR$^c$R$^c$, =NH, =N—OH, =NR$^a$, =N—OR$^a$, —NO$_2$, —S(O)$_2$R$^a$, —S(O)$_2$NHR$^b$, —S(O)$_2$NR$^c$R$^c$, —S(O)$_2$OR$^b$, —OS(O)$_2$R$^b$, —OS(O)$_2$OR$^b$, —P(O)(OR$^b$)(OR$^b$), —C(O)R$^b$, —C(NR$^b$)R$^b$, —C(O)OR$^b$, —C(O)NR$^c$R$^c$, —C(NR$^b$)NR$^c$R$^c$, —OC(O)R$^b$, —NR$^b$C(O)R$^b$, —OC(O)OR$^b$, —NR$^b$C(O)OR$^b$, —NR$^b$C(O)NR$^c$R$^c$, —NR$^b$C(NR)R$^b$, and —NR$^b$C(NR$^b$)NR$^c$R$^c$; or alternatively one or two R$^d$ on alkyl, heteroalkyl, aryl, heteroaryl, carbocyclyl, or heterocyclyl, taken together with the atoms to which the R$^d$ is attached, form a cyclic or bridge moiety;

R$^4$ is each independently halo, hydroxyl, cyano, C$_{1-4}$ alkyl, C$_{1-4}$ haloalkyl, C$_{2-6}$ alkoxyalkyl, C$_{1-4}$ alkoxy, oxo (=O), or imino (=NH);

m is an integer of 0, 1, or 2;

R$^{5a}$ and R$^6$ are each independently hydrogen, halo, cyano, hydroxyl, amino, C$_{1-6}$ alkyl, alkylamino, haloalkyl, hydroxyalkyl, aminoalkyl, alkoxyalkyl, haloalkoxyalkyl, alkoxy, or haloalkoxy;

R$^{5b}$ is hydrogen, C$_{1-6}$ alkyl, alkylamino, haloalkyl, hydroxyalkyl, aminoallkyl, alkoxyalkyl, haloalkoxyalkyl, alkoxy, or haloalkoxy;

R$^7$ is halo, oxo, cyano, hydroxyl, amino, C$_{1-6}$ alkyl, C$_{3-6}$ cycloalkyl, 4 to 6-membered heterocyclyl, alkylamino, haloalkyl, hydroxyalkyl, aminoalkyl, alkoxyalkyl, haloalkoxyalkyl, alkoxy, or haloalkoxy;

R$^{8a}$ is hydrogen, halo, cyano, or C$_{1-4}$ alkyl;

R$^{8b}$ is hydrogen or C$_{1-4}$ alkyl;

R$^9$ is selected from —CN, —C(O)OR$^{10}$, —C(O)NR$^{11a}$R$^{11b}$,

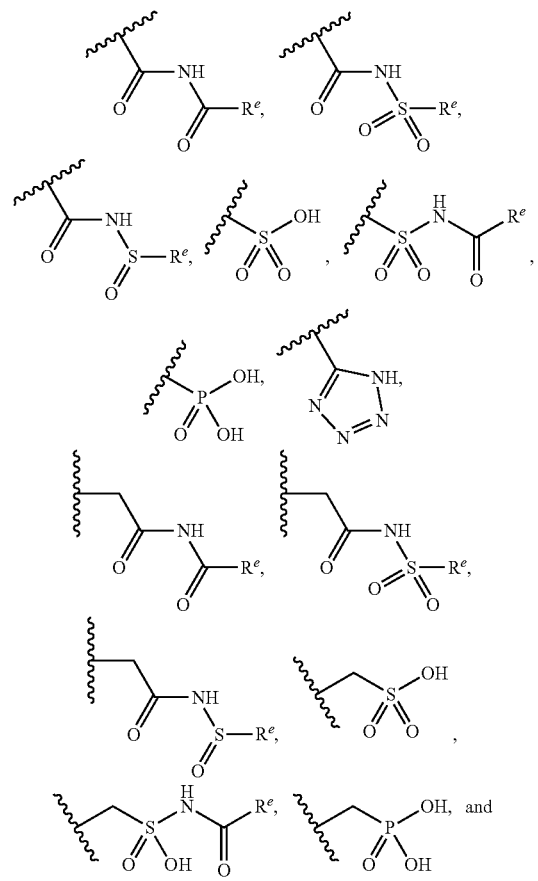

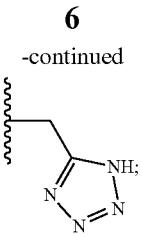

R$^e$ is C$_{1-6}$ alkyl, haloalkyl, hydroxyalkyl, aminoalkyl, alkoxyalkyl, or haloalkoxyalkyl;

R$^{10}$ is hydrogen or C$_{1-10}$ alkyl; and

R$^{11a}$ and R$^{11b}$ are each independently hydrogen, C$_{1-6}$ alkyl, C$_{3-6}$ cycloalkyl, 4 to 6-membered heterocyclyl, alkylamino, haloalkyl, hydroxyalkyl, aminoalkyl, alkoxyalkyl, haloalkoxyalkyl, alkoxy, or haloalkoxy.

In one embodiment of Formula (I), X$^2$ is CR$^6$, where R$^6$ is hydrogen or C$_{1-4}$ alkyl (e.g., methyl).

In any one of the preceding embodiments of Formula (I), R$^{5b}$ is hydrogen or C$_{1-6}$ alkyl.

In another embodiment, R$^{5a}$ is hydrogen.

In any one of the preceding embodiments of Formula (I), the

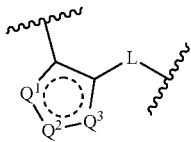

moiety is

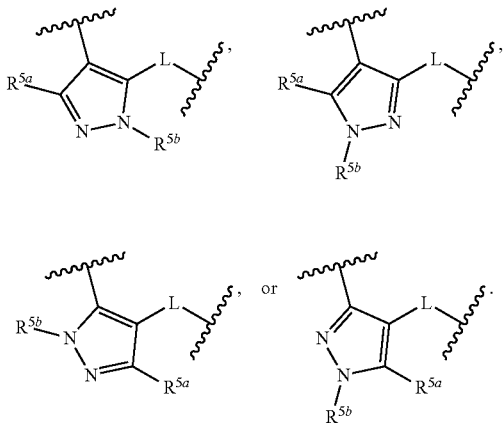

In any one of the preceding embodiments of Formula (I), the

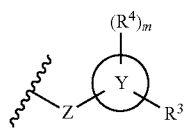

moiety is

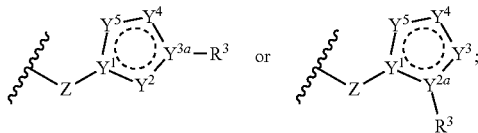

$Y^1$, $Y^{2a}$, and $Y^{3a}$ are each independently selected from C or N; and the dashed circle denotes optional bonds; wherein the 5-member ring formed by ($Y^1$, $Y^2$, $Y^{3a}$, $Y^4$, and $Y^5$) or ($Y^1$, $Y^2$, $Y^3$, $Y^4$, and $Y^5$) can be either aromatic or nonaromatic;

$Y^2$, $Y^3$, $Y^4$, and $Y^5$ are each independently selected from C, $CR^{4a}$, N, $NR^{4b}$, S, or O; with the provisos that (1) at least one of ($Y^1$, $Y^2$, $Y^{3a}$, $Y^4$, and $Y^5$) or at least one of ($Y^1$, $Y^{2a}$, $Y^3$, $Y^4$, and $Y^5$) is N or $NR^{4b}$, and (2) at least one of ($Y^1$, $Y^2$, $Y^{3a}$, $Y^4$, and $Y^5$) or at least one of ($Y^1$, $Y^{2a}$, $Y^3$, $Y^4$, and $Y^5$) is C or $CR^{4a}$;

$R^{4a}$ is each independently hydrogen, halo, oxo, imino, $C_{1-6}$ alkyl, $C_{1-4}$ haloalkyl, $C_{2-6}$ alkoxyalkyl, $C_{1-4}$ alkoxy; and $R^{4b}$ is each independently hydrogen or $C_{1-4}$ alkyl.

In any one of the preceding embodiments of Formula (I), $R^3$ is halo, cyano, hydroxyl, amino, $-OR^a$, $-SR^a$, $-NR^cR^c$, $C_{1-6}$ alkyl, $C_{1-6}$ heteroalkyl, 6- to 10-membered aryl, arylalkyl, 5- to 10-membered heteroaryl, heteroarylalkyl, 3- to 8-membered carbocyclyl, carbocyclylalkyl, 4- to 8-membered heterocyclyl, or heterocyclylalkyl; wherein the alkyl, heteroalkyl, aryl, heteroaryl, carbocyclyl, heterocyclyl, and $R^a$, by themselves or as part of another group, are each independently substituted with 0 to 5 $R^d$;

$R^a$ is selected from $C_{1-6}$ alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

$R^b$ is each independently hydrogen or $R^a$;

$R^c$ is each independently $R^b$; or alternatively, two $R^c$, taken together with the nitrogen atom to which they are attached, form a 4- to 7-membered heterocyclyl;

$R^d$ is each independently selected from $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, $-OR^a$, $-SR^a$, and $-NR^cR^c$; or alternatively one or two $R^d$ on alkyl, heteroalkyl, aryl, heteroaryl, carbocyclyl, or heterocyclyl, taken together with the atoms to which the $R^d$ is attached, form a cyclic or bridge moiety.

In any one of the preceding embodiments of Formula (I), the compound is represented by Formula (IIa) or (IIb):

(IIa)

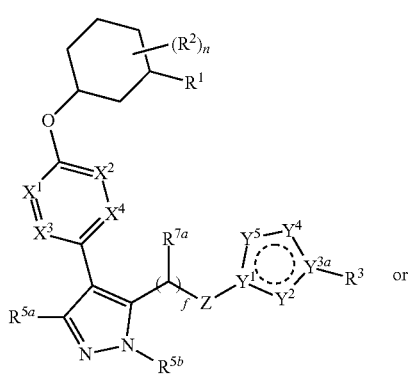

(IIb)

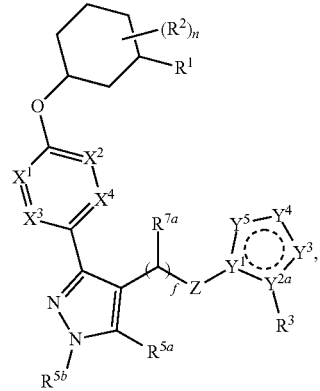

$Y^1$ and $Y^{3a}$ are each independently C or N;

$Y^2$, $Y^3$, $Y^4$, and $Y^5$ are each independently selected from C, $CR^{4a}$, N, $NR^{4b}$, S, or O; with the provisos that (1) at least one of ($Y^1$, $Y^2$, $Y^{3a}$, $Y^4$, and $Y^5$) or at least one of ($Y^1$, $Y^{2a}$, $Y^3$, $Y^4$, and $Y^5$) is N or $NR^{4b}$, and (2) at least one of ($Y^1$, $Y^2$, $Y^{3a}$, $Y^4$, and $Y^5$) or at least one of ($Y^1$, $Y^{2a}$, $Y^3$, $Y^4$, and $Y^5$) is C or $CR^{4a}$; and the dashed circle denotes optional bonds; wherein the 5-member ring formed by ($Y^1$, $Y^2$, $Y^{3a}$, $Y^4$, and $Y^5$) or ($Y^1$, $Y^{2a}$, $Y^3$, $Y^4$, and $Y^5$) can be either aromatic or nonaromatic;

$R^{4a}$ is each independently hydrogen, halo, $C_{1-4}$ alkyl, $C_{1-4}$ haloalkyl, $C_{2-6}$ alkoxyalkyl, $C_{1-4}$ alkoxy, oxo, or imino;

$R^{4b}$ is each independently hydrogen or $C_{1-4}$ alkyl;

$R^{7a}$ is each independently hydrogen, halo, cyano, hydroxyl, amino, $C_{1-6}$ alkyl, $C_{3-6}$ cycloalkyl, alkylamino, haloalkyl, hydroxyalkyl, aminoalkyl, alkoxyalkyl, haloalkoxyalkyl, alkoxy, or haloalkoxy;

f is an integer of 0, 1, or 2;

Z is $CH_2$ or $NR^{8b}$; with the proviso that when Z is $NR^{8b}$, $Y^1$ is C;

n is 0 or 1; and $R^1$, $R^2$, n, $R^3$, $R^{5a}$, $R^{5b}$, $R^{8b}$, $X^1$, $X^2$, $X^3$, and $X^4$ are the same as defined above.

In one embodiment of Formula (IIa) or (IIb), $X^1$ is $CR^6$, where $R^6$ is hydrogen or $C_{1-4}$ alkyl.

In any one of the preceding embodiments of Formula (IIa) or (IIb), $X^3$ is N.

In any one of the preceding embodiments of Formula (IIa) or (IIb), the

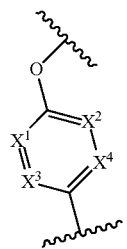

moiety is selected from

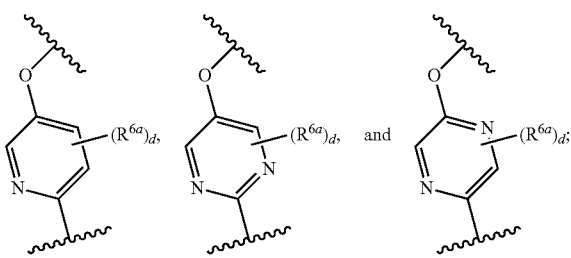

$R^{6a}$ is each independently halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; and d is an integer of 0, 1, or 2.

In any one of the preceding embodiments of Formula (IIa) or (IIb), the

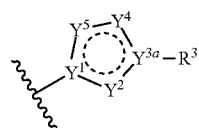

moiety is

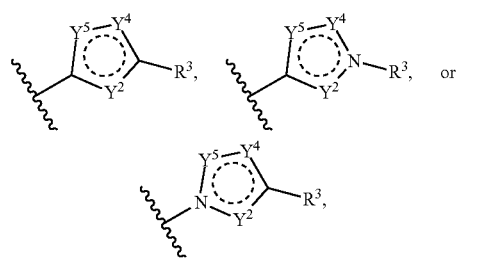

and
$Y^2$, $Y^4$, and $Y^5$ are each independently C, $CR^{4a}$, N, O or S.

In any one of the preceding embodiments of Formula (IIa) or (IIb), the

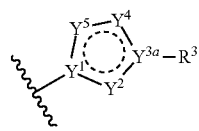

moiety is

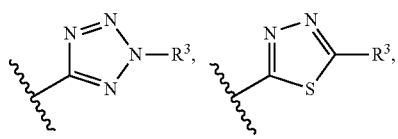

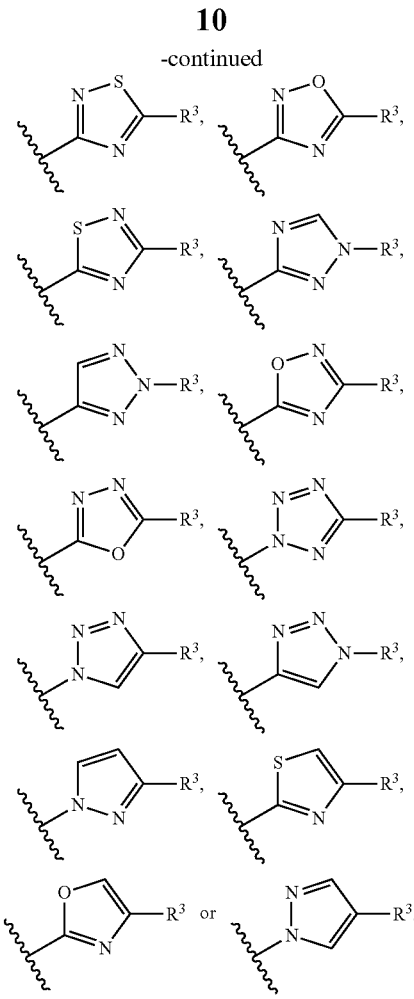

In any one of the preceding embodiments of Formula (IIa) or (IIb), the

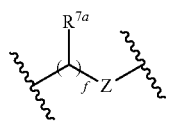

moiety is or

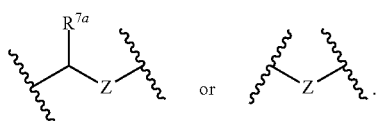

In any one of the preceding embodiments of Formula (IIa) or (IIb), $R^{7a}$ is hydrogen.

In any one of the preceding embodiments of Formula (IIa) or (IIb), $R^1$ is $CO_2H$.

In one embodiment, $R^2$ is hydrogen.

In any one of the preceding embodiments of Formula (IIa) or (IIb), the compound is represented by Formula (III):

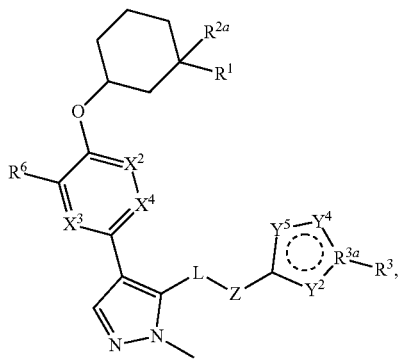

(III)

$Y^2$, $Y^{3a}$, $Y^4$, and $Y^5$ are each independently selected from C, $CR^{4a}$, N, $NR^{4b}$, S, or O; with the proviso that at least one of $Y^2$, $Y^{3a}$, $Y^4$, and $Y^5$ is N or $NR^{4b}$; and the dashed circle denotes optional bonds forming an aromatic ring; -L-Z— is $CH_2$ (i.e., L is a covalent bond, and Z is $CH_2$) or —$CH_2$—$NH_2$— (i.e., L is $CH_2$, and Z is $NH_2$); $R^{2a}$ is hydrogen, chloro, fluoro, or $C_{1-4}$ alkyl; $R^{4a}$ is each independently hydrogen, halo, $C_{1-4}$ alkyl, $C_{1-4}$ haloalkyl, $C_{2-6}$ alkoxyalkyl, or $C_{1-4}$ alkoxy; $R^{4b}$ is each independently hydrogen or $C_{1-4}$ alkyl; and $R^1$, $R^3$, $R^6$, $X^2$, $X^3$, and $X^4$ are the same as defined above.

In one embodiment of Formula (III), -L-Z— is —$CH_2$—$NH_2$—.

In any one of the preceding embodiments of Formula (III), the

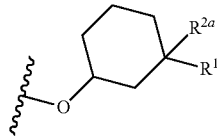

moiety is selected from

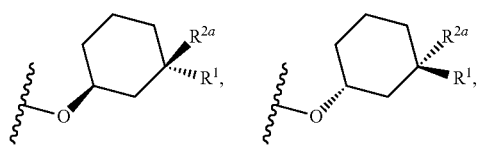

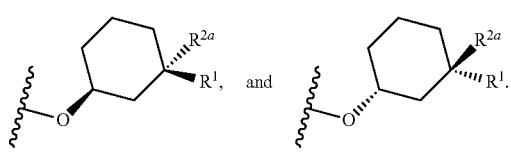

In one embodiment, $R^{2a}$ is hydrogen.

In any one of the preceding embodiments of Formula (III), $R^1$ is $CO_2H$.

In any one of the preceding embodiments of Formula (III), the

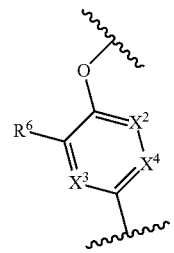

moiety is

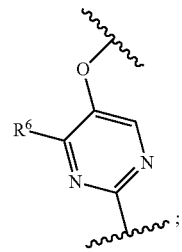

and $R^6$ is hydrogen, methyl, or ethyl.

In any one of the preceding embodiments of Formula (III), the

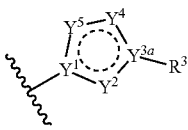

moiety is

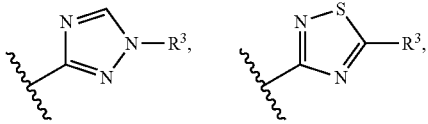

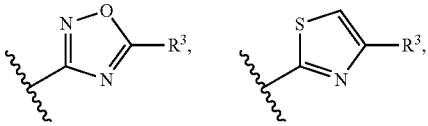

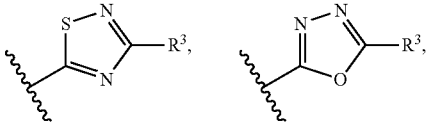

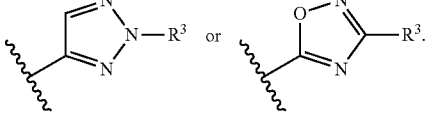

In any one of the preceding embodiments of Formula (III), $R^3$ is —$OR^a$, —$SR^a$, —$NR^cR^c$, $C_{1-6}$ alkyl, $C_{1-6}$ haloalkyl, $C_{1-6}$ heteroalkyl, 6- to 10-membered aryl, arylalkyl, 5- to 10-membered heteroaryl, heteroarylalkyl, 3- to 8-membered carbocyclyl, carbocyclylalkyl, 4- to 8-membered heterocyclyl, or heterocyclylalkyl; wherein the alkyl, heteroalkyl, aryl, heteroaryl, carbocyclyl, heterocyclyl, and $R^a$, by themselves or as part of another group, are each independently substituted with 0 to 5 $R^d$;

$R^a$ is selected from $C_{1-6}$ alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

$R^b$ is each independently hydrogen or $R^a$;

$R^c$ is each independently $R^b$; or alternatively, two $R^c$, taken together with the nitrogen atom to which they are attached, form a 4- to 7-membered heterocyclyl;

$R^d$ is each independently selected from $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —$OR^a$, —$SR^a$, and —$NR^cR^c$; or alternatively one or two $R^d$ on alkyl, heteroalkyl, aryl, heteroaryl, carbocyclyl, or heterocyclyl, taken together with the atoms to which the $R^d$ is attached, form a cyclic or bridge moiety.

In any one of the preceding embodiments of Formula (III), $R^3$ is $C_{1-6}$ alkyl, $C_{1-6}$ haloalkyl, $C_{1-6}$ alkoxy, $C_{1-6}$ haloalkoxy, $C_{3-6}$ cycloalkyl, 4 to 6-membered heterocyclyl, phenyl, (a 5 or 6-membered heteroaryl containing 1 to 3 heteroatoms each of which is independently selected from N, O, and S), —($C_{1-3}$ alkylene)-($C_{3-6}$ cycloalkyl), —($C_{1-3}$ alkylene)-(phenyl), —O—($C_{3-6}$ cycloalkyl), —O-(4 to 6-membered heterocyclyl), —O-phenyl, —O—($C_{1-3}$ alkylene)-(phenyl), —O—($C_{1-3}$ alkylene)-($C_{3-6}$ cycloalkyl), —NH—($C_{1-3}$ alkylene)-(phenyl), —NH-alkyl, —NH-haloalkyl, —NH-phenyl, —NH-cycloalkyl, and —N(alkyl)$_2$; and the alkyl, alkylene, cycloalkyl, phenyl, heterocyclyl, and heteroaryl, by themselves or as part of another group, are each independently substituted with 0 to 3 $R^d$; $R^d$ is halo, cyano, hydroxyl, amino, $C_{1-6}$ alkyl, $C_{1-6}$ alkoxy, $C_{3-6}$ cycloalkyl, or 4 to 6-membered heterocyclyl; $R^{4a}$ is hydrogen; and $R^b$ is hydrogen.

In any one of the preceding embodiments of Formula (III), $R^3$ is $C_{1-6}$ alkyl, $C_{1-6}$ haloalkyl, $C_{1-6}$ alkoxy, $C_{1-6}$ haloalkoxy, $C_{3-6}$ cycloalkyl, phenyl, —($C_{1-3}$ alkylene)-($C_{3-6}$ cycloalkyl), —($C_{1-3}$ alkylene)-(phenyl); and the alkyl, alkylene, cycloalkyl, phenyl, heterocyclyl, and heteroaryl, by themselves or as part of another group, are each independently substituted with 0 to 3 $R^d$.

In one embodiment of the present invention, the compound is selected from any one of the Examples as described in the specification, or a stereoisomer, a tautomer, or a pharmaceutically acceptable salt or solvate thereof.

In another embodiment of the present invention, the compound is selected from Examples 1 to 12 as described in the specification, or a stereoisomer, a tautomer, or a pharmaceutically acceptable salt or solvate thereof.

In another embodiment of the present invention, the compound is selected from Examples 1 to 8 as described in the specification, or a stereoisomer, a tautomer, or a pharmaceutically acceptable salt or solvate thereof.

In one embodiment, the compounds of the present invention have hLPA$_1$ IC$_{50}$ values ≤5000 nM, using the LPA$_1$ functional antagonist assay; in another embodiment, the compounds of the present invention have hLPA$_1$ IC$_{50}$ values ≤1000 nM; in another embodiment, the compounds of the present invention have hLPA$_1$ IC$_{50}$ values ≤500 nM; in another embodiment, the compounds of the present invention have hLPA$_1$ IC$_{50}$ values ≤200 nM; in another embodiment, the compounds of the present invention have hLPA$_1$ IC$_{50}$ values ≤100 nM; in another embodiment, the compounds of the present invention have hLPA$_1$ IC$_{50}$ values 50 nM.

II. Other Embodiments of the Invention

In some embodiments, the compound of Formulas (I), or a pharmaceutically acceptable salt or solvate thereof, is an antagonist of at least one LPA receptor. In some embodiments, the compound of Formula (I), or a pharmaceutically acceptable salt or solvate thereof, is an antagonist of LPA$_1$. In some embodiments, the compound of Formula (I), or a pharmaceutically acceptable salt or solvate thereof, is an antagonist of LPA$_2$. In some embodiments, the compound of Formula (I), or a pharmaceutically acceptable salt or solvate thereof, is an antagonist of LPA$_3$.

In some embodiments, presented herein are compounds selected from active metabolites, tautomers, pharmaceutically acceptable salts or solvates of a compound of Formula (I).

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment of a condition associated with LPA receptor mediated fibrosis, comprising administering to a patient in need of such treatment a therapeutically effective amount of at least one of the compounds of the present invention or a stereoisomer, a tautomer, a pharmaceutically acceptable salt, or a solvate thereof. As used herein, the term "patient" encompasses all mammalian species.

In another embodiment, the present invention provides a method of treating a disease, disorder, or condition associated with dysregulation of lysophosphatidic acid receptor 1 (LPA$_1$) in a patient in need thereof, comprising administering a therapeutically effective amount of a compound of the present invention, or a stereoisomer, a tautomer, or a pharmaceutically acceptable salt or solvate thereof, to the patient. In one embodiment of the method, the disease, disorder, or condition is related to pathological fibrosis, transplant rejection, cancer, osteoporosis, or inflammatory disorders. In one embodiment of the method, the pathological fibrosis is pulmonary, liver, renal, cardiac, dermal, ocular, or pancreatic fibrosis. In one embodiment of the method, the disease, disorder, or condition is idiopathic pulmonary fibrosis (IPF), non-alcoholic steatohepatitis (NASH), non-alcoholic fatty liver disease (NAFLD), chronic kidney disease, diabetic kidney disease, and systemic sclerosis. In one embodiment of the method, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

In another embodiment, the present invention provides a method of treating fibrosis in a mammal comprising administering a therapeutically effective amount of a compound of the present invention, or a stereoisomer, a tautomer, or a pharmaceutically acceptable salt or solvate thereof, to the mammal in need thereof. In one embodiment of the method, the fibrosis is idiopathic pulmonary fibrosis (IPF), nonalcoholic steatohepatitis (NASH), chronic kidney disease, diabetic kidney disease, and systemic sclerosis.

In another embodiment, the present invention provides a method of treating lung fibrosis (idiopathic pulmonary fibrosis), asthma, chronic obstructive pulmonary disease (COPD), renal fibrosis, acute kidney injury, chronic kidney disease, liver fibrosis (non-alcoholic steatohepatitis), skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, cancer pain, tumor metastasis, transplant organ rejection, scleroderma, ocular fibrosis, age related macular degeneration (AMD), diabetic retinopathy, collagen vascular disease, atherosclerosis, Raynaud's phenomenon, or neuropathic pain in a mammal comprising administering a therapeutically effective amount of a compound of the present invention, or a stereoisomer, a tautomer, or a pharmaceutically acceptable salt or solvate thereof, to the mammal in need thereof.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state. As used herein, "treating" or "treatment" also include the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for such protective therapy based on factors that are known to increase risk of suffering a clinical disease state compared to the general population. For protective treatment, conditions of the clinical disease state may or may not be presented yet. The protective treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. While "alkyl" denotes a monovalent saturated aliphatic radical (such as ethyl), "alkylene" denotes a bivalent saturated aliphatic radical (such as ethylene). For example, "$C_1$ to $C_{10}$ alkyl" or "$C_{1-10}$ alkyl" is intended to include $C_1$, $C_2$, $C_3$, $C_4$, $C_5$, $C_6$, $C_7$, $C_8$, $C_9$, and $C_{10}$ alkyl groups. "$C_1$ to $C_{10}$ alkylene" or "$C_{1-10}$ alkylene", is intended to include $C_1$, $C_2$, $C_3$, $C_4$, $C_5$, $C_6$, $C_7$, $C_8$, $C_9$, and $C_{10}$ alkylene groups. Additionally, for example, "$C_1$ to $C_6$ alkyl" or "$C_{1-6}$ alkyl" denotes alkyl having 1 to 6 carbon atoms; and "$C_1$ to $C_6$ alkylene" or "$C_{1-6}$ alkylene" denotes alkylene having 1 to 6 carbon atoms; and "$C_1$ to $C_4$ alkyl" or "$C_{1-4}$ alkyl" denotes alkyl having 1 to 4 carbon atoms; and "$C_1$ to $C_4$ alkylene" or "$C_{1-4}$ alkylene" denotes alkylene having 1 to 4 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond. Furthermore, the term "alkyl", by itself or as part of another group, such as alkylamino, haloalkyl, hydroxyalkyl, aminoalkyl, alkoxy, alkoxyalkyl, haloalkoxyalkyl, and haloalkoxy, can be an alkyl having 1 to 4 carbon atoms, or 1 to 6 carbon atoms, or 1 to 10 carbon atoms.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an alkylamino (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkylaminoalkyl (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$. "Benzyl" can also be represented by formula "Bn".

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —$S(O)_2R'$, while sulfonamide may be represented by —$S(O)_2NR^cR^d$. R' is $C_1$ to $C_6$ alkyl; and $R^c$ and $R^d$ are the same as defined below for "amino".

The term "carbamate" as used herein alone or as part of another group refers to oxygen linked to an amido group. For example, carbamate may be represented by $N(R^cR^d)$—C(O)—O—, and $R^c$ and $R^d$ are the same as defined below for "amino".

The term "amido" as used herein alone or as part of another group refers to amino linked to a carbonyl group. For example, amido may be represented by $N(R^d)$—C(O)—, and $R^c$ and $R^d$ are the same as defined below for "amino".

The term "amino" is defined as —$NR^{c1}R^{c2}$, wherein $R^{c1}$ and $R^{c2}$ are independently H or $C_{1-6}$ alkyl; or alternatively, $R^{c1}$ and $R^{c2}$, taken together with the atoms to which they are attached, form a 3- to 8-membered heterocyclic ring which is optionally substituted with one or more group selected from halo, cyano, hydroxyl, amino, oxo, $C_{1-6}$ alkyl, alkoxy, and aminoalkyl. When $R^{c1}$ or $R^{c2}$ (or both of them) is Cia alkyl, the amino group can also be referred to as alkylamino. Examples of alkylamino group include, without limitation, methylamino, ethylamino, propylamino, isopropylamino and the like. In one embodiment, amino is —NH$_2$.

The term "aminoalkyl" refers to an alkyl group on which one of the hydrogen atoms is replaced by an amino group. For example, aminoalkyl may be represented by N(R$^{c1}$R$^{c2}$)-alkylene-. "C$_1$ to C$_6$" or "C$_{1-6}$" aminoalkyl" (or aminoalkyl), is intended to include C$_1$, C$_2$, C$_3$, C$_4$, C$_5$, and C$_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "C$_1$ to C$_6$ haloalkyl" or "C$_{1-6}$ haloalkyl" (or haloalkyl), is intended to include C$_1$, C$_2$, C$_3$, C$_4$, C$_5$, and C$_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, CF$_3$CH$_2$, CF$_3$ or CF$_3$CF$_2$CH$_2$.

"Haloalkoxy" or "haloalkyloxy" represents a haloalkyl group as defined above with the indicated number of carbon atoms attached through an oxygen bridge. For example, "C$_1$ to C$_6$ haloalkoxy" or "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, CF$_3$CH$_2$O, CF$_3$O or CF$_3$CF$_2$CH$_2$O.

"Hydroxyalkyl" is intended to include both branched and straight-chain saturated aliphatic hydrocarbon groups having the specified number of carbon atoms, substituted with 1 or more hydroxyl (OH). "C$_1$ to C$_6$ hydroxyalkyl" (or hydroxyalkyl), is intended to include C$_1$, C$_2$, C$_3$, C$_4$, C$_5$, and C$_6$ hydroxyalkyl groups.

The term "cycloalkyl" refers to cyclized alkyl groups, including mono-, bi- or poly-cyclic ring systems. "C$_3$ to C$_8$ cycloalkyl" or "C$_{3-8}$ cycloalkyl" is intended to include C$_3$, C$_4$, C$_5$, C$_6$, C$_7$, and C$_8$ cycloalkyl groups, including monocyclic, bicyclic, and polycyclic rings. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl and spiro and bridged cycloalkyl groups are included in the definition of "cycloalkyl".

The term "cycloheteroalkyl" refers to cyclized heteroalkyl groups, including mono-, bi- or poly-cyclic ring systems. "C$_3$ to C$_7$ cycloheteroalkyl" or "C$_{3-7}$ cycloheteroalkyl" is intended to include C$_3$, C$_4$, C$_5$, C$_6$, and C$_7$ cycloheteroalkyl groups.

Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons or 3 to 6 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

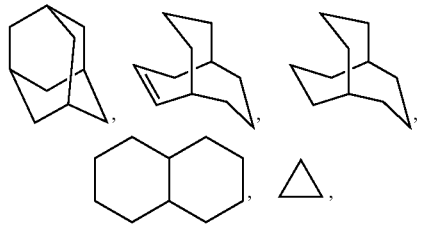

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6\text{-}10}$ aryl" refers to phenyl and naphthyl. Unless otherwise specified, "aryl", "$C_6$ or $C_{10}$ aryl", "$C_{6\text{-}10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of hetercyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of heteroaryl also include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heteroaryl include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl. In some embodiments, the heteroaryl are selected from benzthiazolyl, imidazolpyridinyl, pyrrolopyridinyl, quinolinyl, and indolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings), for example,

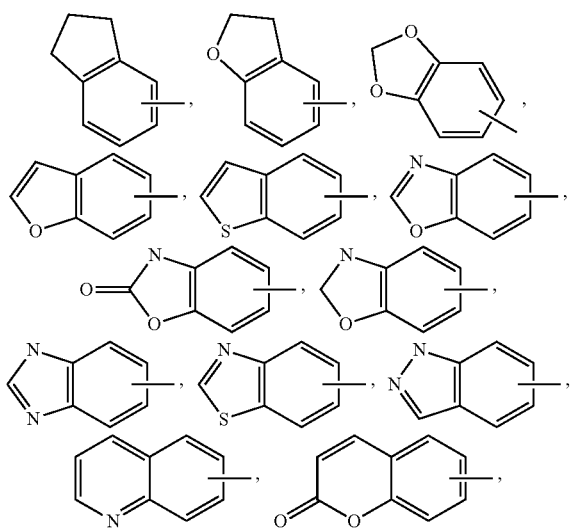

and may be optionally substituted through available carbon or nitrogen atoms (as applicable) with 1, 2, or 3 groups selected from hydrogen, halo, haloalkyl, alkyl, haloalkoxy, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

When any of the terms alkyl, alkenyl, alkynyl, cycloalkyl, carbocyclyl, heterocyclyl, aryl, and heteroaryl are used as part of another group, the number of carbon atoms and ring members are the same as those defined in the terms by themselves. For example, alkoxy, haloalkoxy, alkylamino, haloalkyl, hydroxyalkyl, aminoalkyl, haloalkoxy, alkoxyalkyl, haloalkylamino, alkoxyalkylamino, haloalkoxyalkylamino, alkylthio, and the like each independently contains the number of carbon atoms which are the same as defined for the term "alkyl", such as 1 to 4 carbon atoms, 1 to 6 carbon atoms, 1 to 10 carbon atoms, etc. Similarly, cycloalkoxy, heterocyclyloxy, cycloalkylamino, heterocyclylamino, aralkylamino, arylamino, aryloxy, aralkyloxy, heteroaryloxy, heteroarylalkyloxy, and the like each independently contains ring members which are the same as defined for the terms "cycloalkyl", "heterocyclyl", "aryl", and "heteroaryl", such as 3 to 6-membered, 4 to 7-membered, 6 to 10-membered, 5 to 10-membered, 5 or 6-membered, etc.

In accordance with a convention used in the art, a bond pointing to a bold line, such as

as used in structural formulas herein, depicts the bond that is the point of attachment of the moiety or substituent to the core or backbone structure.

In accordance with a convention used in the art, a wavy or squiggly bond in a structural formula, such

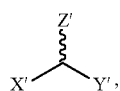

is used to depict a stereogenic center of the carbon atom to which X', Y', and Z' are attached and is intended to represent both enantiomers in a single figure. That is, a structural formula with such as wavy bond denotes each of the enantiomers individually, such as

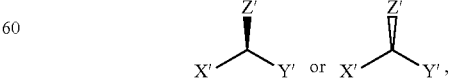

as well as a racemic mixture thereof. When a wavy or squiggly bon is attached to a double bond (such as C=C or C=N) moiety, it include cis- or trans- (or E- and Z-) geometric isomers or a mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom (attached to carbon atom or heteroatom) is replaced with a non-hydrogen group, provided that normal valencies are maintained and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N). The term "substituted" in reference to alkyl, cycloalkyl, heteroalkyl, cycloheteroalkyl, alkylene, aryl, arylalkyl, heteroaryl, heteroarylalkyl, carbocyclyl, and heterocyclyl, means alkyl, cycloalkyl, heteroalkyl, cycloheteroalkyl, alkylene, aryl, arylalkyl, heteroaryl, heteroarylalkyl, carbocyclyl, and heterocyclyl, respectively, in which one or more hydrogen atoms, which are attached to either carbon or heteroatom, are each independently replaced with one or more non-hydrogen substituent(s).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

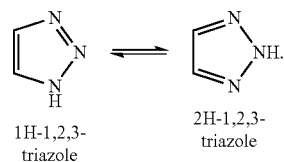 [SMILES: c1c[nH]nn1 ; c1cn[nH]n1]

1H-1,2,3-triazole     2H-1,2,3-triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula (I) or their pharmaceutically acceptable salts, are also included.

Preferred salts of the compounds of Formula (I) which contain a basic group include monohydrochloride, hydrogensulfate, methanesulfonate, phosphate, nitrate or acetate.

Preferred salts of the compounds of Formula (I) which contain an acid group include sodium, potassium and magnesium salts and pharmaceutically acceptable organic amines.

In addition, compounds of Formula (I) may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988); and
e) Kakeya, N. et al., *Chem. Pharm. Bull.*, 32:692 (1984).

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2H$" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "L" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "γ", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
AcOH or HOAc acetic acid
AlCl$_3$ aluminum trichloride
AIBN Azobis-isobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
DCM or CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DEA Diethylamine
DEAD Diethyl azodicarboxylate
Dess-Martin 1,1,1-tris(acetyloxy)-1,1-dihydro-1,2-benziodoxol-3-(1H)-one
DIAD Diisopropyl azodicarboxylate
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complementary DNA
Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylpholano)benzene(1,5-cyclooctadiene)rhodium (I) trifluoromethanesulfonate
Et$_3$N or TEA triethylamine
EtOAc ethyl acetate
Et$_2$O diethyl ether
EtOH ethanol
GMF glass microfiber filter
Grubbs II (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexane
HOBt or HOBT 1-hydroxybenzotriazole
H$_2$O$_2$ hydrogen peroxide
IBX 2-iodoxybenzoic acid
H$_2$SO$_4$ sulfuric acid
Jones reagent CrO$_3$ in aqueous H$_2$SO$_4$, 2 M solution
K$_2$CO$_3$ potassium carbonate
K$_2$HPO$_4$ potassium phosphate dibasic (potassium hydrogen phosphate)
KOAc potassium acetate
K$_3$PO$_4$ potassium phosphate tribasic
LAH lithium aluminum hydride
LG leaving group
LiOH lithium hydroxide
MeOH methanol
MgSO$_4$ magnesium sulfate
MsOH or MSA methylsulfonic acid/methanesulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
NH$_4^+$HCO$_2^-$ ammonium formate
NMM N-methylmorpholine
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
PPTS pyridinium p-toluenesulfonate
i-PrOH or IPA isopropanol
PS Polystyrene
RT or rt room temperature
SEM-Cl 2-(trimethysilyl)ethoxymethyl chloride
SiO$_2$ silica oxide
SnCl$_2$ tin(II) chloride
TBAF tra-n-butylammonium fluoride
TBAI tetra-n-butylammonium iodide
TFA trifluoroacetic acid
THF tetrahydrofuran
THP tetrahydropyran
TMSCHN$_2$ Trimethylsilyldiazomethane
TMSCH$_2$N$_3$ Trimethylsilylmethyl azide
T3P propane phosphonic acid anhydride
TRIS tris (hydroxymethyl) aminomethane
pTsOH p-toluenesulfonicacid

IV. Biology

Lysophospholipids are membrane-derived bioactive lipid mediators. Lysophospholipids include, but are not limited to, lysophosphatidic acid (1-acyl-2-hydroxy-sn-glycero-3-phosphate; LPA), sphingosine 1-phosphate (S1P), lysophosphatidylcholine (LPC), and sphingosylphosphorylcholine (SPC). Lysophospholipids affect fundamental cellular functions that include cellular proliferation, differentiation, survival, migration, adhesion, invasion, and morphogenesis. These functions influence many biological processes that include neurogenesis, angiogenesis, wound healing, immunity, and carcinogenesis.

LPA acts through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses.

Lysophospholipids, such as LPA, are quantitatively minor lipid species compared to their major phospholipid counterparts (e.g., phosphatidylcholine, phosphatidylethanolamine, and sphingomyelin). LPA has a role as a biological effector molecule, and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated.

Activation of the LPA receptors ($LPA_1$, $LPA_2$, $LPA_3$, $LPA_4$, $LPA_5$, $LPA_6$) with LPA mediates a range of downstream signaling cascades. These include, but are not limited to, mitogen-activated protein kinase (MAPK) activation, adenylyl cyclase (AC) inhibition/activation, phospholipase C (PLC) activation/$Ca^{2+}$ mobilization, arachidonic acid release, Akt/PKB activation, and the activation of small GTPases, Rho, ROCK, Rac, and Ras. Other pathways that are affected by LPA receptor activation include, but are not limited to, cyclic adenosine monophosphate (cAMP), cell division cycle 42/GTP-binding protein (Cdc42), proto-oncogene serine/threonine-protein kinase Raf (c-RAF), proto-oncogene tyrosine-protein kinase Src (c-src), extracellular signal-regulated kinase (ERK), focal adhesion kinase (FAK), guanine nucleotide exchange factor (GEF), glycogen synthase kinase 3b (GSK3b), c-jun amino-terminal kinase (JNK), MEK, myosin light chain II (MLC II), nuclear factor kB (NF-kB), N-methyl-D-aspartate (NMDA) receptor activation, phosphatidylinositol 3-kinase (PI3K), protein kinase A (PKA), protein kinase C (PKC), ras-related $C_3$ botulinum toxin substrate 1 (RAC1). The actual pathway and realized end point are dependent on a range of variables that include receptor usage, cell type, expression level of a receptor or signaling protein, and LPA concentration. Nearly all mammalian cells, tissues and organs co-express several LPA-receptor subtypes, which indicates that LPA receptors signal in a cooperative manner. $LPA_1$, $LPA_2$, and $LPA_3$ share high amino acid sequence similarity.

LPA is produced from activated platelets, activated adipocytes, neuronal cells, and other cell types. Serum LPA is produced by multiple enzymatic pathways that involve monoacylglycerol kinase, phospholipase $A_1$, secretory phospholipase $A_2$, and lysophospholipase D (lysoPLD), including autotaxin. Several enzymes are involved in LPA degradation: lysophospholipase, lipid phosphate phosphatase, and LPA acyl transferase such as endophilin. LPA concentrations in human serum are estimated to be 1-5 µM. Serum LPA is bound to albumin, low-density lipoproteins, or other proteins, which possibly protect LPA from rapid degradation. LPA molecular species with different acyl chain lengths and saturation are naturally occurring, including 1-palmitoyl (16:0), 1-palmitoleoyl (16:1), 1-stearoyl (18:0), 1-oleoyl (18:1), 1-linoleoyl (18:2), and 1-arachidonyl (20:4) LPA. Quantitatively minor alkyl LPA has biological activities similar to acyl LPA, and different LPA species activate LPA receptor subtypes with varied efficacies.

LPA Receptors $LPA_1$ (previously called VZG-1/EDG-2/mrec1.3) couples with three types of G proteins, $G_{i/o}$, $G_q$, and $G_{12/23}$. Through activation of these G proteins, LPA induces a range of cellular responses through $LPA_1$ including but not limited to: cell proliferation, serum-response element (SRE) activation, mitogen-activated protein kinase (MAPK) activation, adenylyl cyclase (AC) inhibition, phospholipase C (PLC) activation, $Ca^{2+}$ mobilization, Akt activation, and Rho activation.

Wide expression of $LPA_1$ is observed in adult mice, with clear presence in testis, brain, heart, lung, small intestine, stomach, spleen, thymus, and skeletal muscle. Similarly, human tissues also express $LPA_1$; it is present in brain, heart, lung, placenta, colon, small intestine, prostate, testis, ovary, pancreas, spleen, kidney, skeletal muscle, and thymus.

$LPA_2$ (EDG-4) also couples with three types of G proteins, $G_{i/o}$, $G_q$, and $G_{12/13}$, to mediate LPA-induced cellular signaling. Expression of $LPA_2$ is observed in the testis, kidney, lung, thymus, spleen, and stomach of adult mice and in the human testis, pancreas, prostate, thymus, spleen, and peripheral blood leukocytes. Expression of $LPA_2$ is upregulated in various cancer cell lines, and several human $LPA_2$ transcriptional variants with mutations in the 3'-untranslated region have been observed. Targeted deletion of $LPA_2$ in mice has not shown any obvious phenotypic abnormalities, but has demonstrated a significant loss of normal LPA signaling (e.g., PLC activation, $Ca^{2+}$ mobilization, and stress fiber formation) in primary cultures of mouse embryonic fibroblasts (MEFs). Creation of lpa1(−/−) lpa2 (−/−) double-null mice has revealed that many LPA-induced responses, which include cell proliferation, AC inhibition, PLC activation, $Ca^{2+}$ mobilization, JNK and Akt activation, and stress fiber formation, are absent or severely reduced in double-null MEFs. All these responses, except for AC inhibition (AC inhibition is nearly abolished in $LPA_1$ (−/−) MEFs), are only partially affected in either $LPA_1$ (−/−) or $LPA_2$ (−/−) MEFs. $LPA_2$ contributes to normal LPA-mediated signaling responses in at least some cell types (Choi et al, *Biochemica et Biophysica Acta* 2008, 1781, p 531-539).

$LPA_3$ (EDG-7) is distinct from $LPA_1$ and $LPA_2$ in its ability to couple with $G_{i/o}$ and $G_q$ but not $G_{12/13}$ and is much less responsive to LPA species with saturated acyl chains. $LPA_3$ can mediate pleiotropic LPA-induced signaling that includes PLC activation, $Ca^{2+}$ mobilization, AC inhibition/activation, and MAPK activation. Overexpression of $LPA_3$ in neuroblastoma cells leads to neurite elongation, whereas that of $LPA_1$ or $LPA_2$ results in neurite retraction and cell rounding when stimulated with LPA. Expression of $LPA_3$ is observed in adult mouse testis, kidney, lung, small intestine, heart, thymus, and brain. In humans, it is found in the heart, pancreas, prostate, testis, lung, ovary, and brain (frontal cortex, hippocampus, and amygdala).

$LPA_4$ ($p2y_9$/GPR23) is of divergent sequence compared to $LPA_1$, $LPA_2$, and $LPA_3$ with closer similarity to the platelet-activating factor (PAF) receptor. $LPA_4$ mediates LPA induced $Ca^{2+}$ mobilization and cAMP accumulation, and functional coupling to the G protein Gs for AC activation, as well as coupling to other G proteins. The $LPA_4$ gene is expressed in the ovary, pancreas, thymus, kidney and skeletal muscle.

$LPA_5$ (GPR92) is a member of the purinocluster of GPCRs and is structurally most closely related to $LPA_4$. $LPA_5$ is expressed in human heart, placenta, spleen, brain, lung and gut. $LPA_5$ also shows very high expression in the CD8+ lymphocyte compartment of the gastrointestinal tract.

$LPA_6$ ($p2y_5$) is a member of the purinocluster of GPCRs and is structurally most closely related to $LPA_4$. $LPA_6$ is an LPA receptor coupled to the G12/13-Rho signaling pathways and is expressed in the inner root sheaths of human hair follicles.

Illustrative Biological Activity

Wound Healing

Normal wound healing occurs by a highly coordinated sequence of events in which cellular, soluble factors and matrix components act in concert to repair the injury. The healing response can be described as taking place in four broad, overlapping phases—hemostasis, inflammation, proliferation, and remodeling. Many growth factors and cytokines are released into a wound site to initiate and perpetuate wound healing processes.

When wounded, damaged blood vessels activate platelets. The activated platelets play pivotal roles in subsequent repair processes by releasing bioactive mediators to induce cell proliferation, cell migration, blood coagulation, and angiogenesis. LPA is one such mediator that is released from activated platelets; this induces platelet aggregation along with mitogenic/migration effects on the surrounding cells, such as endothelial cells, smooth muscle cells, fibroblasts, and keratinocytes.

Topical application of LPA to cutaneous wounds in mice promotes repair processes (wound closure and increased neoepithelial thickness) by increasing cell proliferation/migration without affecting secondary inflammation.

Activation of dermal fibroblasts by growth factors and cytokines leads to their subsequent migration from the edges of the wound into the provisional matrix formed by the fibrin clot whereupon the fibroblasts proliferate and start to restore the dermis by secreting and organizing the characteristic dermal extracellular matrix (ECM). The increasing number of fibroblasts within the wound and continuous precipitation of ECM enhances matrix rigidity by applying small tractional forces to the newly formed granulation tissue. The increase in mechanical stress, in conjunction with transforming growth factor β (TGFβ), induces α-smooth muscle actin (α-SMA) expression and the subsequent transformation of fibroblasts into myofibroblasts. Myofibroblasts facilitate granulation tissue remodeling via myofibroblast contraction and through the production of ECM components.

LPA regulates many important functions of fibroblasts in wound healing, including proliferation, migration, differentiation and contraction. Fibroblast proliferation is required in wound healing in order to fill an open wound. In contrast, fibrosis is characterized by intense proliferation and accumulation of myofibroblasts that actively synthesize ECM and proinflammatory cytokines. LPA can either increase or suppress the proliferation of cell types important in wound healing, such as epithelial and endothelial cells (EC), macrophages, keratinocytes, and fibroblasts. A role for $LPA_1$ in LPA-induced proliferation was provided by the observation that LPA-stimulated proliferation of fibroblasts isolated from $LPA_1$ receptor null mice was attenuated (Mills et al, *Nat Rev. Cancer* 2003; 3: 582-591). LPA induces cytoskeletal changes that are integral to fibroblast adhesion, migration, differentiation and contraction.

Fibrosis

Tissue injury initiates a complex series of host wound-healing responses; if successful, these responses restore normal tissue structure and function. If not, these responses can lead to tissue fibrosis and loss of function.

For the majority of organs and tissues the development of fibrosis involves a multitude of events and factors. Molecules involved in the development of fibrosis include proteins or peptides (profibrotic cytokines, chemokines, metalloproteinases etc.) and phospholipids. Phospholipids involved in the development of fibrosis include platelet activating factor (PAF), phosphatidyl choline, sphingosine-1 phosphate (S1P) and lysophosphatidic acid (LPA).

A number of muscular dystrophies are characterized by a progressive weakness and wasting of musculature, and by extensive fibrosis. It has been shown that LPA treatment of cultured myoblasts induced significant expression of connective tissue growth factor (CTGF). CTGF subsequently induces collagen, fibronectin and integrin expression and induces dedifferentiation of these myoblasts. Treatment of a variety of cell types with LPA induces reproducible and high level induction of CTGF (J. P. Pradere, et al., $LPA_1$ receptor activation promotes renal interstitial fibrosis, *J. Am. Soc. Nephrol.* 18 (2007) 3110-3118; N. Wiedmaier, et al., *Int J Med Microbiol;* 298(3-4):231-43, 2008). CTGF is a profibrotic cytokine, signaling down-stream and in parallel with TGFβ.

CTGF expression by gingival epithelial cells, which are involved in the development of gingival fibromatosis, was found to be exacerbated by LPA treatment (A. Kantarci, et al., *J. Pathol.* 210 (2006) 59-66).

LPA is associated with the progression of liver fibrosis. In vitro, LPA induces stellate cell and hepatocyte proliferation. These activated cells are the main cell type responsible for the accumulation of ECM in the liver. Furthermore, LPA plasma levels rise during $CCl_4$-induced liver fibrosis in rodents, or in hepatitis C virus-induced liver fibrosis in humans (N. Watanabe, et al., Plasma lysophosphatidic acid level and serum autotaxin activity are increased in liver injury in rats in relation to its severity, *Life Sci.* 81 (2007) 1009-1015; N. Watanabe, et al., *J Clin. Gastroenterol.* 41 (2007) 616-623).

An increase of phospholipid concentrations in the bronchoalveolar lavage fluid in rabbits and rodents injected with bleomycin has been reported (K. Kuroda, et al., Phospholipid concentration in lung lavage fluid as biomarker for pulmonary fibrosis, *Inhal. Toxicol.* 18 (2006) 389-393; K. Yasuda, et al., Lung 172 (1994) 91-102).

LPA is associated with heart disease and myocardial remodeling. Serum LPA levels are increased after myocardial infarction in patients and LPA stimulates rat cardiac fibroblast proliferation and collagen production (Chen et al. *FEBS Lett.* 2006 Aug. 21; 580(19):4737-45).

Pulmonary Fibrosis

In the lung, aberrant wound healing responses to injury contribute to the pathogenesis of fibrotic lung diseases. Fibrotic lung diseases, such as idiopathic pulmonary fibrosis (IPF), are associated with high morbidity and mortality.

LPA is an important mediator of fibroblast recruitment in pulmonary fibrosis. LPA and $LPA_1$ play key pathogenic roles in pulmonary fibrosis. Fibroblast chemoattractant activity plays an important role in the lungs in patients with pulmonary fibrosis. Profibrotic effects of $LPA_1$-receptor stimulation is explained by LPA-receptor-mediated vascular leakage and increased fibroblast recruitment, both profibrotic events. The LPA-LPA$_1$ pathway has a role in mediating fibroblast migration and vascular leakage in IPF. The end result is the aberrant healing process that characterizes this fibrotic condition.

The LPA$_1$ receptor is the LPA receptor most highly expressed on fibroblasts obtained from patients with IPF. Furthermore, BAL obtained from IPF patients induced chemotaxis of human foetal lung fibroblasts that was blocked by the dual LPA$_1$-LPA$_3$ receptor antagonist Ki16425. In an experimental bleomycin-induced lung injury mouse model, it was shown that LPA levels were high in bronchoalveolar lavage samples compared with unexposed controls. LPA$_1$ knockout mice are protected from fibrosis after bleomycin challenge with reduced fibroblast accumulation and vascular leakage. In human subjects with IPF, high LPA levels were observed in bronchoalveolar lavage samples compared with healthy controls. Increased fibroblast chemotactic activity in these samples was inhibited by the Ki16425 indicating that fibroblast migration is mediated by the LPA-LPA receptor(s) pathway (Tager et al. *Nature Medicine,* 2008, 14, 45-54).

The LPA-LPA$_1$ pathway is crucial in fibroblast recruitment and vascular leakage in pulmonary fibrosis.

Activation of latent TGF-β by the αvβ6 integrin plays a critical role in the development of lung injury and fibrosis (Munger et al. *Cell*, vol. 96, 319-328, 1999). LPA induces αvβ6-mediated TGF-β activation on human lung epithelial cells (Xu et al. *Am. J Pathology,* 2009, 174, 1264-1279). The LPA-induced αvβ6-mediated TGF-β activation is mediated by the LPA$_2$ receptor. Expression of the LPA$_2$ receptor is increased in epithelial cells and mesenchymal cells in areas of lung fibrosis from IPF patients compared to normal human lung tissue. The LPA-LPA$_2$ pathway contributes to the activation of the TGF-β pathway in pulmonary fibrosis. In some embodiments, compounds that inhibit LPA$_2$ show efficacy in the treatment of lung fibrosis. In some embodiments, compounds that inhibit both LPA$_1$ and LPA$_2$ show improved efficacy in the treatment of lung fibrosis compared to compounds which inhibit only LPA$_1$ or LPA$_2$.

Renal Fibrosis

LPA and LPA$_1$ are involved in the etiology of kidney fibrosis. LPA has effects on both proliferation and contraction of glomerular mesangial cells and thus has been implicated in proliferative glomerulonephritis (C. N. Inoue, et al., *Clin. Sci.* (Colch.) 1999, 96, 431-436). In an animal model of renal fibrosis [unilateral ureteral obstruction (UUO)], it was found that renal LPA receptors are expressed under basal conditions with an expression order of LPA$_2$>LPA$_3$=LPA$_1$>>LPA$_4$. This model mimics in an accelerated manner the development of renal fibrosis including renal inflammation, fibroblast activation and accumulation of extracellular matrix in the tubulointerstitium. UUO significantly induced LPA$_1$-receptor expression. This was paralleled by renal LPA production (3.3 fold increase) in conditioned media from kidney explants. Contra-lateral kidneys exhibited no significant changes in LPA release and LPA-receptors expression. This shows that a prerequisite for an action of LPA in fibrosis is met: production of a ligand (LPA) and induction of one of its receptors (the LPA$_1$ receptor) (J. P. Pradere et al., *Biochimica et Biophysica Acta,* 2008, 1781, 582-587).

In mice where the LPA$_1$ receptor was knocked out (LPA$_1$ (−/−), the development of renal fibrosis was significantly attenuated. UUO mice treated with the LPA receptor antagonist Ki16425 closely resembled the profile of LPA$_1$ (−/−) mice.

LPA can participate in intraperitonial accumulation of monocyte/macrophages and LPA can induce expression of the profibrotic cytokine CTGF in primary cultures of human fibroblasts (J. S. Koh, et al., *J Clin. Invest.,* 1998, 102, 716-727).

LPA treatment of a mouse epithelial renal cell line, MCT, induced a rapid increase in the expression of the profibrotic cytokine CTGF. CTGF plays a crucial role in UUO-induced tubulointerstitial fibrosis (TIF), and is involved in the profibrotic activity of TGFβ. This induction was almost completely suppressed by co-treatment with the LPA-receptor antagonist Ki16425. In one aspect, the profibrotic activity of LPA in kidney results from a direct action of LPA on kidney cells involving induction of CTGF.

Hepatic Fibrosis

LPA is implicated in liver disease and fibrosis. Plasma LPA levels and serum autotaxin (enzyme responsible for LPA production) are elevated in hepatitis patients and animal models of liver injury in correlation with increased fibrosis. LPA also regulates liver cell function. LPA$_1$ and LPA$_2$ receptors are expressed by mouse hepatic stellate cells and LPA stimulates migration of hepatic myofibroblasts.

Ocular Fibrosis

LPA is in involved in wound healing in the eye. LPA$_1$ and LPA$_3$ receptors are detectable in the normal rabbit corneal epithelial cells, keratocytes and endothelial cells and LPA$_1$ and LPA$_3$ expression are increased in corneal epithelial cells following injury.

LPA and its homologues are present in the aqueous humor and the lacrimal gland fluid of the rabbit eye and these levels are increased in a rabbit corneal injury model.

LPA induces actin stress fiber formation in rabbit corneal endothelial and epithelial cells and promotes contraction corneal fibroblasts. LPA also stimulates proliferation of human retinal pigmented epithelial cells Cardiac Fibrosis LPA is implicated in myocardial infarction and cardiac fibrosis. Serum LPA levels are increased in patients following mycocardial infarction (MI) and LPA stimulates proliferation and collagen production (fibrosis) by rat cardiac fibroblasts. Both LPA$_1$ and LPA$_3$ receptors are highly expressed in human heart tissue.

Treatment of Fibrosis

In one aspect, a compound of Formula (I), or a pharmaceutically acceptable salt or solvate thereof, is used to treat or prevent fibrosis in a mammal. In one aspect, a compound of Formulas (I), or a pharmaceutically acceptable salt or solvate thereof, is used to treat fibrosis of an organ or tissue in a mammal. In one aspect is a method for preventing a fibrosis condition in a mammal, the method comprising administering to the mammal at risk of developing one or more fibrosis conditions a therapeutically effective amount of a compound of Formulas (I), or a pharmaceutically acceptable salt or solvate thereof. In one aspect, the mammal has been exposed to one or more environmental conditions that are known to increase the risk of fibrosis of an organ or tissue. In one aspect, the mammal has been exposed to one or more environmental conditions that are known to increase the risk of lung, liver or kidney fibrosis. In one aspect, the mammal has a genetic predisposition of developing fibrosis of an organ or tissue. In one aspect, a compound of Formula (I), or a pharmaceutically acceptable salt or solvate thereof, is administered to a mammal to prevent or minimize scarring following injury. In one aspect, injury includes surgery.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In one aspect, a mammal suffering from one of the following non-limiting exemplary diseases, disorders, or conditions will benefit from therapy with a compound of Formula (I), or a pharmaceutically acceptable salt or solvate thereof: atherosclerosis, thrombosis, heart disease, vasculitis, formation of scar tissue, restenosis, phlebitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In one aspect, a compound of Formula (I), or a pharmaceutically acceptable salt or solvate thereof, is administered to a mammal with fibrosis of an organ or tissue or with a predisposition of developing fibrosis of an organ or tissue with one or more other agents that are used to treat fibrosis. In one aspect, the one or more agents include corticosteroids. In one aspect, the one or more agents include immunosuppressants. In one aspect, the one or more agents include B-cell antagonists. In one aspect, the one or more agents include uteroglobin.

In one aspect, a compound of Formula (I), or a pharmaceutically acceptable salt or solvate thereof, is used to treat a dermatological disorders in a mammal. The term "dermatological disorder," as used herein refers to a skin disorder. Such dermatological disorders include, but are not limited to, proliferative or inflammatory disorders of the skin such as, atopic dermatitis, bullous disorders, collagenoses, psoriasis, scleroderma, psoriatic lesions, dermatitis, contact dermatitis, eczema, urticaria, rosacea, wound healing, scarring, hypertrophic scarring, keloids, Kawasaki Disease, rosacea, Sjogren-Larsso Syndrome, urticaria. In one aspect, a compound of Formula (I), or a pharmaceutically acceptable salt or solvate thereof, is used to treat systemic sclerosis.

Pain

Since LPA is released following tissue injury, $LPA_1$ plays an important role in the initiation of neuropathic pain. $LPA_1$, unlike $LPA_2$ or $LPA_3$, is expressed in both dorsal root ganglion (DRG) and dorsal root neurons. Using the antisense oligodeoxynucleotide (AS-ODN) for $LPA_1$ and $LPA_1$-null mice, it was found that LPA-induced mechanical allodynia and hyperalgesia is mediated in an LPA-dependent manner. $LPA_1$ and downstream Rho-ROCK activation play a role in the initiation of neuropathic pain signaling. Pretreatment with *Clostridium botulinum* C3 exoenzyme (BoTXC3, Rho inhibitor) or Y-27632 (ROCK inhibitor) completely abolished the allodynia and hyperalgesia in nerve-injured mice. LPA also induced demyelination of the dorsal root, which was prevented by BoTXC3. The dorsal root demyelination by injury was not observed in $LPA_1$-null mice or AS-ODN injected wild-type mice. LPA signaling appears to induce important neuropathic pain markers such as protein kinase Cγ (PKCγ) and a voltage-gated calcium channel α2δ1 subunit (Caα2δ1) in an $LPA_1$ and Rho-dependent manner (M. Inoue, et al., Initiation of neuropathic pain requires lysophosphatidic acid receptor signaling, *Nat. Med.* 10 (2004) 712-718).

In one aspect, a compound of Formula (I), or a pharmaceutically acceptable salt or solvate thereof, is used in the treatment of pain in a mammal. In one aspect, the pain is acute pain or chronic pain. In another aspect, the pain is neuropathic pain.

In one aspect, a compound of Formula (I), or a pharmaceutically acceptable salt or solvate thereof, is used in the treatment of fibromyalgia. In one aspect, fibromyalgia stems from the formation of fibrous scar tissue in contractile (voluntary) muscles. Fibrosis binds the tissue and inhibits blood flow, resulting in pain.

Cancer

Lysophospholipid receptor signaling plays a role in the etiology of cancer. Lysophosphatidic acid (LPA) and its G protein-coupled receptors (GPCRs) $LPA_1$, $LPA_2$, and/or $LPA_3$ play a role in the development of several types of cancers. The initiation, progression and metastasis of cancer involve several concurrent and sequential processes including cell proliferation and growth, survival and anti-apoptosis, migration of cells, penetration of foreign cells into defined cellular layers and/or organs, and promotion of angiogenesis. The control of each of these processes by LPA signaling in physiological and pathophysiological conditions underscores the potential therapeutic usefulness of modulating LPA signaling pathways for the treatment of cancer, especially at the level of the LPA receptors or ATX/lysoPLD. Autotaxin (ATX) is a prometastatic enzyme initially isolated from the conditioned medium of human melanoma cells that stimulates a myriad of biological activities, including angiogenesis and the promotion of cell growth, migration, survival, and differentiation through the production of LPA (*Mol Cancer Ther* 2008; 7(10):3352-62).

LPA signals through its own GPCRs leading to activation of multiple downstream effector pathways. Such downstream effector pathways play a role in cancer. LPA and its GPCRs are linked to cancer through major oncogenic signaling pathways.

LPA contributes to tumorigenesis by increasing motility and invasiveness of cells. LPA has been implicated in the initiation or progression of ovarian cancer. LPA is present at significant concentrations (2-80 µM) in the ascitic fluid of ovarian cancer patients. Ovarian cancer cells constitutively produce increased amounts of LPA as compared to normal ovarian surface epithelial cells, the precursor of ovarian epithelial cancer. Elevated LPA levels are also detected in plasma from patients with early-stage ovarian cancers compared with controls. LPA receptors ($LPA_2$ and $LPA_3$) are also overexpressed in ovarian cancer cells as compared to normal ovarian surface epithelial cells. LPA stimulates Cox-2 expression through transcriptional activation and post-transcriptional enhancement of Cox-2 mRNA in ovarian cancer cells. Prostaglandins produced by Cox-2 have been implicated in a number of human cancers and pharmacological inhibition of Cox-2 activity reduces colon cancer development and decreases the size and number of adenomas in patients with familial adenomatous polyposis. LPA has also been implicated in the initiation or progression of prostate cancer, breast cancer, melanoma, head and neck cancer, bowel cancer (colorectal cancer), thyroid cancer and other cancers (Gardell et al, *Trends in Molecular Medicine*, vol. 12, no. 2, p 65-75, 2006; Ishii et al, *Annu. Rev. Biochem*, 73, 321-354, 2004; Mills et al., *Nat. Rev. Cancer*, 3, 582-591, 2003; Murph et al., *Biochimica et Biophysica Acta*, 1781, 547-557, 2008).

The cellular responses to LPA are mediated through the lysophosphatidic acid receptors. For example, LPA receptors mediate both migration of and invasion by pancreatic cancer cell lines: an antagonist of $LPA_1$ and $LPA_3$ (Ki16425) and $LPA_1$-specific siRNA effectively blocked in vitro migration in response to LPA and peritoneal fluid (ascites) from pancreatic cancer patients; in addition, Ki16425 blocked the LPA-induced and ascites-induced invasion activity of a highly peritoneal metastatic pancreatic cancer cell line (Yamada et al, *J Biol. Chem.*, 279, 6595-6605, 2004).

Colorectal carcinoma cell lines show significant expression of $LPA_1$ mRNA and respond to LPA by cell migration and production of angiogenic factors. Overexpression of LPA receptors has a role in the pathogenesis of thyroid cancer. $LPA_3$ was originally cloned from prostate cancer cells, concordant with the ability of LPA to induce autocrine proliferation of prostate cancer cells.

LPA has stimulatory roles in cancer progression in many types of cancer. LPA is produced from and induces proliferation of prostate cancer cell lines. LPA induces human colon carcinoma DLD1 cell proliferation, migration, adhesion, and secretion of angiogenic factors through $LPA_1$ signaling. In other human colon carcinoma cells lines (HT29 and WiDR), LPA enhances cell proliferation and secretion of angiogenic factors. In other colon cancer cell lines, $LPA_2$ and $LPA_3$ receptor activation results in proliferation of the cells. The genetic or pharmacological manipulation of LPA metabolism, specific blockade of receptor signaling, and/or inhibition of downstream signal transduction pathways, represent approaches for cancer therapies.

It has been reported that LPA and other phospholipids stimulate expression of interleukin-8 (IL-8) in ovarian cancer cell lines. In some embodiments, high concentrations of IL-8 in ovarian cancer correlate with poor initial response to chemotherapy and with poor prognosis, respectively. In animal models, expression of IL-8 and other growth factors such as vascular endothelial growth factor (VEGF) is associated with increased tumorigenicity, ascites formation, angiogenesis, and invasiveness of ovarian cancer cells. In some aspects, IL-8 is an important modulator of cancer progression, drug resistance, and prognosis in ovarian cancer. In some embodiments, a compound of Formula (I) inhibits or reduces IL-8 expression in ovarian cancer cell lines.

In one aspect, a compound of Formula (I), or a pharmaceutically acceptable salt or solvate thereof, is used in the treatment of cancer. In one aspect, a compound of Formula (I), or a pharmaceutically acceptable salt or solvate thereof, is used in the treatment of malignant and benign proliferative disease. In one aspect, a compound of Formula (I), or a pharmaceutically acceptable salt or solvate thereof, is used to prevent or reduce proliferation of tumor cells, invasion and metastasis of carcinomas, pleural mesothelioma (Yamada, *Cancer Sci.*, 2008, 99(8), 1603-1610) or peritoneal mesothelioma, cancer pain, bone metastases (Boucharaba et al, *J. Clin. Invest.*, 2004, 114(12), 1714-1725; Boucharaba et al, *Proc. Nat. acad. Sci.*, 2006, 103(25) 9643-9648). In one aspect is a method of treating cancer in a mammal, the method comprising administering to the mammal a compound of Formula (I), or a pharmaceutically acceptable salt or solvate thereof, and a second therapeutic agent, wherein the second therapeutic agent is an anti-cancer agent.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglubulinemia, Wilms tumor.

The increased concentrations of LPA and vesicles in ascites from ovarian cancer patients and breast cancer effussions indicate that it could be an early diagnostic marker, a prognostic indicator or an indicator of response to therapy (Mills et al, *Nat. Rev. Cancer.*, 3, 582-591, 2003; Sutphen et al., *Cancer Epidemiol. Biomarkers Prev.* 13, 1185-1191, 2004). LPA concentrations are consistently higher in ascites samples than in matched plasma samples.

Respiratory and Allergic Disorders

In one aspect, LPA is a contributor to the pathogenesis of respiratory diseases. In one aspect the respiratory disease is asthma. Proinflammatory effects of LPA include degranulation of mast cells, contraction of smooth-muscle cells and release of cytokines from dendritic cells. Airway smooth muscle cells, epithelial cells and lung fibroblasts all show responses to LPA. LPA induces the secretion of IL-8 from human bronchial epithelial cells. IL-8 is found in increased concentrations in BAL fluids from patients with asthma, chronic obstructive lung disease, pulmonary sarcoidosis and acute respiratory distress syndrome and Il-8 has been shown to exacerbate airway inflammation and airway remodeling of asthmatics. $LPA_1$, $LPA_2$ and $LPA_3$ receptors have all been shown to contribute to the LPA-induced IL-8 production. Studies cloning multiple GPCRs that are activated by LPA allowed the demonstration of the presence of mRNA for the $LPA_1$, $LPA_2$ and $LPA_3$ in the lung (J. J. A. Contos, et al., *Mol. Pharmacol.* 58, 1188-1196, 2000).

The release of LPA from platelets activated at a site of injury and its ability to promote fibroblast proliferation and contraction are features of LPA as a mediator of wound repair. In the context of airway disease, asthma is an inflammatory disease where inappropriate airway "repair" processes lead to structural "remodeling" of the airway. In asthma, the cells of the airway are subject to ongoing injury due to a variety of insults, including allergens, pollutants, other inhaled environmental agents, bacteria and viruses, leading to the chronic inflammation that characterizes asthma.

In one aspect, in the asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. In one aspect, LPA contributes to these structural changes in the airway. In one aspect, LPA is involved in acute airway hyperresponsiveness in asthma. The lumen of the remodeled asthmatic airway is narrower due to the thickening of the airway wall, thus decreasing airflow. In one aspect, LPA contributes to the long-term structural remodeling and the acute hyperresponsiveness of the asthmatic airway. In one aspect, LPA contributes to the hyper-responsiveness that is a primary feature of acute exacerbations of asthma.

In addition to the cellular responses mediated by LPA, several of the LPA signaling pathway components leading to these responses are relevant to asthma. EGF receptor upregulation is induced by LPA and is also seen in asthmatic airways (M. Amishima, et al., *Am. J. Respir. Crit. Care Med.* 157, 1907-1912, 1998). Chronic inflammation is a contributor to asthma, and several of the transcription factors that are activated by LPA are known to be involved in inflammation (Ediger et al., *Eur Respir J* 21:759-769, 2003).

In one aspect, the fibroblast proliferation and contraction and extracellular matrix secretion stimulated by LPA contributes to the fibroproliferative features of other airway diseases, such as the peribronchiolar fibrosis present in chronic bronchitis, emphysema, and interstitial lung disease. Emphysema is also associated with a mild fibrosis of the alveolar wall, a feature which is believed to represent an attempt to repair alveolar damage. In another aspect, LPA plays a role in the fibrotic interstitial lung diseases and obliterative bronchiolitis, where both collagen and myofibroblasts are increased. In another aspect, LPA is involved in several of the various syndromes that constitute chronic obstructive pulmonary disease.

Administration of LPA in vivo induces airway hyperresponsiveness, itch-scratch responses, infiltration and activation of eosinophils and neutrophils, vascular remodeling, and nociceptive flexor responses. LPA also induces histamine release from mouse and rat mast cells. In an acute allergic reaction, histamine induces various responses, such as contraction of smooth muscle, plasma exudation, and mucus production. Plasma exudation is important in the airway, because the leakage and subsequent airway-wall edema contribute to the development of airway hyperresponsiveness. Plasma exudation progresses to conjunctival swelling in ocular allergic disorder and nasal blockage in allergic rhinitis (Hashimoto et al., *J Pharmacol Sci* 100, 82-87, 2006). In one aspect, plasma exudation induced by LPA is mediated by histamine release from mast cells via one or more LPA receptors. In one aspect, the LPA receptor(s) include $LPA_1$ and/or $LPA_3$. In one aspect, a compound of Formula (I), or a pharmaceutically acceptable salt or solvate thereof, is used in the treatment of various allergic disorders in a mammal. In one aspect, a compound of Formula (I), or a pharmaceutically acceptable salt or solvate thereof, is used in the treatment of respiratory diseases, disorders or conditions in a mammal. In one aspect, a compound of Formula (I), or a pharmaceutically acceptable salt or solvate thereof, is used in the treatment of asthma in a mammal. In one aspect, a compound of Formula (I), or a pharmaceutically acceptable salt or solvate thereof, is used in the treatment of chronic asthma in a mammal.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

In one aspect, presented herein is the use of a compound of Formula (I), or a pharmaceutically acceptable salt or solvate thereof, in the treatment or prevention of chronic obstructive pulmonary disease in a mammal comprising administering to the mammal at least once an effective amount of at least one compound of Formula (I), or a pharmaceutically acceptable salt or solvate thereof. In addition, chronic obstructive pulmonary disease includes, but is not limited to, chronic bronchitis or emphysema, pulmonary hypertension, interstitial lung fibrosis and/or airway inflammation, and cystic fibrosis.

Nervous System

The nervous system is a major locus for $LPA_1$ expression; there it is spatially and temporally regulated throughout brain development. Oligodendrocytes, the myelinating cells in the central nervous system (CNS), express $LPA_1$ in mammals. In addition, Schwann cells, the myelinating cells of the peripheral nervous system, also express $LPA_1$, which is involved in regulating Schwann cell survival and morphology. These observations identify important functions for receptor-mediated LPA signaling in neurogenesis, cell survival, and myelination.

Exposure of peripheral nervous system cell lines to LPA produces a rapid retraction of their processes resulting in cell rounding, which was, in part, mediated by polymerization of the actin cytoskeleton. In one aspect, LPA causes neuronal degeneration under pathological conditions when the blood-brain barrier is damaged and serum components leak into the brain (Moolenaar, Curr. Opin. Cell Biol. 7:203-10, 1995). Immortalized CNS neuroblast cell lines from the cerebral cortex also display retraction responses to LPA exposure through Rho activation and actomyosin interactions. In one aspect, LPA is associated with post-ischemic neural damage (J. Neurochem. 61, 340, 1993; J. Neurochem., 70:66, 1998).

In one aspect, provided is a compound of Formula (I), or a pharmaceutically acceptable salt or solvate thereof, for use in the treatment or prevention of a nervous system disorder in a mammal. The term "nervous system disorder," as used herein, refers to conditions that alter the structure or function of the brain, spinal cord or peripheral nervous system, including but not limited to Alzheimer's Disease, cerebral edema, cerebral ischemia, stroke, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica.

In one aspect, provided is a compound of Formula (I), or a pharmaceutically acceptable salt or solvate thereof, for use in the treatment or prevention of a CNS disorder in a mammal. CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

Cardiovascular Disorders

Cardiovascular phenotypes observed after targeted deletion of lysophospholipid receptors reveal important roles for lysophospholipid signaling in the development and maturation of blood vessels, formation of atherosclerotic plaques and maintenance of heart rate (Ishii, I. et al. Annu. Rev. Biochem. 73, 321-354, 2004). Angiogenesis, the formation of new capillary networks from pre-existing vasculature, is normally invoked in wound healing, tissue growth and myocardial angiogenesis after ischemic injury. Peptide growth factors (e.g. vascular endothelial growth factor (VEGF)) and lysophospholipids control coordinated proliferation, migration, adhesion, differentiation and assembly of vascular endothelial cells (VECs) and surrounding vascular smooth-muscle cells (VSMCs). In one aspect, dysregulation of the processes mediating angiogenesis leads to atherosclerosis, hypertension, tumor growth, rheumatoid arthritis and diabetic retinopathy (Osborne, N. and Stainier, D. Y. Annu. Rev. Physiol. 65, 23-43, 2003).

Downstream signaling pathways evoked by lysophospholipid receptors include Rac-dependent lamellipodia formation (e.g. $LPA_1$) and Rho-dependent stress-fiber formation (e.g. $LPA_1$), which is important in cell migration and adhesion. Dysfunction of the vascular endothelium can shift the balance from vasodilatation to vasoconstriction and lead to hypertension and vascular remodeling, which are risk factors for atherosclerosis (Maguire, J. J. et al., Trends Pharmacol. Sci. 26, 448-454, 2005).

LPA contributes to both the early phase (barrier dysfunction and monocyte adhesion of the endothelium) and the late phase (platelet activation and intra-arterial thrombus formation) of atherosclerosis, in addition to its overall progression. In the early phase, LPA from numerous sources accumulates in lesions and activates its cognate GPCRs ($LPA_1$ and $LPA_3$) expressed on platelets (Siess, W. Biochim. Biophys. Acta 1582, 204-215, 2002; Rother, E. et al. Circulation 108, 741-747, 2003). This triggers platelet shape change and aggregation, leading to intra-arterial thrombus formation and, potentially, myocardial infarction and stroke. In support of its atherogenic activity, LPA can also be a mitogen and motogen to VSMCs and an activator of endothelial cells and macrophages. In one aspect, mammals with cardiovascular disease benefit from LPA receptor antagonists that prevent thrombus and neointima plaque formation.

In one aspect, a compound of Formula (I), or a pharmaceutically acceptable salt or solvate thereof, is used to treat or prevent cardiovascular disease in mammal.

The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In one aspect, provided herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of Formula (I), or a pharmaceutically acceptable salt or solvate thereof, or pharmaceutical composition or medicament which includes a compound of Formula (I), or a pharmaceutically acceptable salt or solvate thereof.

In one aspect, provided herein are methods for reducing cardiac reperfusion injury following myocardial ischemia and/or endotoxic shock comprising administering at least once to the mammal an effective amount of at least one compound of Formula (I), or a pharmaceutically acceptable salt or solvate thereof.

In one aspect, provided herein are methods for reducing the constriction of blood vessels in a mammal comprising administering at least once to the mammal an effective amount of at least one compound of Formula (I), or a pharmaceutically acceptable salt or solvate thereof.

In one aspect, provided herein are methods for lowering or preventing an increase in blood pressure of a mammal comprising administering at least once to the mammal an effective amount of at least one compound of Formula (I), or a pharmaceutically acceptable salt or solvate thereof.

Inflammation

LPA has been shown to regulate immunological responses by modulating activities/functions of immune cells such as T-/B-lymphocytes and macrophages. In activated T cells, LPA activates IL-2 production/cell proliferation through $LPA_1$ (Gardell et al, *TRENDS in Molecular Medicine* Vol. 12 No. 2 Feb. 2006). Expression of LPA-induced inflammatory response genes is mediated by $LPA_1$ and $LPA_3$ (*Biochem Biophys Res Commun.* 363(4):1001-8, 2007). In addition, LPA modulates the chemotaxis of inflammatory cells (*Biochem Biophys Res Commun.*, 1993, 15; 193(2), 497). The proliferation and cytokine-secreting activity in response to LPA of immune cells (*J. Imuunol.* 1999, 162, 2049), platelet aggregation activity in response to LPA, acceleration of migration activity in monocytes, activation of NF-κB in fibroblast, enhancement of fibronectin-binding to the cell surface, and the like are known. Thus, LPA is associated with various inflammatory/immune diseases.

In one aspect, a compound of Formula (I), or a pharmaceutically acceptable salt or solvate thereof, is used to treat or prevent inflammation in a mammal. In one aspect, antagonists of $LPA_1$ and/or $LPA_3$ find use in the treatment or prevention of inflammatory/immune disorders in a mammal. In one aspect, the antagonist of $LPA_1$ is a compound of Formula (I), or a pharmaceutically acceptable salt or solvate thereof.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Other Diseases, Disorders or Conditions

In accordance with one aspect, are methods for treating, preventing, reversing, halting or slowing the progression of LPA-dependent or LPA-mediated diseases or conditions once it becomes clinically evident, or treating the symptoms associated with or related to LPA-dependent or LPA-mediated diseases or conditions, by administering to the mammal a compound of Formula (I), or a pharmaceutically acceptable salt or solvate thereof. In certain embodiments, the subject already has a LPA-dependent or LPA-mediated disease or condition at the time of administration, or is at risk of developing a LPA-dependent or LPA-mediated disease or condition.

In certain aspects, the activity of $LPA_1$ in a mammal is directly or indirectly modulated by the administration of (at least once) a therapeutically effective amount of at least one compound of Formula (I), or a pharmaceutically acceptable salt or solvate thereof. Such modulation includes, but is not limited to, reducing and/or inhibiting the activity of $LPA_1$. In additional aspects, the activity of LPA in a mammal is directly or indirectly modulated, including reducing and/or inhibiting, by the administration of (at least once) a therapeutically effective amount of at least one compound of Formula (I), or a pharmaceutically acceptable salt or solvate thereof. Such modulation includes, but is not limited to, reducing and/or inhibiting the amount and/or activity of a LPA receptor. In one aspect, the LPA receptor is $LPA_1$.

In one aspect, LPA has a contracting action on bladder smooth muscle cell isolated from bladder, and promotes growth of prostate-derived epithelial cell (*J. Urology*, 1999, 162, 1779-1784; *J. Urology*, 2000, 163, 1027-1032). In another aspect, LPA contracts the urinary tract and prostate in vitro and increases intraurethral pressure in vivo (WO 02/062389).

In certain aspects, are methods for preventing or treating eosinophil and/or basophil and/or dendritic cell and/or neutrophil and/or monocyte and/or T-cell recruitment comprising administering at least once to the mammal an effective amount of at least one compound of Formula (I), or a pharmaceutically acceptable salt or solvate thereof.

In certain aspects, are methods for the treatment of cystitis, including, e.g., interstitial cystitis, comprising administering at least once to the mammal a therapeutically effective amount of at least one compound of Formula (I), or a pharmaceutically acceptable salt or solvate thereof.

In accordance with one aspect, methods described herein include the diagnosis or determination of whether or not a patient is suffering from a LPA-dependent or LPA-mediated disease or condition by administering to the subject a therapeutically effective amount of a compound of Formula (I), or a pharmaceutically acceptable salt or solvate thereof, and determining whether or not the patient responds to the treatment.

In one aspect provided herein are compounds of Formula (I), pharmaceutically acceptable salts, pharmaceutically acceptable prodrugs, and pharmaceutically acceptable solvates thereof, which are antagonists of $LPA_1$, and are used to treat patients suffering from one or more LPA-dependent or LPA-mediated conditions or diseases, including, but not limited to, lung fibrosis, kidney fibrosis, liver fibrosis, scarring, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions. In some embodiments, LPA-dependent conditions or diseases include those wherein an absolute or relative excess of LPA is present and/or observed.

In any of the aforementioned aspects the LPA-dependent or LPA-mediated diseases or conditions include, but are not limited to, organ fibrosis, asthma, allergic disorders, chronic obstructive pulmonary disease, pulmonary hypertension, lung or pleural fibrosis, peritoneal fibrosis, arthritis, allergy, cancer, cardiovascular disease, ult respiratory distress syndrome, myocardial infarction, aneurysm, stroke, and cancer.

In one aspect, a compound of Formula (I), or a pharmaceutically acceptable salt or solvate thereof, is used to improve the corneal sensitivity decrease caused by corneal operations such as laser-assisted in situ keratomileusis (LASIK) or cataract operation, corneal sensitivity decrease caused by corneal degeneration, and dry eye symptom caused thereby.

In one aspect, presented herein is the use of a compound of Formula (I), or a pharmaceutically acceptable salt or solvate thereof, in the treatment or prevention of ocular inflammation and allergic conjunctivitis, vernal keratoconjunctivitis, and papillary conjunctivitis in a mammal comprising administering at least once to the mammal an effective amount of at least one compound of Formula (I), or a pharmaceutically acceptable salt or solvate thereof.

In one aspect, presented herein is the use of a compound of Formula (I), or a pharmaceutically acceptable salt or solvate thereof, in the treatment or prevention of Sjogren disease or inflammatory disease with dry eyes in a mammal comprising administering at least once to the mammal an effective amount of at least one compound of Formula (I), or a pharmaceutically acceptable salt or solvate thereof.

In one aspect, LPA and LPA receptors (e.g. $LPA_1$) are involved in the pathogenesis of osteoarthritis (Kotani et al, *Hum. Mol. Genet.*, 2008, 17, 1790-1797). In one aspect, presented herein is the use of a compound of Formula (I), or a pharmaceutically acceptable salt or solvate thereof, in the treatment or prevention of osteoarthritis in a mammal comprising administering at least once to the mammal an effective amount of at least one compound of Formula (I), or a pharmaceutically acceptable salt or solvate thereof.

In one aspect, LPA receptors (e.g. $LPA_1$, $LPA_3$) contribute to the pathogenesis of rheumatoid arthritis (Zhao et al, *Mol. Pharmacol.*, 2008, 73(2), 587-600). In one aspect, presented herein is the use of a compound of Formula (I), or a pharmaceutically acceptable salt or solvate thereof, in the treatment or prevention of rheumatoid arthritis in a mammal comprising administering at least once to the mammal an effective amount of at least one compound of Formula (I), or a pharmaceutically acceptable salt or solvate thereof.

In one aspect, LPA receptors (e.g. $LPA_1$) contribute to adipogenesis. (Simon et al, *J. Biol. Chem.*, 2005, vol. 280, no. 15, p. 14656). In one aspect, presented herein is the use of a compound of Formula (I), or a pharmaceutically acceptable salt or solvate thereof, in the promotion of adipose tissue formation in a mammal comprising administering at least once to the mammal an effective amount of at least one compound of Formula (I), or a pharmaceutically acceptable salt or solvate thereof.

a. In Vitro Assays

The effectiveness of compounds of the present invention as $LPA_1$ inhibitors can be determined in an $LPA_1$ functional antagonist assay as follows:

Chinese hamster ovary cells overexpressing human $LPA_1$ were plated overnight (15,000 cells/well) in poly-D-lysine coated 384-well microplates (Greiner bio-one, Cat #781946) in DMEM/F12 medium (Gibco, Cat #11039). Following overnight culture, cells were loaded with calcium indicator dye (AAT Bioquest Inc, Cat #34601) for 30 minutes at 37° C. The cells were then equilibrated to room temperature for 30 minutes before the assay. Test compounds solubilized in DMSO were transferred to 384 well non-binding surface plates (Corning, Cat #3575) using the Labcyte Echo acoustic dispense and diluted with assay buffer [1×HBSS with calcium/magnesium (Gibco Cat #14025-092), 20 mM HEPES (Gibco Cat #15630-080) and 0.1% fatty acid free BSA (Sigma Cat #A9205)] to a final concentration of 0.5% DMSO. Diluted compounds were added to the cells by FDSS6000 (Hamamatsu) at final concentrations ranging from 0.08 nM to 5 μM. and were then incubated for 20 min at room temperature at which time LPA (Avanti Polar Lipids Cat #857130C) was added at final concentrations of 10 nM to stimulate the cells.

The compound $IC_{50}$ value was defined as the concentration of test compound which inhibited 50% of the calcium flux induced by LPA alone. $IC_{50}$ values were determined by fitting data to a 4-parameter logistic equation (GraphPad Prism, San Diego Calif.).

b. In Vivo Assays

LPA Challenge with Plasma Histamine Evaluation.

Compound is dosed orally p.o. 2 hours to CD-1 female mice prior to the LPA challenge. The mice are then dosed via tail vein (IV) with 0.15 mL of LPA in 0.1% BSA/PBS (2 μg/μL). Exactly 2 minutes following the LPA challenge, the mice are euthanized by decapitation and the trunk blood is collected. These samples are collectively centrifuged and individual 75 μL samples are frozen at −20° C. until the time of the histamine assay.

The plasma histamine analysis was run by standard EIA (Enzyme Immunoassay) methods. Plasma samples were thawed and diluted 1:30 in 0.1% BSA in PBS. The EIA protocol for histamine analysis as outlined by the manufacturer was followed (Histamine EIA, Oxford Biomedical Research, EA #31).

The LPA used in the assay is formulated as follows: LPA (1-oleoyl-2-hydroxy-sn-glycero-3-phosphate (sodium salt), 857130P, Avanti Polar Lipids) is prepared in 0.1% BSA/PBS for total concentration of 2 μg/L. 13 mg of LPA is weighed and 6.5 mL 0.1% BSA added, vortexed and sonicated for ~1 hour until a clear solution is achieved.

V. Pharmaceutical Compositions, Formulations and Combinations

In some embodiments, provided is a pharmaceutical composition comprising a therapeutically effective amount of a compound of Formula (I), or a pharmaceutically acceptable salt or solvate thereof. In some embodiments, the pharmaceutical composition also contains at least one pharmaceutically acceptable inactive ingredient.

In some embodiments, provided is a pharmaceutical composition comprising a therapeutically effective amount of a compound of Formula (I), or a pharmaceutically acceptable salt or solvate thereof, and at least one pharmaceutically acceptable inactive ingredient. In one aspect, the pharmaceutical composition is formulated for intravenous injection, subcutaneous injection, oral administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the pharmaceutical composition further comprises one or more additional therapeutically active agents selected from: corticosteroids (e.g., dexamethasone or fluticasone), immunosuppressants (e.g., tacrolimus & pimecrolimus), analgesics, anti-cancer agent, anti-inflammatories, chemokine receptor antagonists, bronchodilators, leukotriene receptor antagonists (e.g., montelukast or zafirlukast), leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines (e.g., loratidine), mucolytics, anticholinergics, antitussives, expectorants, anti-infectives (e.g., fusidic acid, particularly for treatment of atopic dermatitis), anti-fungals (e.g., clotriazole, particularly for atopic dermatitis), anti-IgE antibody therapies (e.g., omalizumab), β-2 adrenergic agonists (e.g., albuterol or salmeterol), other PGD2 antagonists acting at other receptors such as DP antagonists, PDE4 inhibitors (e.g., cilomilast), drugs that modulate cytokine production, e.g., TACE inhibitors, drugs that modulate activity of Th2 cytokines IL-4 & IL-5 (e.g., blocking monoclonal antibodies & soluble receptors), PPARγ agonists (e.g., rosiglitazone and pioglitazone), 5-lipoxygenase inhibitors (e.g., zileuton).

In some embodiments, the pharmaceutical composition further comprises one or more additional anti-fibrotic agents selected from pirfenidone, nintedanib, thalidomide, carlumab, FG-3019, fresolimumab, interferon alpha, lecithinized superoxide dismutase, simtuzumab, tanzisertib, tralokinumab, hu3G9, AM-152, IFN-gamma-1b, IW-001, PRM-151, PXS-25, pentoxifylline/N-acetyl-cysteine, pentoxifylline/vitamin E, salbutamol sulfate, [Sar9,Met(O2)11]-Substance P, pentoxifylline, mercaptamine bitartrate, obeticholic acid, aramchol, GFT-505, eicosapentaenoic acid ethyl ester, metformin, metreleptin, muromonab-CD3, oltipraz, IMM-124-E, MK-4074, PX-102, RO-5093151. In some embodiments, provided is a method comprising administering a compound of Formula (I), or a pharmaceutically acceptable salt or solvate thereof, to a human with a LPA-dependent or LPA-mediated disease or condition. In some embodiments, the human is already being administered one or more additional therapeutically active agents other than a compound of Formula (I), or a pharmaceutically acceptable salt or solvate thereof. In some embodiments, the method further comprises administering one or more additional therapeutically active agents other than a compound of Formula (I), or a pharmaceutically acceptable salt or solvate thereof.

In some embodiments, the one or more additional therapeutically active agents other than a compound of Formula (I), or a pharmaceutically acceptable salt or solvate thereof, are selected from: corticosteroids (e.g., dexamethasone or fluticasone), immunosuppresants (e.g., tacrolimus & pimecrolimus), analgesics, anti-cancer agent, anti-inflammatories, chemokine receptor antagonists, bronchodilators, leukotriene receptor antagonists (e.g., montelukast or zafirlukast), leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines (e.g., loratidine), mucolytics, anticholinergics, antitussives, expectorants, anti-infectives (e.g., fusidic acid, particularly for treatment of atopic dermatitis), anti-fungals (e.g., clotriazole, particularly for atopic dermatitis), anti-IgE antibody therapies (e.g., omalizumab), β-2 adrenergic agonists (e.g., albuterol or salmeterol), other PGD2 antagonists acting at other receptors such as DP antagonists, PDE4 inhibitors (e.g., cilomilast), drugs that modulate cytokine production, e.g., TACE inhibitors, drugs that modulate activity of Th2 cytokines IL-4 & IL-5 (e.g., blocking monoclonal antibodies & soluble receptors), PPARγ agonists (e.g., rosiglitazone and pioglitazone), 5-lipoxygenase inhibitors (e.g., zileuton).

In some embodiments, the one or more additional therapeutically active agents other than a compound of Formula (I), or a pharmaceutically acceptable salt or solvate thereof, are other anti-fibrotic agents selected from pirfenidone, nintedanib, thalidomide, carlumab, FG-3019, fresolimumab, interferon alpha, lecithinized superoxide dismutase, simtuzumab, tanzisertib, tralokinumab, hu3G9, AM-152, IFN-gamma-1b, IW-001, PRM-151, PXS-25, pentoxifylline/N-acetyl-cysteine, pentoxifylline/vitamin E, salbutamol sulfate, [Sar9,Met(O2)11]-Substance P, pentoxifylline, mercaptamine bitartrate, obeticholic acid, aramchol, GFT-505, eicosapentyl ethyl ester, metformin, metreleptin, muromonab-CD3, oltipraz, IMM-124-E, MK-4074, PX-102, RO-5093151.

In some embodiments, the one or more additional therapeutically active agents other than a compound of Formula (I), or a pharmaceutically acceptable salt or solvate thereof, are selected from ACE inhibitors, ramipril, AII antagonists, irbesartan, anti-arrythmics, dronedarone, PPARα activators, PPARγ activators, pioglitazone, rosiglitazone, prostanoids, endothelin receptor antagonists, elastase inhibitors, calcium antagonists, beta blockers, diuretics, aldosterone receptor antagonists, eplerenone, renin inhibitors, rho kinase inhibitors, soluble guanylate cyclase (sGC) activators, sGC sensitizers, PDE inhibitors, PDE5 inhibitors, NO donors, digitalis drugs, ACE/NEP inhibitors, statins, bile acid reuptake inhibitors, PDGF antagonists, vasopressin antagonists, aquaretics, NHE1 inhibitors, Factor Xa antagonists, Factor XIIIa antagonists, anticoagulants, anti-thrombotics, platelet inhibitors, profibroltics, thrombin-activatable fibrinolysis inhibitors (TAFI), PAI-1 inhibitors, coumarins, heparins, thromboxane antagonists, serotonin antagonists, COX inhibitors, aspirin, therapeutic antibodies, GPIIb/IIIa antagonists, ER antagonists, SERMs, tyrosine kinase inhibitors, RAF kinase inhibitors, p38 MAPK inhibitors, pirfenidone, multi-kinase inhibitors, nintedanib, sorafenib.

In some embodiments, the one or more additional therapeutically active agents other than a compound of Formula (I), or a pharmaceutically acceptable salt or solvate thereof, are selected from Gremlin-1 mAb, PA1-1 mAb, Promedior (PRM-151; recombinant human Pentraxin-2); FGF21, TGFβ antagonists, αvβ6 & αvβ pan-antagonists; FAK inhibitors, TG2 inhibitors, LOXL2 inhibitors, NOX4 inhibitors, MGAT2 inhibitors, GPR120 agonists.

Pharmaceutical formulations described herein are administrable to a subject in a variety of ways by multiple administration routes, including but not limited to, oral, parenteral (e.g., intravenous, subcutaneous, intramuscular), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compound of Formula (I), or a pharmaceutically acceptable salt or solvate thereof, is administered orally.

In some embodiments, the compound of Formula (I), or a pharmaceutically acceptable salt or solvate thereof, is administered topically. In such embodiments, the compound of Formula (I), or a pharmaceutically acceptable salt or solvate thereof, is formulated into a variety of topically administrable compositions, such as solutions, suspensions, lotions, gels, pastes, shampoos, scrubs, rubs, smears, medicated sticks, medicated bandages, balms, creams or ointments. Such pharmaceutical compounds can contain solubilizers, stabilizers, tonicity enhancing agents, buffers and preservatives. In one aspect, the compound of Formula (I), or a pharmaceutically acceptable salt or solvate thereof, is administered topically to the skin.

In another aspect, the compound of Formula (I), or a pharmaceutically acceptable salt or solvate thereof, is administered by inhalation. In one embodiment, the compound of Formula (I), or a pharmaceutically acceptable salt or solvate thereof, is administered by inhalation that directly targets the pulmonary system.

In another aspect, the compound of Formula (I), or a pharmaceutically acceptable salt or solvate thereof, is formulated for intranasal administration. Such formulations include nasal sprays, nasal mists, and the like.

In another aspect, the compound of Formula (I), or a pharmaceutically acceptable salt or solvate thereof, is formulated as eye drops.

In another aspect is the use of a compound of Formula (I), or a pharmaceutically acceptable salt or solvate thereof, in the manufacture of a medicament for treating a disease, disorder or conditions in which the activity of at least one LPA receptor contributes to the pathology and/or symptoms of the disease or condition. In one embodiment of this aspect, the LPA is selected from $LPA_1$, $LPA_2$, $LPA_3$, $LPA_4$, $LPA_5$ and $LPA_6$. In one aspect, the LPA receptor is $LPA_1$. In one aspect, the disease or condition is any of the diseases or conditions specified herein.

In any of the aforementioned aspects are further embodiments in which: (a) the effective amount of the compound of Formula (I), or a pharmaceutically acceptable salt or solvate thereof, is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of inhibiting the physiological activity of LPA in a mammal comprising administering a therapeutically effective amount of a compound of Formula (I) or a pharmaceutically acceptable salt or solvate thereof to the mammal in need thereof.

In one aspect, provided is a medicament for treating a LPA-dependent or LPA-mediated disease or condition in a mammal comprising a therapeutically effective amount of a compound of Formula (I), or a pharmaceutically acceptable salt or solvate thereof.

In some cases disclosed herein is the use of a compound of Formula (I), or a pharmaceutically acceptable salt or solvate thereof, in the manufacture of a medicament for the treatment of a LPA-dependent or LPA-mediated disease or condition.

In some cases disclosed herein is the use of a compound of Formula (I), or a pharmaceutically acceptable salt or solvate thereof, in the treatment or prevention of a LPA-dependent or LPA-mediated disease or condition.

In one aspect, is a method for treating or preventing a LPA-dependent or LPA-mediated disease or condition in a mammal comprising administering a therapeutically effective amount of a compound of Formula (I), or a pharmaceutically acceptable salt or solvate thereof.

In one aspect, LPA-dependent or LPA-mediated diseases or conditions include, but are not limited to, fibrosis of organs or tissues, scarring, liver diseases, dermatological conditions, cancer, cardiovascular disease, respiratory diseases or conditions, inflammatory disease, gastrointestinal tract disease, renal disease, urinary tract-associated disease, inflammatory disease of lower urinary tract, dysuria, frequent urination, pancreas disease, arterial obstruction, cerebral infarction, cerebral hemorrhage, pain, peripheral neuropathy, and fibromyalgia.

In one aspect, the LPA-dependent or LPA-mediated disease or condition is a respiratory disease or condition. In some embodiments, the respiratory disease or condition is asthma, chronic obstructive pulmonary disease (COPD), pulmonary fibrosis, pulmonary arterial hypertension or acute respiratory distress syndrome.

In some embodiments, the LPA-dependent or LPA-mediated disease or condition is selected from idiopathic pulmonary fibrosis; other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Duputren disease, keloids, cutaneous fibrosis; cutaneous scleroderma; spinal cord injury/fibrosis; myelofibrosis; vascular restenosis; atherosclerosis; arteriosclerosis; Wegener's granulomatosis; Peyronie's disease, chronic lymphocytic leukemia, tumor metastasis, transplant organ rejection, endometriosis, neonatal respiratory distress syndrome and neuropathic pain.

In one aspect, the LPA-dependent or LPA-mediated disease or condition is described herein.

In one aspect, provided is a method for the treatment or prevention of organ fibrosis in a mammal comprising administering a therapeutically effective amount of a compound of Formula (I) or a pharmaceutically acceptable salt or solvate thereof to a mammal in need thereof.

In one aspect, the organ fibrosis comprises lung fibrosis, renal fibrosis, or hepatic fibrosis.

In one aspect, provided is a method of improving lung function in a mammal comprising administering a therapeutically effective amount of a compound of Formula (I), or a pharmaceutically acceptable salt or solvate thereof to the mammal in need thereof. In one aspect, the mammal has been diagnosed as having lung fibrosis.

In one aspect, compounds disclosed herein are used to treat idiopathic pulmonary fibrosis (usual interstitial pneumonia) in a mammal.

In some embodiments, compounds disclosed herein are used to treat diffuse parenchymal interstitial lung diseases in mammal: iatrogenic drug induced, occupational/environmental (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, Hermansky-Pudlak Syndrome, Tuberous sclerosis, neurofibromatosis, metabolic storage disorders, familial interstitial lung disease.

In some embodiments, compounds disclosed herein are used to treat post-transplant fibrosis associated with chronic rejection in a mammal: Bronchiolitis obliterans for lung transplant.

In some embodiments, compounds disclosed herein are used to treat cutaneous fibrosis in a mammal: cutaneous scleroderma, Dupuytren disease, keloids.

In one aspect, compounds disclosed herein are used to treat hepatic fibrosis with or without cirrhosis in a mammal: toxic/drug induced (hemochromatosis), alcoholic liver disease, viral hepatitis (hepatitis B virus, hepatitis C virus, HCV), nonalcoholic liver disease (NAFLD, NASH), metabolic and auto-immune disease.

In one aspect, compounds disclosed herein are used to treat renal fibrosis in a mammal: tubulointerstitium fibrosis, glomerular sclerosis.

In any of the aforementioned aspects involving the treatment of LPA dependent diseases or conditions are further embodiments comprising administering at least one additional agent in addition to the administration of a compound having the structure of Formula (I), or a pharmaceutically acceptable salt or solvate thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

In some embodiments, compounds provided herein are used as antagonists of at least one LPA receptor. In some embodiments, compounds provided herein are used for inhibiting the activity of at least one LPA receptor or for the treatment of a disease or condition that would benefit from inhibition of the activity of at least one LPA receptor. In one aspect, the LPA receptor is $LPA_1$.

In other embodiments, compounds provided herein are used for the formulation of a medicament for the inhibition of $LPA_1$ activity.

Articles of manufacture, which include packaging material, a compound of Formula (I), or a pharmaceutically acceptable salt or solvate thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of at least one LPA receptor, or for the treatment, prevention or amelioration of one or more symptoms of a disease or condition that would benefit from inhibition of the activity of at least one LPA receptor, are provided.

VI. General Synthesis Including Schemes

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, Fourth Edition, Wiley-Interscience (2006)).

The compounds of Formula (I) may be prepared by the exemplary processes described in the following schemes and working examples, as well as relevant published literature procedures that are used by one skilled in the art. Exemplary reagents and procedures for these reactions appear herein after and in the working examples. Protection and deprotection in the processes below may be carried out by procedures generally known in the art (see, for example, Wuts, P. G. M., *Greene's Protective Groups in Organic Synthesis*, 5th Edition, Wiley (2014)). General methods of organic synthesis and functional group transformations are found in: Trost, B. M. et al., Eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*. 7th Edition, Wiley, New York, N.Y. (2013); Katritzky, A. R. et al., Eds., *Comprehensive Organic Functional Group Transformations II*, 2nd Edition, Elsevier Science Inc., Tarrytown, N.Y. (2004); Larock, R. C., *Comprehensive Organic Transformations*, 2$^{nd}$ Edition, Wiley-VCH, New York, N.Y. (1999), and references therein.

Scheme 1 describes the synthesis of pyrazole-azine aryl (heteroaryl)cyclohexyl acids 14. A pyrazole 5-carboxylic acid 1 is reduced to the corresponding pyrazole 5-methanol (via a 2-step procedure via initial reaction of the pyrazole acid with a chloroformate followed by low-temperature reduction with NaBH$_4$, or via a 1-step direct reduction with diborane), which is then protected to give the protected hydroxypyrazole 2. Regioselective halogenation of pyrazole 2 provides the 4-halopyrazole 3, which is then subjected to a Suzuki-Miyaura coupling with a 4-hydroxyaryl/heteroaryl boronic acid 4 to give the 4-hydroxyaryl/heteroaryl pyrazole 5. Reaction of phenol/hydroxyheteroaryl pyrazole 5 with a 3-hydroxy cyclohexyl ester 6 under Mitsunobu reaction conditions (Kumara Swamy, K. C., *Chem. Rev.*, 2009, 109, 2551-2651) furnishes the corresponding pyrazole oxycycloalkyl ester 7. Deprotection of the hydoxymethylpyrazole 7 provides the cyclohexyl ester pyrazole alcohol 8. Pyrazole alcohol 8 is then reacted with PBr$_3$ (or another mild brominating agent such as CBr$_4$/Ph$_3$P) to give the corresponding bromide 9. Displacement of pyrazole bromide 9 with NaN$_3$ (or other azide equivalent reagents) gives pyrazole azide 10, which undergoes reduction (e.g. Staudinger reduction with Ph$_3$P/water) to afford pyrazole amine 11. Pyrazole amine 11 is then reacted with an appropriate halo-azole 12 in the presence of an appropriate base (nucleophilic aromatic substitution reaction) or via Pd-catalyzed amination to give pyrazole amino-azole cyclohexyl esters 13, which then undergo ester deprotection to give the desired pyrazole-azole aryloxy cycloalkyl acids 14.

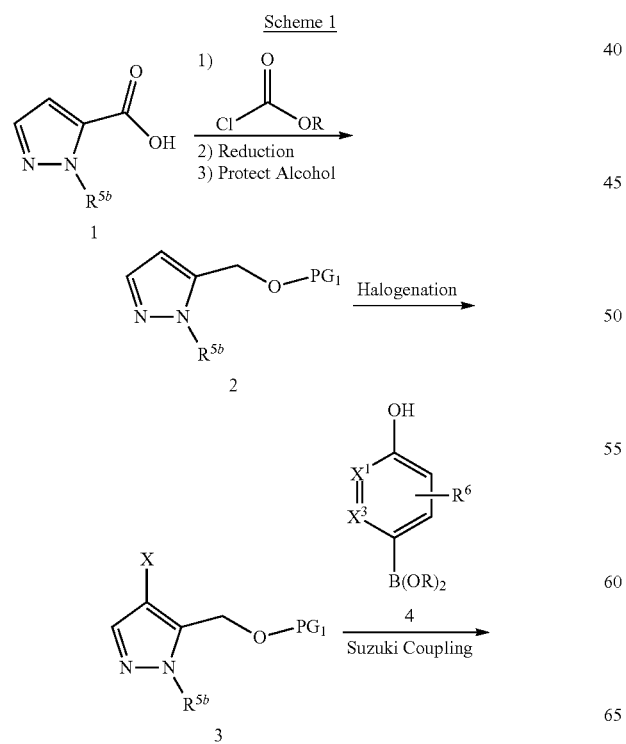

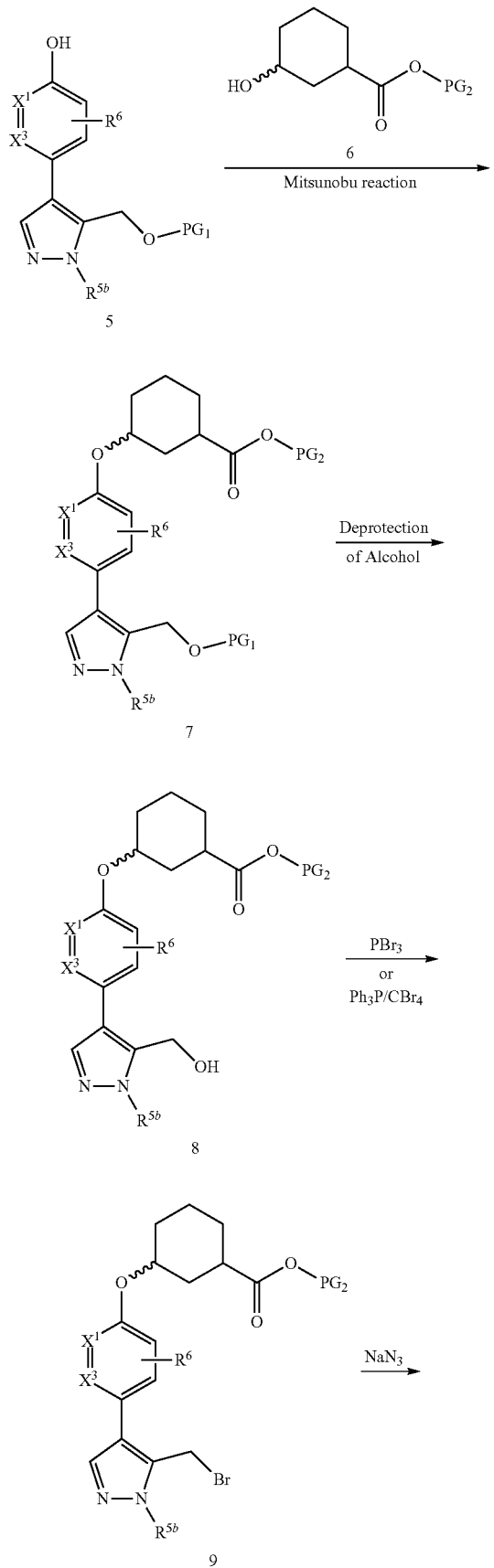

-continued

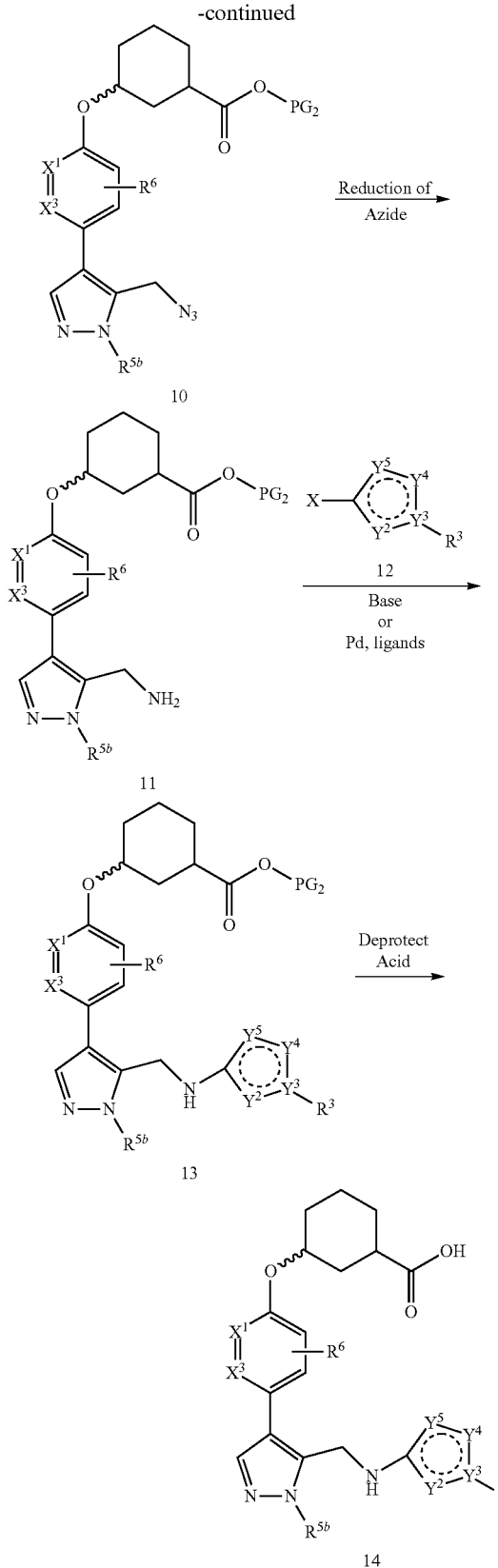

Scheme 2 describes an alternative synthetic route to the amino-azole pyrazole-aryloxy cyclohexyl acids 14. Reaction of an appropriately substituted amino-azole 15 with the cyclohexyl ester pyrazole bromide 9 either in the presence of base (e.g. NaH, etc.) or under transition metal-catalysis conditions (e.g. Pd-ligand-mediated cross-coupling) affords the amino-azole pyrazole-aryloxy cyclohexyl ester 13. Subsequent ester deprotection of cyclohexyl ester 13 provides the desired amino-azole pyrazole-aryl/heteroaryl-oxycyclohexyl acids 14.

Scheme 2

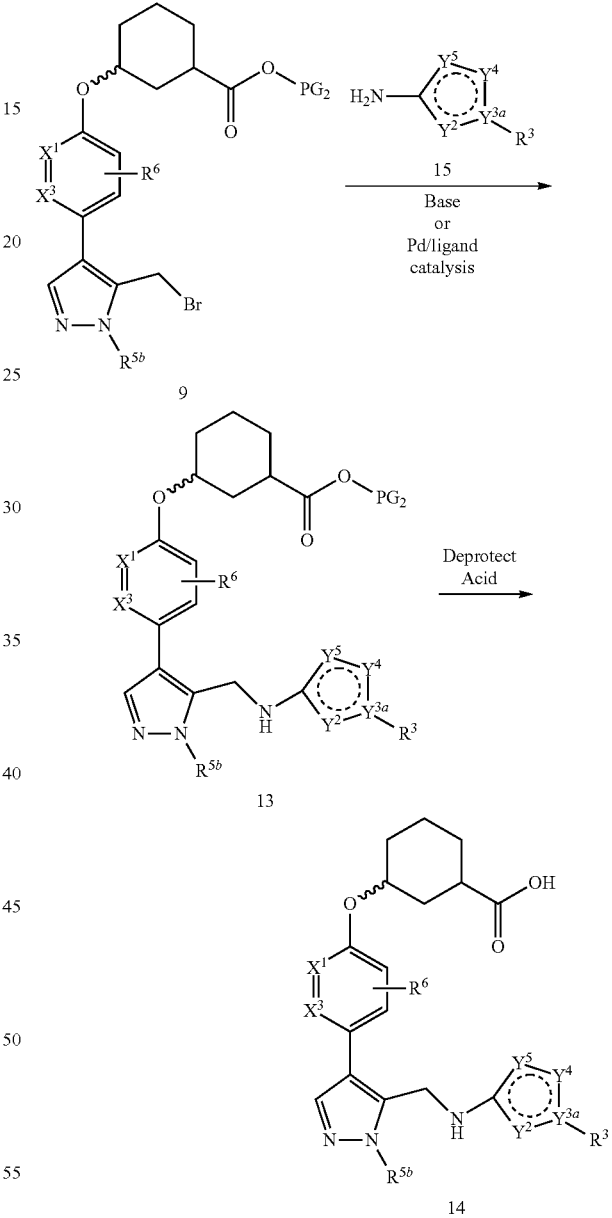

Scheme 3 describes an alternative synthesis of pyrazole-azole aryloxy-cyclohexyl acids 14. The halo-pyrazole 3 is converted to the intermediate pyrazole boronate 16 (via Pd-mediated borylation with $B_2Pin_2$; for instance Ishiyama, T. et al, *J. Org. Chem.* 1995, 60, 7508-7510). 4-Halo-hydroxyaryl/hydroxyheteroarene 17 is subjected to a Mitsunobu reaction with hydroxy-cyclohexyl ester 6 to give the 4-haloaryl/heteroaryl-oxycyclohexyl ester 18. Suzuki-Miyaura cross-coupling reaction of 4-haloarene/heteroarene 18 with pyrazole boronate 16 gives the pyrazole oxycycloalkyl ester 7, which is then converted to the pyrazole-azole cyclohexyl acids 14 using the same synthetic sequence as described in Scheme 1.

Scheme 3

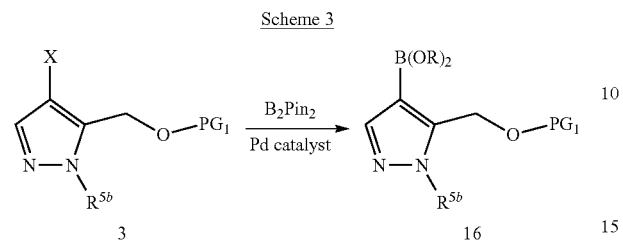

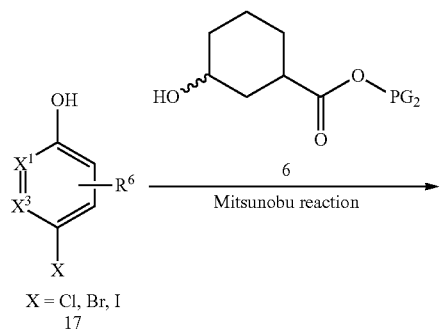

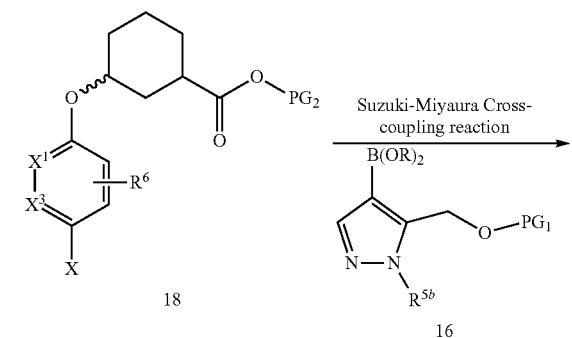

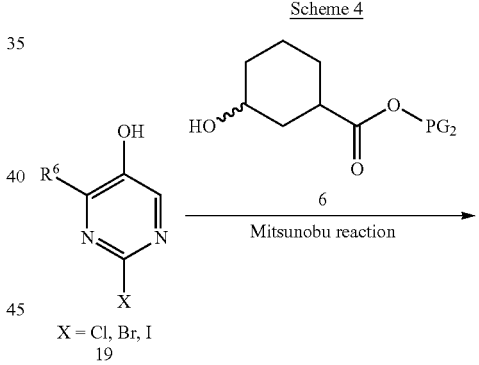

Scheme 4 describes the corresponding synthesis of pyrazole-azole pyrimidine cyclohexyl acids 22. 2-Halopyrimidin-5-ol 19 is is subjected to a Mitsunobu reaction with hydroxy-cyclohexyl ester 6 to give the 4-halopyrimidine-oxycyclohexyl ester 20. Suzuki-Miyaura cross-coupling reaction of 4-halopyrimidine oxycyclohexyl ester 20 with pyrazole boronate 16 gives the pyrazole-pyrimidine oxycycloalkyl ester 21, which is then converted to the pyrimidine-pyrazole-azole cyclohexyl acids 22 using the same synthetic sequence as described in Scheme 1.

Scheme 4

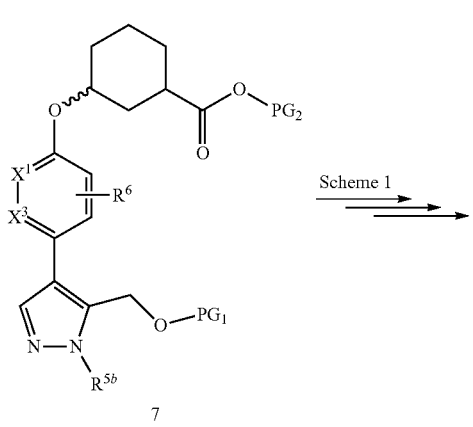

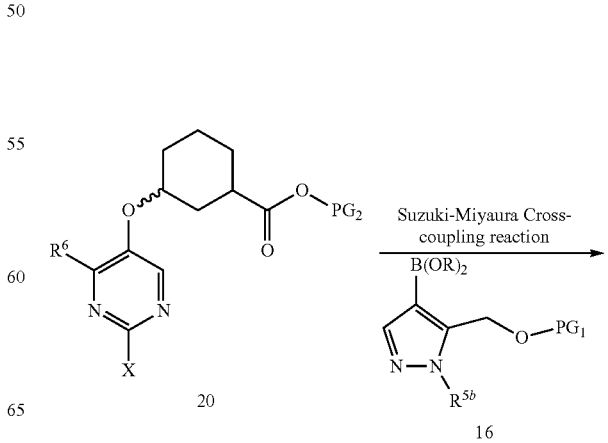

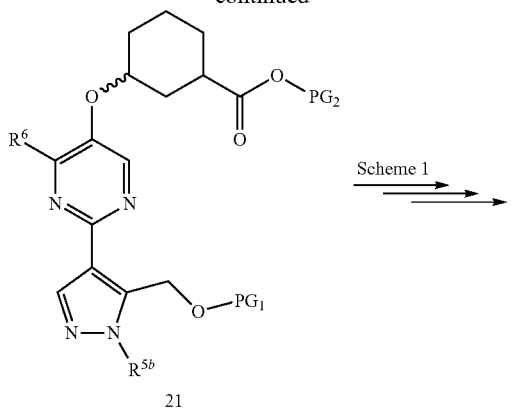

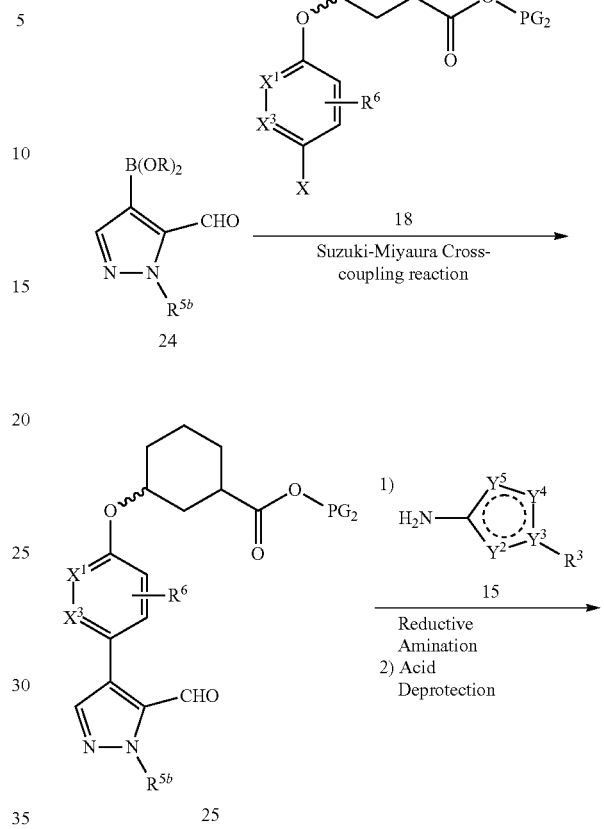

Scheme 5 describes an alternative synthetic route to pyrazole-azole cyclohexyl acids 14 and pyrimidine-pyrazole-azole cyclohexyl acids 22. A 4-halopyrazole aldehyde (available, for instance, from deprotection of pyrazole alcohol 3 followed by Dess-Martin or Swern oxidation) is converted to the intermediate pyrazole aldehyde boronate 24 (via Pd-mediated borylation with $B_2Pin_2$; for instance Ishiyama, T. et al, *J Org. Chem.* 1995, 60, 7508-7510). Suzuki-Miyaura cross-coupling reaction of 4-haloarene/heteroarene-oxycyclohexyl ester 18 with pyrazole aldehyde boronate 24 gives the pyrazole aldehyde oxycycloalkyl ester 25. Imine formation of pyrazole aldehyde 25 with an appropriately substituted amino-azole 15 (e.g. catalyzed by a Lewis acid such as $Ti(OiPr)_3Cl$) followed by reductive amination (e.g. with $NaBH(OAc)_3$, ref. Abdel-Magid, A. F., et. al., *J. Org. Chem.* 1996, 61, 3849-3862 or with $NaBH_3CN$) provides the corresponding pyrazole amino-azole cyclohexyl ester. Acid deprotection of this pyrazole-azole cyclohexyl ester provides the aryl/heteroaryl-pyrazole-azole cyclohexyl acids 14.

Scheme 5

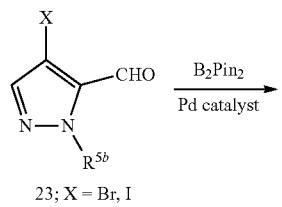

In Scheme 5a, the corresponding Suzuki-Miyaura cross-coupling reaction of the 4-halopyrimidine oxycyclohexyl ester 20 with pyrazole aldehyde boronate 24 provides the pyrimidine-pyrazole aldehyde 26. Imine formation of pyrimidine-pyrazole aldehyde 26 with an appropriately substituted amino-azole 15 followed by reductive amination also gives the corresponding pyrimidine-pyrazole amino-azole cyclohexyl ester. Acid deprotection of this pyrimidine-pyrazole-azole cyclohexyl ester provides the pyrimidine-pyrazole-azole oxycyclohexyl acids 22.

Scheme 5a

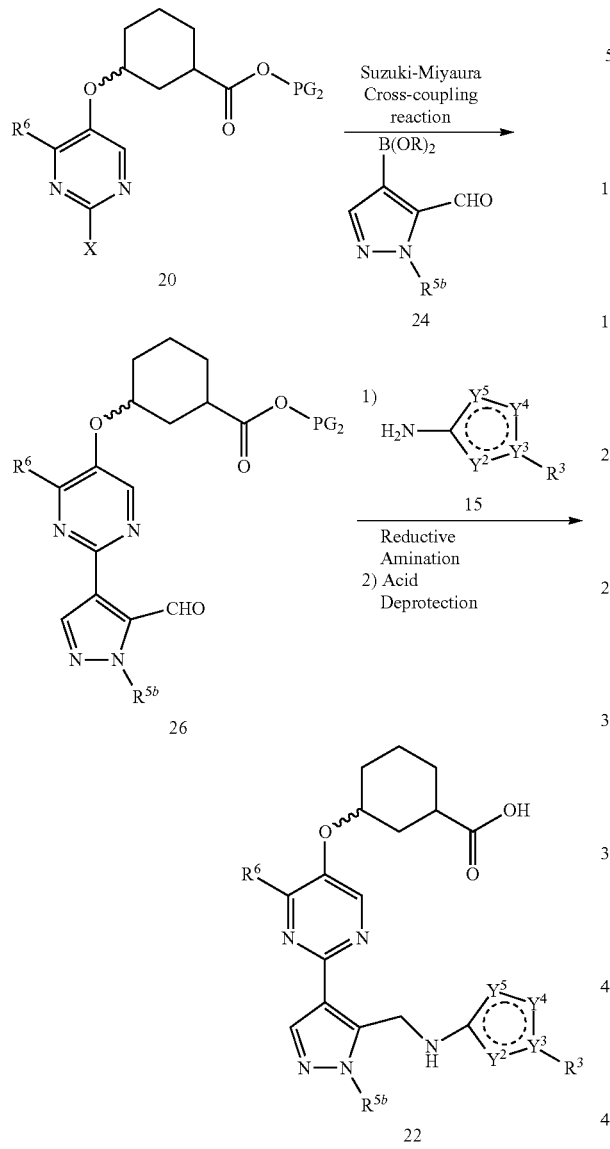

Scheme 6

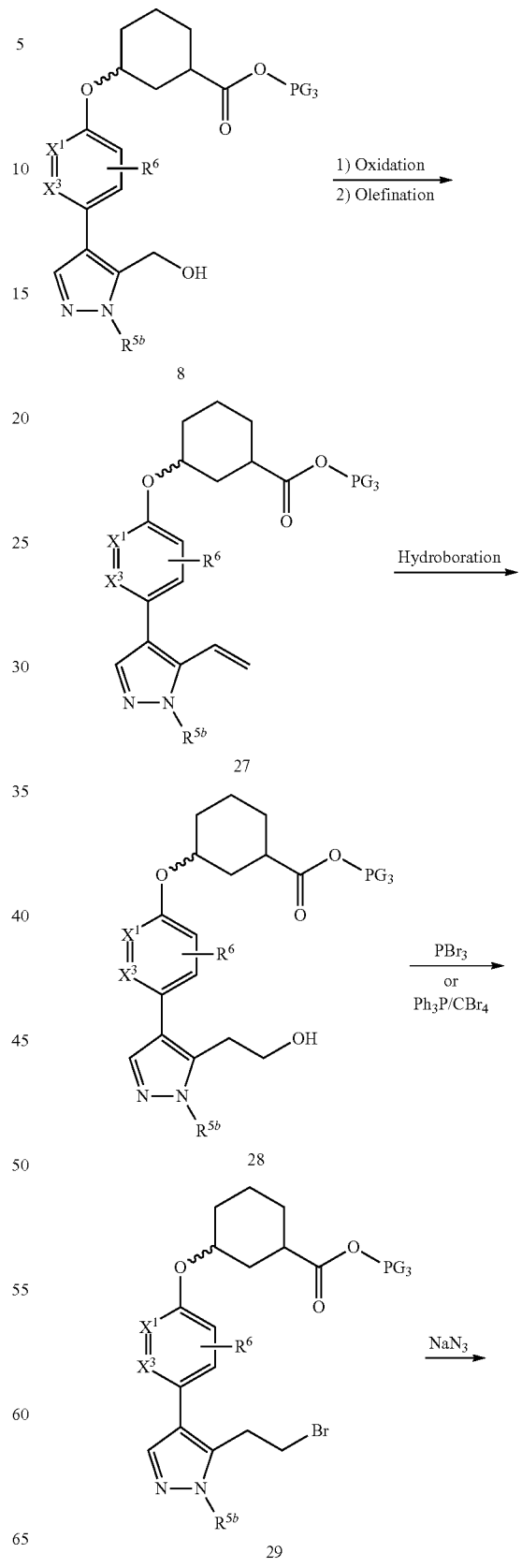

Scheme 6 describes the synthesis of pyrazole-ethyl-azole cyclohexyl acids 33. The pyrazole methanol intermediate 8 is oxidized to the corresponding aldehyde (e.g. Dess-Martin periodinane or Swern oxidation), which is then subjected to an olefination reaction (e.g. Wittig or Peterson olefination reaction) which provides the pyrazole terminal olefin 27. Hydroboration of olefin 27 at the terminal carbon (e.g. with 9-BBN), followed by oxidative workup, provides the corresponding pyrazole ethyl alcohol 28. Pyrazole ethyl alcohol 28 is then reacted with PBr$_3$ (or another mild brominating agent such as CBr$_4$/Ph$_3$P) to give the corresponding bromide 29. Displacement of bromide 29 with NaN$_3$ (or other azide equivalent reagents) gives pyrazole azide 30 which undergoes reduction (e.g. Staudinger reduction with Ph$_3$P/water) to afford pyrazole amine 31. Pyrazole amine 31 is then reacted with halo-azole 12 in the presence of an appropriate base or via transition metal (e.g. Pd)-catalyzed amination to give the pyrazole amino-azole cyclohexyl ester 32, which then undergoes ester deprotection to give the desired pyrazole-ethyl-amino-azole aryloxy cyclohexyl acids 33.

-continued

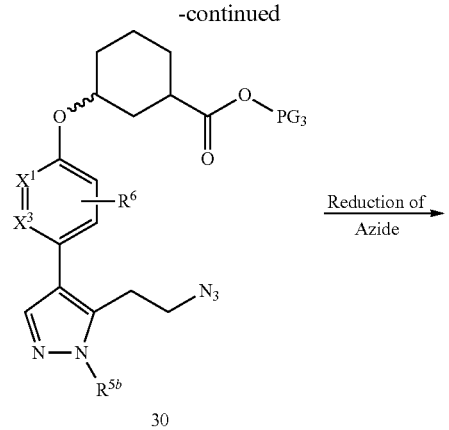

30

Reduction of Azide →

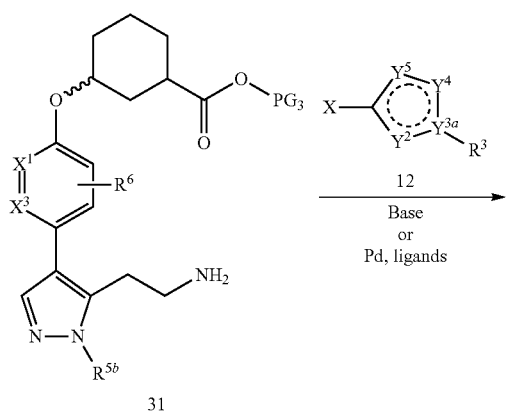

31

12
Base
or
Pd, ligands
→

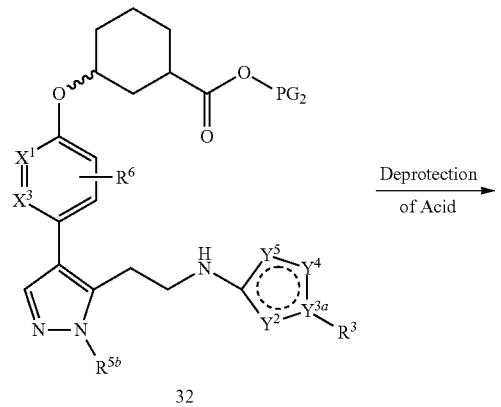

32

Deprotection of Acid →

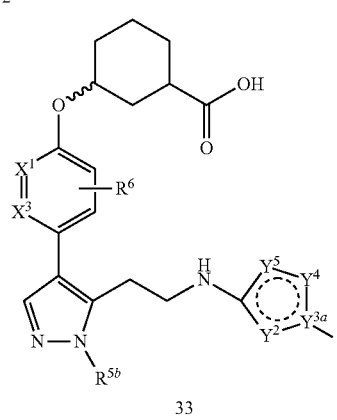

33

Scheme 7 describes the synthesis of pyrazole amino-azole acids 38. Cyclohexyl ether pyrazole-alcohol 8 undergoes oxidation to the pyrazole carboxylic acid 34 (e.g. directly to the acid with e.g. pyridinium dichromate or via a 2-step procedure via the aldehyde [Swern oxidation or Dess-Martin periodinane followed by $NaClO_2$ oxidation to the acid, e.g. Lindgren, B. O., *Acta Chem. Scand* 1973, 27, 888]). Curtius rearrangement (e.g. with $(PhO)_2PON_3$) of pyrazole acid 34 in the presence of t-butanol provides the pyrazole NH-Boc-carbamate 35. Deprotection of the pyrazole NH-Boc carbamate 35 under acidic conditions provides the pyrazole amine 36. The pyrazole-amine 36 then undergoes a transition metal (e.g. Pd)-catalyzed cross-coupling reaction with an appropriately substituted halo-azole 12 to provide the pyrazole amino-azole cyclohexyl ester 37, which then undergoes ester deprotection to give the desired pyrazole-aminoazole-aryloxy cyclohexyl acids 38.

Scheme 7

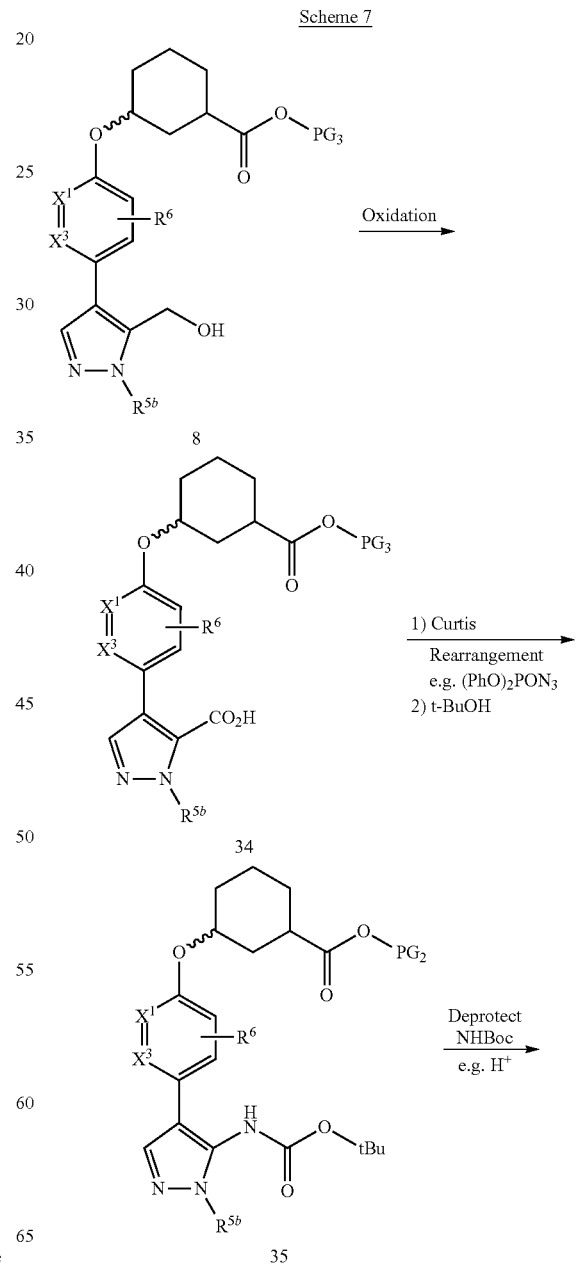

-continued

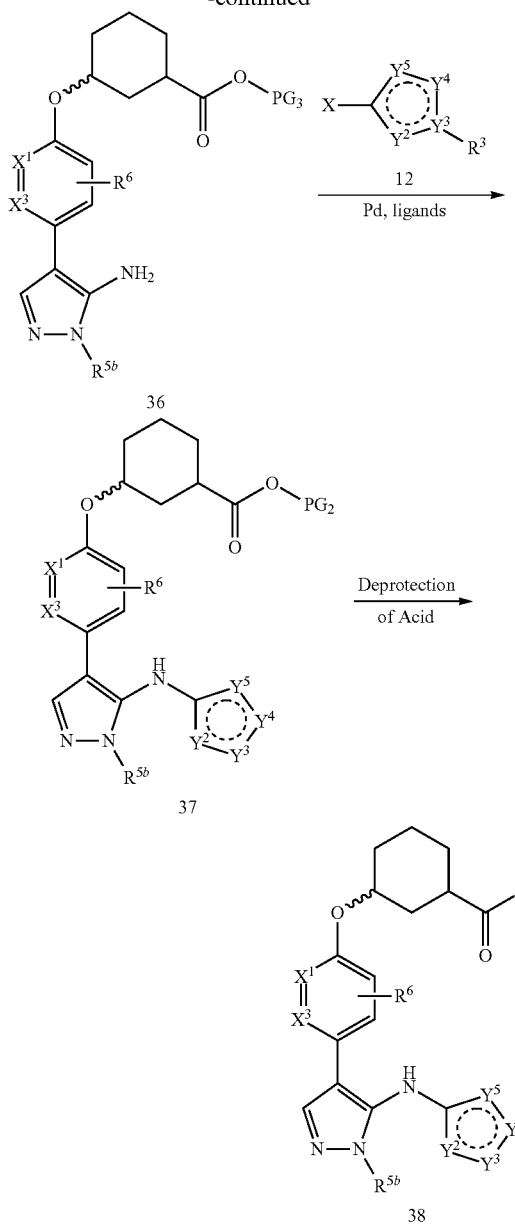

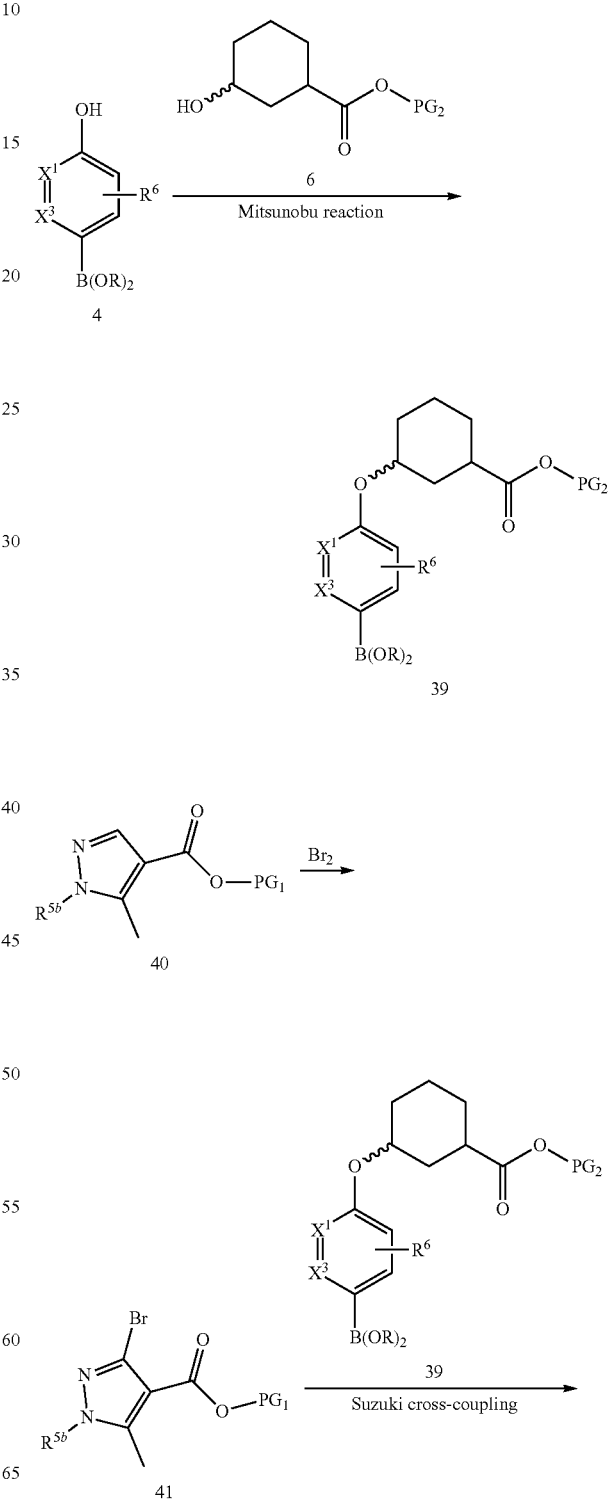

by low-temperature reduction with NaBH₄, or directly with diborane as in Scheme 1) to the corresponding pyrazole alcohol 44. Cyclohexyl ester-pyrazole alcohol 44 is then converted to the pyrazole amino-azole acids 45 by the same synthetic sequence as described in Scheme 1 (i.e. 8→14).

Scheme 8

Scheme 8 describes the synthesis of pyrazole amino-azole acids 45. Reaction of a 4-hydroxy aryl/heteroaryl boronate 4 with a 3-hydroxy cyclohexyl ester 6 under Mitsunobu reaction conditions (Kumara Swamy, K. C., *Chem. Rev.*, 2009, 109, 2551-2651) furnishes the corresponding aryl/heteroaryl oxycycloalkyl ester 39. An protected 1,5-dialkyl-1H-pyrazole-4-carboxylic acid ester 40 is brominated to give bromo-pyrazole 41. The bromopyrazole 41 is subjected to a Suzuki-Miyaura coupling reaction with the aryl/heteroaryl boronate 39 (or the corresponding boronic acid), to furnish the corresponding pyrazole-aryl/heteroaryl oxycycloalkyl ester 42. The pyrazole ester of 42 is selectively deprotected to the corresponding pyrazole carboxylic acid 43, which then undergoes reduction (e.g. by a 2 step, 1-pot reaction via reaction with an alkyl chloroformate followed -continued

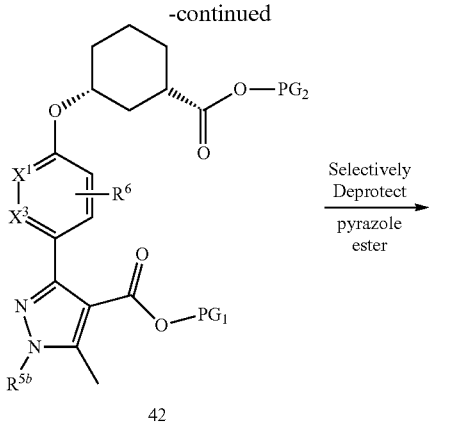

42

Selectively Deprotect pyrazole ester →

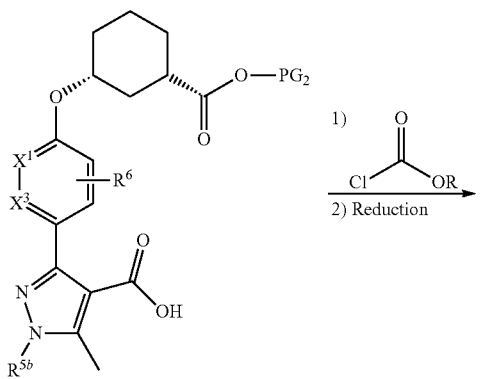

43

1) 
$$\underset{Cl}{\overset{O}{\|}}\underset{}{\overset{}{C}}OR$$
2) Reduction →

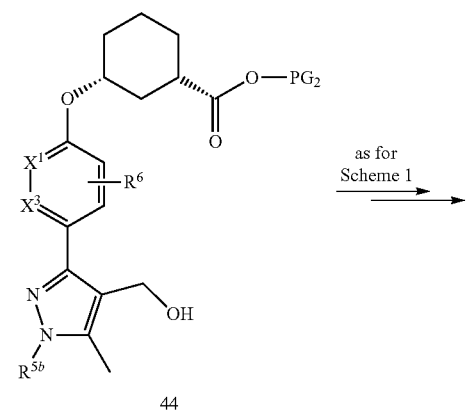

44 as for Scheme 1 →

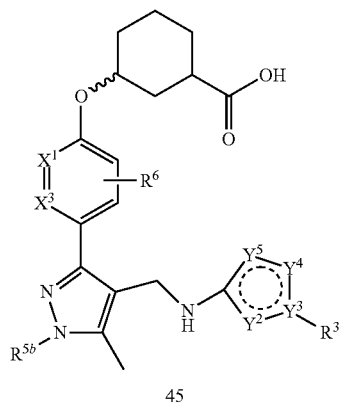

45

VII. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

Microwave reactions were carried out using a 400 W Biotage Initiator instrument in microwave reaction vessels (0.2-0.5 mL; 0.5-2 mL; 2-5 mL; 10-20 mL) under microwave (2.5 GHz) irradiation.

HPLC/MS and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

In the examples where $^1$H NMR spectra were collected in $d_6$-DMSO, a water-suppression sequence is often utilized. This sequence effectively suppresses the water signal and any proton peaks in the same region usually between 3.30-3.65 ppm which will affect the overall proton integration.

The term HPLC refers to a Shimadzu high performance liquid chromatography instrument with one of following methods:

HPLC-1: Sunfire C18 column (4.6×150 mm) 3.5 μm, gradient from 10 to 100% B:A for 12 min, then 3 min hold at 100% B.
Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.
HPLC-2: XBridge Phenyl (4.6×150 mm) 3.5 μm, gradient from 10 to 100% B:A for 12 min, then 3 min hold at 100% B.
Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.
HPLC-3: Chiralpak AD-H, 4.6×250 mm, 5 μm.
Mobile Phase: 30% EtOH-heptane (1:1)/70% CO$_2$
Flow rate=40 mL/min, 100 Bar, 35° C.; Wavelength: 220 nm
HPLC-4: Waters Acquity UPLC BEH C18, 2.1×50 mm, 1.7-μm particles;
Mobile Phase A: 5:95 CH$_3$CN:water with 10 mM NH$_4$OAc;
Mobile Phase B: 95:5 CH$_3$CN:water with 10 mM NH$_4$OAc;
Temperature: 50° C.; Gradient: 0-100% B over 3 min, then a 0.75-min hold at 100% B;
Flow: 1.11 mL/min; Detection: UV at 220 nm.
HPLC-5: Waters Acquity UPLC BEH C18, 2.1×50 mm, 1.7-μm particles;
Mobile Phase A: 5:95 CH$_3$CN:water with 0.1% TFA;
Mobile Phase B: 95:5 CH$_3$CN:water with 0.1% TFA;

Temperature: 50° C.; Gradient: 0-100% B over 3 min, then a 0.75-min hold at 100% B; Flow: 1.11 mL/min; Detection: UV at 220 nm.

Intermediate 1. Isopropyl trans-3-((6-(5-(bromomethyl)-1-methyl-1H-pyrazol-4-yl)pyridin-3-yl)oxy)cyclohexane-1-carboxylate

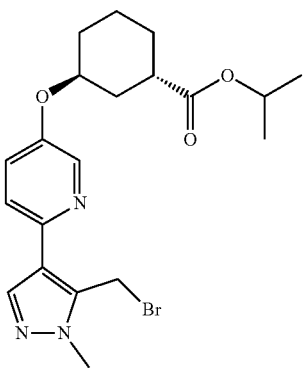 [SMILES: CC(C)OC(=O)[C@H]1CCC[C@H](Oc2ccc(-c3cnn(C)c3CBr)nc2)C1]

Intermediate 1A. 4-bromo-1-methyl-5-(((tetrahydro-2H-pyran-2-yl)oxy)methyl)-1H-pyrazole

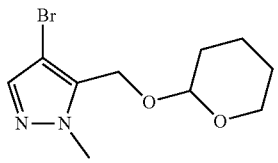

pTsOH.H$_2$O (0.050 g, 0.262 mmol) was added to a solution of (4-bromo-1-methyl-1H-pyrazol-5-yl)methanol (1.0 g, 5.2 mmol) and 3,4-dihydro-2H-pyran (1.32 g, 15.7 mmol) in DCM (10 mL) at 0° C. The reaction was allowed to warm to RT and stirred overnight at RT. The reaction was cooled to 0° C. and neutralized with satd aq. NaHCO$_3$ to pH 7. The mixture was partitioned between DCM (10 mL) and water (10 mL), and the aqueous layer was extracted with DCM (3×10 mL). The combined organic extracts were dried (MgSO$_4$) and concentrated in vacuo. The residue was chromatographed (SiO$_2$; EtOAc/hexanes) to provide title compound (1.40 g, 5.09 mmol, 97% yield) as a colorless oil. $^1$H NMR (500 MHz, CDCl$_3$) δ 7.41 (s, 1H), 4.72 (d, J=12.9 Hz, 1H), 4.65 (dd, J=4.1, 3.0 Hz, 1H), 4.58 (d, J=12.9 Hz, 1H), 3.93 (s, 3H), 3.88 (ddd, J=11.6, 8.3, 3.1 Hz, 1H), 3.57 (dddd, J=11.0, 5.0, 3.9, 1.4 Hz, 1H), 3.49 (d, J=5.5 Hz, 2H), 1.85-1.75 (m, 1H), 1.75-1.66 (m, 1H), 1.66-1.48 (m, 4H). [M+H]$^+$=275.1.

Intermediate 1B. 1-methyl-5-(((tetrahydro-2H-pyran-2-yl)oxy)methyl)-4-(4,4,5,5-tetramethyl-1,3,2-dioxaborolan-2-yl)-1H-pyrazole

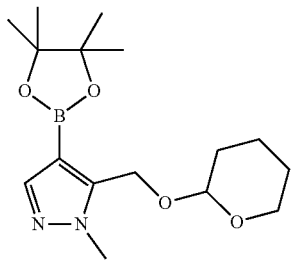 [SMILES: Cn1ncc(B2OC(C)(C)C(C)(C)O2)c1COC1CCCCO1]

A mixture of 1A (469 mg, 1.71 mmol), KOAc (502 mg, 5.11 mmol), bis(pinacolato) diboron (649 mg, 2.56 mmol) in 1,4 dioxane (10 ml) was degassed with N$_2$ for 5 min. PdCl$_2$(dppf) (125 mg, 0.170 mmol) was added and the reaction was degassed again with N$_2$ for 5 min. The reaction vessel was sealed and heated at 85° C. for 10 h, then was cooled to RT. The mixture was partitioned between EtOAc (10 mL) and water (10 mL), the aqueous phase was extracted with EtOAc (3×10 mL). The combined organic extracts were dried (MgSO$_4$) and concentrated in vacuo to afford the crude title compound (717 mg, 0.890 mmol, 52.2% yield) as a yellow colorless oil. [M+H]$^+$=323.1.

Intermediate 1C. isopropyl trans-3-((6-bromopyridin-3-yl)oxy)cyclohexane-1-carboxylate

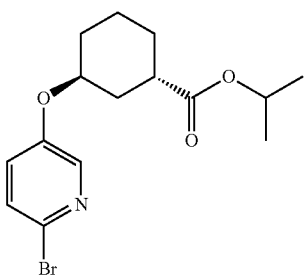 [SMILES: CC(C)OC(=O)[C@H]1CCC[C@H](Oc2ccc(Br)nc2)C1]

To a mixture of 6-bromopyridin-3-ol (300 mg, 1.72 mmol), (±)-cis-isopropyl 3-hydroxycyclo-hexane carboxylate (353 mg, 1.90 mmol), Et$_3$N (0.264 mL, 1.90 mmol) and Ph$_3$P (497 mg, 1.90 mmol) in THF (2 mL) at 0° C. was added DIAD (0.369 mL, 1.90 mmol) dropwise over 15 min. The reaction was stirred overnight at RT, then was partitioned between EtOAc (5 mL) and water (5 mL). The aqueous layer was extracted with EtOAc (3×10 mL). The combined organic extracts were washed with brine (5 mL), dried (MgSO$_4$) and concentrated in vacuo. The crude product was chromatographed (SiO$_2$; EtOAc/hexanes) to provide the title compound (255 mg, 0.745 mmol, 43.2% yield) as a white solid. $^1$H NMR (500 MHz, CDCl$_3$) δ 8.07 (d, J=3.2 Hz, 1H), 7.36 (d, J=8.8 Hz, 1H), 7.14 (dd, J=8.7, 3.1 Hz, 1H), 5.02 (hept, J=6.3 Hz, 1H), 4.61 (dq, J=8.7, 5.3, 4.2 Hz, 1H), 2.76 (tt, J=9.0, 4.4 Hz, 1H), 2.03-1.51 (m, 8H), 1.24 (dd, J=6.3, 1.9 Hz, 6H). [M+H]$^+$=342.

Intermediate 1D. Isopropyl trans-3-((6-(1-methyl-5-(((tetrahydro-2H-pyran-2-yl)oxy)methyl)-1H-pyrazol-4-yl)pyridin-3-yl)oxy)cyclohexane-1-carboxylate

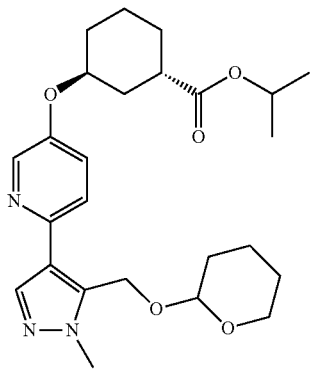 [SMILES: CC(C)OC(=O)[C@H]1CCC[C@H](Oc2ccc(-c3cnn(C)c3COC3CCCCO3)nc2)C1]

To the solution of 1B (717 mg, 0.891 mmol) in 1,4-dioxane (2 mL) was added 1C (254 mg, 0.742 mmol), and K$_2$HPO$_4$ (388 mg, 2.23 mmol), 2$^{nd}$ generation XPhos pre-catalyst (29 mg, 0.037 mmol) and water (2 mL). The mixture was evacuated in vacuo and recharged with Ar (3×). The mixture was stirred at 60° C. for 24 h, then cooled to RT and stirred at RT for 24 h. The mixture was extracted with EtOAc (3×5 mL), dried (MgSO$_4$) and concentrated in vacuo to afford the crude product. The crude material was chromatographed (12 g SiO$_2$, continuous gradient from 0 to 100% EtOAc in hexanes in 12 min) to afford the title compound (212 mg, 0.417 mmol, 56.2% yield) as a slightly yellow oil. $^1$H NMR (500 MHz, CDCl$_3$) δ 8.30 (d, J=2.9 Hz, 1H), 7.76 (s, 1H), 7.46-7.39 (m, 1H), 7.28-7.21 (m, 1H), 5.08-4.94 (m, 3H), 4.72 (dd, J=4.5, 3.0 Hz, 1H), 4.65 (tq, J=5.5, 2.8 Hz, 1H), 3.97 (s, 3H), 3.88 (ddd, J=11.3, 7.9, 3.2 Hz, 1H), 3.56-3.45 (m, 1H), 2.80 (tt, J=9.8, 4.1 Hz, 1H), 2.09-1.48 (m, 14H), 1.24 (dd, J=6.3, 1.8 Hz, 6H). [M+H]$^+$=458.1.

Intermediate 1E. isopropyl trans-3-((6-(5-(hydroxymethyl)-1-methyl-H-pyrazol-4-yl)pyridin-3-yl)oxy)cyclohexane-1-carboxylate

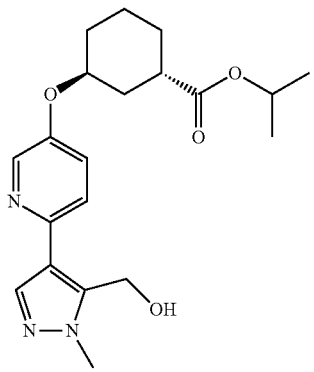 [SMILES: CC(C)OC(=O)[C@H]1CCC[C@H](Oc2ccc(-c3cnn(C)c3CO)nc2)C1]

To a solution of 1D (212 mg, 0.463 mmol) in MeOH (5 mL) was added PPTS (12 mg, 0.046 mmol). The mixture was heated at 60° C. for 4 h, then was cooled to RT, quenched with satd aq. NaHCO$_3$ (2 mL) and concentrated in vacuo to remove the MeOH. The residue was extracted with EtOAC (3×5 mL). The combined organic extracts were dried (MgSO$_4$) and concentrated in vacuo. The crude product was chromatographed (4 g SiO$_2$; continuous gradient from 0% to 100% EtOAc in Hexanes, 12 min) to afford the title compound (75 mg, 0.201 mmol, 43.3% yield) as a colorless oil. $^1$H NMR (500 MHz, CDCl$_3$) δ 8.15 (d, J=2.9 Hz, 1H), 7.66 (s, 1H), 7.43 (d, J=8.8 Hz, 1H), 7.26 (dd, J=8.8, 2.9 Hz, 1H), 6.93 (s, 1H), 4.95 (hept, J=6.2 Hz, 1H), 4.65 (s, 2H), 4.58 (dq, J=5.8, 2.8 Hz, 1H), 3.85 (3, 3H), 2.72 (tt, J=9.0, 4.3 Hz, 1H), 1.99-1.46 (m, 8H), 1.17 (dd, J=6.3, 2.3 Hz, 6H). [M+H]$^+$=374.2.

Intermediate 1

PBr$_3$ (0.040 mL, 0.426 mmol) was added to a solution of 1E (53 mg, 0.142 mmol) in DME (1.5 mL) at 0° C. The reaction was stirred overnight at RT, then was cooled to 0° C. and neutralized with satd aq. NaHCO$_3$ to pH 7. The mixture was partitioned between DCM (5 mL) and water (3 mL) and the aqueous layer was extracted with DCM (3×3 mL). The combined organics extracts were dried (MgSO$_4$) and concentrated in vacuo. The residue was chromatographed (SiO$_2$; EtOAc/hexanes) to provide the title compound (55 mg, 0.126 mmol, 89% yield) as a white solid. H NMR (500 MHz, CDCl$_3$) δ 8.34 (d, J=2.8 Hz, 1H), 7.74 (s, 1H), 7.45 (d, J=8.8 Hz, 1H), 7.32-7.24 (m, 1H), 5.11 (s, 2H), 5.04 (p, J=6.2 Hz, 1H), 4.68 (tt, J=5.5, 3.0 Hz, 1H), 3.96 (s, 3H), 2.80 (dd, J=9.4, 4.2 Hz, 1H), 2.09-1.53 (m, 8H), 1.26 (dd, J=6.2, 2.5 Hz, 6H). [M+H]$^+$=436.0.

Intermediate 2. Isopropyl (1S,3S)-3-((2-(5-(aminomethyl)-1-methyl-H-pyrazol-4-yl)-4-methylpyrimidin-5-yl)oxy)cyclohexane-1-carboxylate

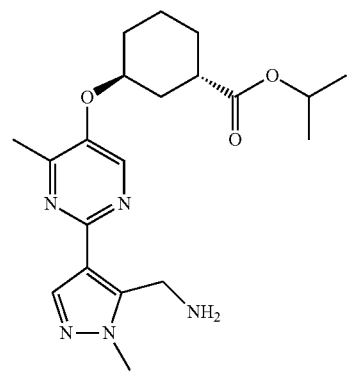 [SMILES: Cc1nc(-c2cnn(C)c2CN)ncc1O[C@H]1CCC[C@H](C(=O)OC(C)C)C1]

Intermediate 2A.
(4-Bromo-1-methyl-1H-pyrazol-5-yl)methanol

A mixture of 4-bromo-1-methyl-1H-pyrazole-5-carboxylic acid (5.0 g, 24.4 mmol) and BH$_3$.THF (36.6 mL of a 1 M solution in THF, 36.6 mmol) in THF (50 mL) was stirred at 50° C. for 2 days; at this point LCMS showed the completion of the reaction. The reaction was cooled to RT and cautiously quenched with aq. 1N HCl and stirred at RT for 1 h, after which the mixture was extracted with EtOAc (3×50 mL). The combined organic extracts were concentrated in vacuo. The residue was chromatographed (80 g SiO$_2$; continuous gradient from 0% to 100% EtOAc in hexanes, 25 min) to give the title compound (3.60 g, 18.9 mmol, 77% yield) as a white solid. LCMS, [M+H]$^+$=193.0.

Intermediate 2B. 4-bromo-1-methyl-5-(((tetrahydro-2H-pyran-2-yl)oxy)methyl)-1H-pyrazole

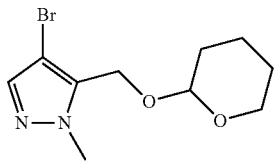

p-TsOH.H$_2$O (0.050 g, 0.262 mmol) was added to a RT solution of Intermediate 1A (1.0 g, 5.23 mmol) and 3,4-dihydro-2H-pyran (1.32 g, 15.7 mmol) in DCM (10 mL) at 0° C. The reaction was allowed to warm to RT and was stirred overnight at RT. The mixture was cooled to 0° C., neutralized with sat'd aq. NaHCO$_3$ to pH 7, then was partitioned between DCM (10 mL) and H$_2$O (10 mL). The aqueous layer was extracted with DCM (3×10 mL). The combined organic extracts were dried (MgSO$_4$) and concentrated in vacuo. The residue was chromatographed (40 g SiO$_2$; continuous gradient from 0%-80% EtOAc in hexanes over 14 min) to give the title compound (1.4 g, 5.09 mmol, 97% yield) as a colorless oil. $^1$H NMR (500 MHz, CDCl$_3$) δ 7.41 (s, 1H), 4.72 (d, J=12.9 Hz, 1H), 4.65 (dd, J=4.1, 3.0 Hz, 1H), 4.58 (d, J=12.9 Hz, 1H), 3.93 (s, 3H), 3.88 (ddd, J=11.6, 8.3, 3.1 Hz, 1H), 3.57 (dddd, J=11.0, 5.0, 3.9, 1.4 Hz, 1H), 3.49 (d, J=5.5 Hz, 2H), 1.85-1.75 (m, 1H), 1.75-1.66 (m, 1H), 1.66-1.48 (m, 4H). [M+H]$^+$=275.1.

Intermediate 2C. 1-Methyl-5-(((tetrahydro-2H-pyran-2-yl)oxy)methyl)-4-(4,4,5,5-tetramethyl-1,3,2-dioxaborolan-2-yl)-1H-pyrazole

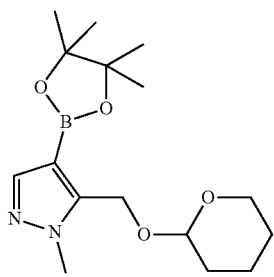 [SMILES: Cn1ncc(B2OC(C)(C)C(C)(C)O2)c1COC1CCCCO1]

Ar was vigorously bubbled through a stirred mixture of Intermediate 2B (550 mg, 2.00 mmol), KOAc (589 mg, 6.00 mmol) and B$_2$Pin$_2$ (761 mg, 3.00 mmol) in 1,4-dioxane (10 mL) for 5 min. Pd(dppf)Cl$_2$—CH$_2$Cl$_2$ (163 mg, 0.20 mmol) was added, and the reaction flushed with Ar, then was heated to 100° C. for 16 h; LCMS analysis after 16 h indicated that the reaction was complete. The reaction mixture was cooled to RT and partitioned between CH$_2$Cl$_2$ (20 mL) and H$_2$O (10 mL); the resulting mixture was stirred vigorously. The organic layer was dried (Na$_2$SO$_4$) and concentrated in vacuo. The crude product was used in the next step without further purification.

Intermediate 2D. 2-Bromo-4-methylpyrimidin-5-ol

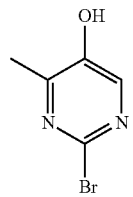

A mixture of 2-chloro-4-methylpyrimidin-5-ol (500 mg, 3.46 mmol) and HBr (30 wt. % in HOAc; 3 mL) was heated to 110° C. overnight, after which LCMS indicated the reaction was complete. The reaction mixture was cooled to RT, then was poured onto ice and extracted with EtOAc (3×50 mL). The combined organic extracts were washed with satd aq Na$_2$CO$_3$, water and brine, then was dried (Na$_2$SO$_4$) and concentrated in vacuo to afford the title compound (630 mg, 3.33 mmol, 96% yield) as an off-white solid. [M+H]$^+$=189.1.

Intermediate 2E. 4-Methyl-2-(1-methyl-5-(((tetrahydro-2H-pyran-2-yl)oxy)methyl)-1H-pyrazol-4-yl)pyrimidin-5-ol

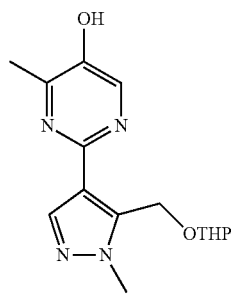

A mixture of bis(di-tert-butyl(4-dimethylaminophenyl)phosphine) dichloropalladium (II) (101 mg, 0.14 mmol), Intermediate 2C (552 mg, 1.71 mmol), Intermediate 2D (270 mg, 1.43 mmol), aq. 2 M Na$_2$CO$_3$ (3.6 mL, 7.14 mmol) in MeCN (7 mL) was heated at 100° C. in a microwave reactor for 1 h, then was cooled to RT, diluted with satd aq. NaHCO$_3$, and extracted with EtOAc (3×50 mL). The combined organic extracts were washed with brine, dried (Na$_2$SO$_4$) and concentrated in vacuo. The crude product was chromatographed (80 g SiO$_2$, continuous gradient from 0%-90% EtOAc in hexanes) to provide the title compound (250 mg, 0.82 mmol, 58% yield) as a beige solid. $^1$H NMR (500 MHz, CDCl$_3$) δ 8.85 (d, J=1.42 Hz, 1H), 8.14 (d, J=1.41 Hz, 1H), 5.15 (m, 2H), 4.98 (m, 1H), 4.69 (m, 1H), 4.13 (s, 3H), 3.82 (ddd, J=11.33, 7.90, 3.08 Hz, 1H), 3.49 (m, 1H), 2.74 (tt, J=11.5, 3.67 Hz, 1H), 2.15 (m, 1H), 1.98-1.50 (m, 13H), 1.20 (m, 6H). [M+H]$^+$=305.1. $^1$H NMR (500 MHz, DMSO-d6) δ 8.17 (s, 1H), 7.86 (s, 1H), 5.26 (d, J=11.9 Hz, 1H), 5.09 (d, J=11.9 Hz, 1H), 4.77-4.69 (m, 1H), 3.87 (s, 3H), 3.85-3.77 (m, 2H), 2.37 (s, 3H), 1.73-1.39 (m, 6H).

Intermediate 2F. Isopropyl (1S,3S)-3-((4-methyl-2-(1-methyl-5-(((tetrahydro-2H-pyran-2-yl)oxy)methyl)-1H-pyrazol-4-yl)pyrimidin-5-yl)oxy)cyclohexane-1-carboxylate

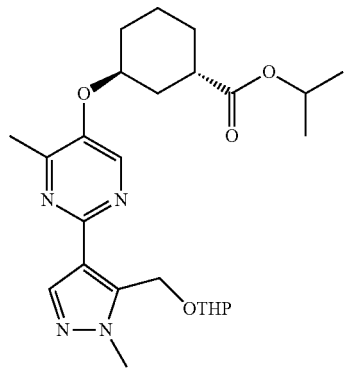

A mixture of (E)-diazene-1,2-diylbis(piperidin-1-ylmethanone) (435 mg, 1.73 mmol), toluene (8 mL) and Bu$_3$P (0.43 mL, 1.73 mmol) was stirred at RT for 30 min, after which Intermediate 2E (210 mg, 0.69 mmol) and isopropyl (1S,3R)-3-hydroxycyclohexane-1-carboxylate (231 mg, 1.24 mmol) were successively added. The reaction mixture was heated at 85° C. for 9 h, after which LC/MS indicated the formation of the desired product. The reaction was cooled to RT and diluted with CH$_2$Cl$_2$; the mixture was filtered and the filtrate was concentrated in vacuo. The crude oily product was chromatographed (80 g SiO$_2$; continuous gradient from 0% to 90% EtOAc/Hex over 25 min, hold at 90% for 20 min) to give the title compound (190 mg, 0.40 mmol, 58% yield) as a light yellow oil. $^1$H NMR (500 MHz, CDCl$_3$) δ 8.98 (s, 1H), 8.09 (s, 1H), 5.51 (t, J=6.90 Hz, 1H), 5.43 (s, 1H), 4.98 (m, 1H), 4.80 (d, J=6.88 Hz, 2H), 4.07 (s, 3H), 2.72 (tt, J=11.5, 3.67 Hz, 1H), 2.15 (m, 1H), 1.98-1.50 (m, 7H), 1.20 (m, 6H). [M+H]$^+$=473.2.

Intermediate 2G. Isopropyl (1S,3S)-3-((2-(5-(hydroxymethyl)-1-methyl-1H-pyrazol-4-yl)-4-methylpyrimidin-5-yl)oxy)cyclohexane-1-carboxylate

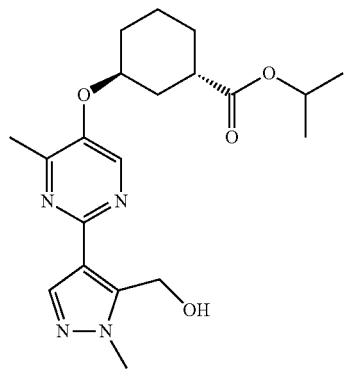 [SMILES: Cc1nc(-c2cnn(C)c2CO)ncc1O[C@H]1CCC[C@H](C(=O)OC(C)C)C1]

A solution of Intermediate 2F (190 mg, 0.40 mmol) and PPTS (15 mg, 0.06 mmol) in MeOH (4 mL) was heated at 60° C. overnight, then was cooled to RT and concentrated in vacuo. Sat'd aq NaHCO$_3$ was added and the mixture was extracted with EtOAc (3×25 mL). The combined organic extracts were washed with H$_2$O and brine, dried (MgSO$_4$) and concentrated in vacuo. The crude product was chromatographed (40 g SiO$_2$, continuous gradient from 0%-100% EtOAc in hexanes) to provide the title compound (140 mg, 90% yield) as a beige solid. [M+H]$^+$=389.2.

Intermediate 2H. Isopropyl (1S,3S)-3-((2-(5-(bromomethyl)-1-methyl-H-pyrazol-4-yl)-4-methylpyrimidin-5-yl)oxy)cyclohexane-1-carboxylate

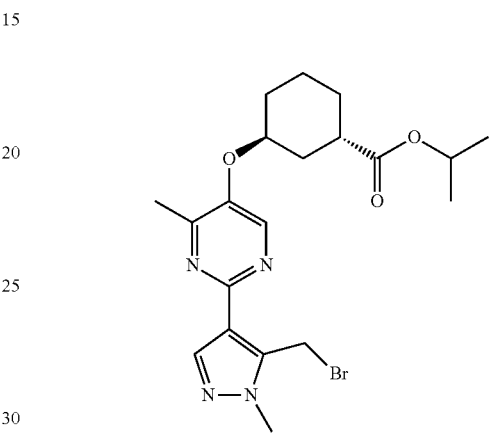

PBr$_3$ (0.09 mL, 0.90 mmol) was added to a solution of Intermediate 2G (140 mg, 0.36 mmol) in DME (4 mL) at 0° C. The reaction was allowed to warm to RT and stirred at RT overnight, then was cooled to 0° C. and sat'd aq NaHCO$_3$ was cautiously added to quench the reaction and the pH was adjusted to ~7. The mixture was partitioned between EtOAc (200 mL) and H$_2$O (10 mL); the aqueous layer was extracted with EtOAc (3×10 mL). The combined organic extracts were dried (MgSO$_4$) and concentrated in vacuo. The crude product was chromatographed (40 g SiO$_2$; continuous gradient from 0% to 60% of EtOAc:hexanes over 20 min) to give the title compound (140 mg, 0.31 mmol, 86% yield) as a colorless oil. [M+H]$^+$=453.0.

Intermediate 2I. Isopropyl (1S,3S)-3-((2-(5-(azidomethyl)-1-methyl-H-pyrazol-4-yl)-4-methylpyrimidin-5-yl)oxy)cyclohexane-1-carboxylate

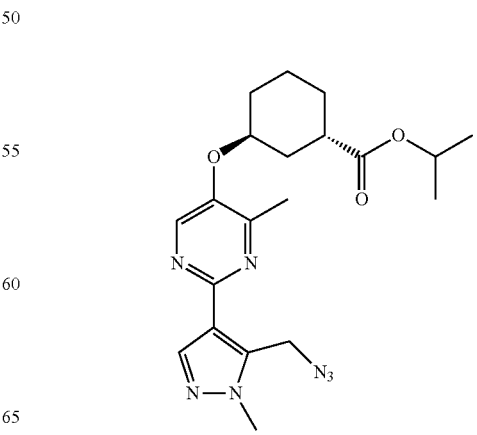

To a solution of Intermediate 2H (500 mg, 1.11 mmol) in DMF (2 mL) was added NaN$_3$ (72 mg, 1.11 mmol) and the reaction was stirred at 80° C. for 1 h; at this point LCMS analysis indicated the reaction was complete. The reaction mixture was cooled to RT, partitioned between EtOAc and water (10 mL each), and the resulting mixture was stirred at RT for 15 min. The organic layer was dried (Na$_2$SO$_4$) and concentrated in vacuo. The crude product was chromatographed (24 g SiO$_2$; continuous gradient from 0% to 100% EtOAc in hexane over 12 min) to afford the title compound (368 mg, 0.890 mmol, 80% yield) as a colorless oil. LCMS, [M+H]$^+$=414.3. $^1$H NMR (500 MHz, CDCl$_3$) δ 8.25 (s, 1H), 8.14 (s, 1H), 5.09-5.03 (m, 1H), 5.02 (s, 2H), 4.74 (dp, J=5.2, 2.7 Hz, 1H), 3.96 (s, 3H), 2.78 (tq, J=8.0, 4.1 Hz, 1H), 2.52 (s, 3H), 2.15-1.57 (m, 8H), 1.27 (dd, J=6.3, 2.5 Hz, 6H).

Intermediate 2

A solution of Intermediate 2I (128 mg; 0.31 mmol) and Ph$_3$P (81 mg, 0.31 mmol) in THF (2 mL) and H$_2$O (0.7 mL) was stirred at RT overnight; at this point LCMS analysis indicated the reaction was complete. EtOAc/water were added, and the mixture was stirred at RT for 15 min. The organic layer was dried (Na$_2$SO$_4$) and concentrated in vacuo. The residue was chromatographed (12 g SiO$_2$; continuous gradient from 0% to 10% MeOH in CH$_2$Cl$_2$ for 20 min; flow rate=30 mL/min) to give the title compound (97 mg, 0.25 mmol, 81% yield) as a light brown oil. [M+H]$^+$= 388.2.

Intermediate 3. Isopropyl (1S,3S)-3-((2-(5-formyl-1-methyl-1H-pyrazol-4-yl)-4-methylpyrimidin-5-yl)oxy) cyclohexane-1-carboxylate

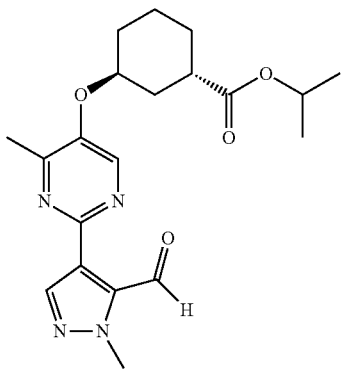 [SMILES: Cc1nc(-c2cnn(C)c2C=O)ncc1O[C@H]1CCC[C@H](C(=O)OC(C)C)C1]

Intermediate 3A. 1-methyl-4-(4,4,5,5-tetramethyl-1,3,2-dioxaborolan-2-yl)-1H-pyrazole-5-carbaldehyde

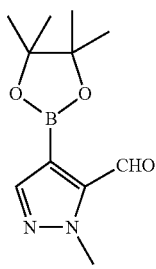 [SMILES: Cn1ncc(B2OC(C)(C)C(C)(C)O2)c1C=O]

A mixture of 4-bromo-1-methyl-1H-pyrazole-5-carbaldehyde (2.50 g, 13.23 mmol), bis(pinacolato)diboron (5.04 g, 19.8 mmol), KOAc (3.89 g, 39.7 mmol) and PdCl$_2$(dppf) (0.484 g, 0.661 mmol) in 1,4-dioxane (50 mL) was degassed and then heated at 80° C. under N$_2$ for 18 h, then was cooled to RT. The reaction mixture was diluted with EtOAc, then was filtered and concentrated in vacuo. The residue was chromatographed (80 g SiO$_2$; continuous gradient from 0% to 50% EtOAc in Hexane over 20 min) to give the title compound (3.0 g, 12.7 mmol, 96% yield) as a white solid. $^1$H NMR (400 MHz, CDCl$_3$) δ 10.27 (s, 1H), 7.78 (s, 1H), 4.19 (s, 3H), 1.34 (s, 12H); $^{11}$B NMR (128 MHz, CDCl$_3$) δ 29.2 (br s, 1B).

Intermediate 3B. 2-chloro-5-methoxy-4-methylpyrimidine

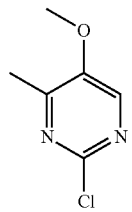

A degassed mixture of 2,4-dichloro-5-methoxypyrimidine (5.70 g, 31.8 mmol), trimethyl-boroxine (5.34 mL, 38.2 mmol) and K$_3$P$_4$ (13.52 g, 63.7 mmol) in THF (50 mL) was stirred at 65° C. for 16 h, then was cooled to RT. The reaction mixture was partitioned between EtOAc and water. The aqueous phase was extracted with EtOAc (2×); the combined organic extracts were dried (MgSO$_4$) and concentrated in vacuo. The crude product was chromatographed (220 g SiO$_2$; continuous gradient from 0% to 30% EtOAc in Hexane over 25 min) to give the title compound (1.6 g, 10.3 mmol, 32.3%) as a white solid. $^1$H NMR (500 MHz, CDCl$_3$) δ 8.05 (s, 1H), 3.92 (s, 3H), 2.45 (s, 3H).

Intermediate 3C. 2-chloro-4-methylpyrimidin-5-ol

To a −78° C. solution of Intermediate 3B (1.60 g, 10.09 mmol) in DCM (20 mL) was added BBr$_3$ (3.82 mL, 40.4 mmol) dropwise. The reaction mixture was allowed to slowly warm to RT and stirred for 16 h at RT, then was cautiously quenched with satd aq. NaHCO$_3$ (pH adjusted to ~4) and partitioned between EtOAc and water. The aqueous phase was extracted with EtOAc (2×), and the combined organic layers were dried (MgSO$_4$) and concentrated in vacuo. The crude product was chromatographed (40 g SiO$_2$; continuous gradient from 0-100% EtOAc in Hexane over 15 min) to afford the title compound (1.33 g, 9.20 mmol, 91% yield) as a white solid. $^1$H NMR (400 MHz, DMSO-d$_6$) 10.63 (s, 1H), 8.11 (s, 1H), 2.34 (s, 3H).

Intermediate 3D. Isopropyl (1S,3S)-3-((2-chloro-4-methylpyrimidin-5-yl)oxy)cyclohexane-1-carboxylate

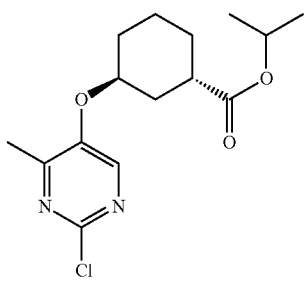 [SMILES: Cc1nc(Cl)ncc1O[C@H]1CCC[C@H](C(=O)OC(C)C)C1]

To a solution of Intermediate 3C (1.30 g, 9.0 mmol), isopropyl (1S,3R)-3-hydroxycyclohexane-1-carboxylate (3.01 g, 16.2 mmol) and Bu$_3$P (4.44 mL, 18.0 mmol) in 1,4-dioxane (50 mL) was added (E)-diazene-1,2-diylbis(piperidin-1-ylmethanone) (4.54 g, 18.0 mmol) at RT. The reaction mixture was stirred at 75° C. for 3 days, then was cooled to RT and filtered. The filtrate was concentrated in vacuo. The residue was chromatographed (80 g SiO$_2$; continuous gradient from 0% to 30% EtOAc in Hexane over 25 min) to give the title compound (1.72 g, 5.50 mmol, 61.1% yield) as a clear oil. $^1$H NMR (500 MHz, CDCl$_3$) δ 8.14 (s, 1H), 5.04 (spt, J=6.2 Hz, 1H), 4.71 (br d, J=2.2 Hz, 1H), 2.75 (tt, J=8.9, 4.3 Hz, 1H), 2.49 (s, 3H), 2.10-1.84 (m, 4H), 1.78-1.59 (m, 4H), 1.26 (dd, J=6.2, 2.9 Hz, 6H).

Intermediate 3

A mixture of bis(di-tert-butyl(4-dimethylaminophenyl)phosphine)dichloro-palladium(II) [(Pd(amphos)Cl$_2$); 0.204 g, 0.288 mmol], Intermediate 3A (1.630 g, 6.91 mmol), Intermediate 3D (1.72 g, 5.50 mmol) and aq. 2M Na$_2$CO$_3$ (8.63 mL, 17.3 mmol) in MeCN (50 mL) was degassed. The reaction mixture was microwaved at 120° C. for 1.5 h, then was cooled to RT. The reaction mixture was diluted with satd aq. NaHCO$_3$, and extracted with EtOAc (3×). The combined organic extracts were washed with brine, dried (Na$_2$SO$_4$), and concentrated in vacuo. The crude product was chromatographed (80 g SiO$_2$; continuous gradient from 0%-50% EtOAc in hexanes over 25 min) to give the title compound (1.0 g, 2.59 mmol, 45% yield) as an oil. [M+H]$^+$=387.2; 1H NMR (400 MHz, CDCl$_3$) δ 10.88 (s, 1H), 8.26 (s, 1H), 8.11 (s, 1H), 5.03 (spt, J=6.2 Hz, 1H), 4.80-4.72 (m, 1H), 4.22 (s, 3H), 2.82-2.71 (m, 1H), 2.50 (s, 3H), 2.14-1.87 (m, 4H), 1.80-1.57 (m, 4H), 1.25 (dd, J=6.3, 1.9 Hz, 6H).

Intermediate 4. 5-Isopentyl-1,2,4-oxadiazol-3-amine

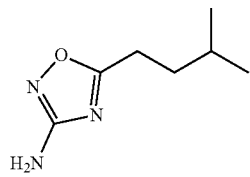

To a 0° C. suspension of NaNHCN (sodium hydrogencyanamide; 1.43 g, 22.3 mmol) in THF (14.9 mL) was added dropwise 4-methylpentanoyl chloride (1 mL, 7.43 mmol). The reaction was allowed to warm to RT and stirred for 18 h at RT, then was concentrated in vacuo. The resulting yellow solid was dissolved in water (20 mL) and the basic solution was adjusted to pH 6.5 with 10% aq. HCl. The mixture was extracted with EtOAc (2×20 mL). The aqueous layer was acidified to pH 1.5 with 10% aq. HCl and extracted with DCM (3×20 ml). The combined organic extracts were dried (Na$_2$SO$_4$) and concentrated in vacuo to give N-cyano-4-methylpentanamide (0.95 g, 91%) as a colorless liquid.

To a RT solution of N-cyano-4-methylpentanamide (0.95 g, 6.78 mmol) in EtOH (10 mL) was added NH$_2$OH.HCl (0.706 g, 10.2 mmol), followed by pyridine (2.19 mL, 27.1 mmol). The reaction was stirred at RT for 18 h, then was concentrated in vacuo. The residue was partitioned between DCM and water. The aqueous layer was extracted with DCM (2×). The combined organic extracts were dried (Na$_2$SO$_4$) and concentrated in vacuo to afford the title compound (0.89 g, 85%) as a white solid. LC-MS, [M+H]$^+$*=156.1. $^1$H NMR (500 MHz, CDCl$_3$) δ 4.51 (br s, 2H), 2.86-2.68 (m, 2H), 1.76-1.55 (m, 3H), 0.96 (d, J=6.3 Hz, 6H).

Intermediate 5. 3-(4-(((1S,3S)-3-(isopropoxycarbonyl)cyclohexyl)oxy)phenyl)-1,5-dimethyl-1H-pyrazole-4-carboxylic acid

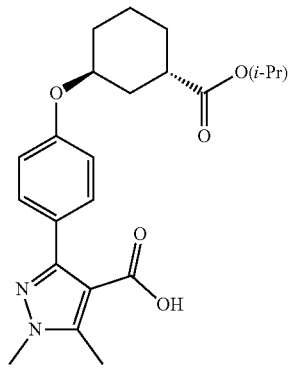

Intermediate 5A. Methyl 1,5-dimethyl-1H-pyrazole-4-carboxylate

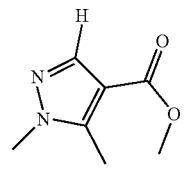

To a 0° C. solution of 1,5-dimethyl-1H-pyrazole-4-carboxylic acid (1.0 g, 7.14 mmol) in DCM/MeOH (7 mL each) was added 2M TMSCHN$_2$ in hexane (4.28 mL, 8.56 mmol). The reaction mixture was stirred at 0° C. for 1 h, then was allowed to warm to RT and stirred at RT overnight, then was concentrated in vacuo. The crude product was chromatographed (80 g SiO$_2$; continuous gradient from 0% to 50%

EtOAc in hexane over 20 min) to give the title compound (900 mg, 5.84 mmol, 82% yield). LCMS, [M+H]+=155.2.

Intermediate 5B. Methyl 3-bromo-1,5-dimethyl-1H-pyrazole-4-carboxylate

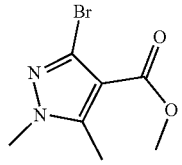

To a solution of Intermediate 5A (1.10 g, 7.14 mmol) in MeCN (14.3 mL) was added HOAc (4.1 mL, 71.4 mmol) and Br$_2$ (0.44 mL, 8.56 mmol). The reaction mixture was stirred at RT for 16 h, then was washed with satd aq. sodium thiosulfate (20 mL) and extracted with EtOAc (3×20 mL). The combined organic extracts were dried (MgSO$_4$), concentrated in vacuo. The crude product was chromatographed (80 g SiO$_2$; continuous gradient from 0% to 50% EtOAc in hexane over 20 min) to give the title compound (400 mg, 25%). $^1$H NMR (400 MHz, CDCl$_3$) δ 3.79-3.71 (m, 3H), 3.68-3.60 (m, 3H), 2.45-2.33 (m, 3H).

Intermediate 5C. Isopropyl (1S,3S)-3-(4-bromophenoxy)cyclohexane-1-carboxylate

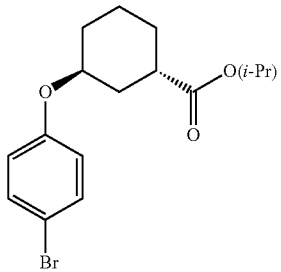

To a solution of 4-bromophenol (500 mg, 2.89 mmol) and isopropyl (1S,3R)-3-hydroxycyclohexane-1-carboxylate (538 mg, 2.89 mmol) in toluene (5.8 mL) were successively added dropwise Bu$_3$P (2.20 mL, 8.67 mmol) and (E)-diazene-1,2-diylbis (piperidin-1-ylmethanone) (2.20 g, 8.67 mmol). The reaction mixture was heated at 50° C. for 2 h, then was cooled to RT. Hexane (6 mL) was added to the mixture; a white solid precipitated which was filtered off. The filtrate was concentrated in vacuo. The crude product was chromatographed (80 g SiO$_2$; continuous gradient from 0% to 50% EtOAc in hexanes over 20 min) to give the title compound (400 mg, 1.17 mmol, 40.6% yield). $^1$H NMR (400 MHz, CDCl$_3$) δ 7.28-7.20 (m, 21), 6.75-6.64 (m, 2H), 4.95-4.82 (m, 1H), 4.52-4.38 (m, 1H), 2.73-2.58 (m, 1H), 2.16-2.01 (m, 2H), 1.98-1.67 (m, 2H), 1.64-1.49 (m, 4H), 1.19-1.04 (m, 6H).

Intermediate 5D. Isopropyl (1S,3S)-3-(4-(4,4,5,5-tetramethyl-1,3,2-dioxaborolan-2-yl) phenoxy)cyclohexane-1-carboxylate

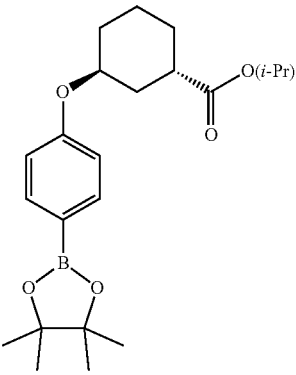

To a mixture of intermediate 5C (1.3 g, 3.8 mmol), bis-pinacolato diboron (1.5 g, 5.8 mmol), KOAc (1.15 g, 12 mmol) in 1,4-dioxane (8 mL) was added Xphos Pd G2 precatalyst (76 mg, 0.096 mmol) at RT. The mixture was heated at 80° C. for 16 h, then was cooled to RT and washed with satd aq. NaHCO$_3$ (20 mL) and extracted with EtOAc (3×20 mL). The combined organic extracts were dried (Na$_2$SO$_4$) and concentrated in vacuo. The crude product was chromatographed (80 g SiO$_2$; continuous gradient from 0% to 50% EtOAc in hexane over 20 min) to give the title compound (1.00 g, 67%). $^1$H NMR (400 MHz, CDCl$_3$) δ 7.81-7.71 (m, 2H), 7.00-6.88 (m, 2H), 5.09-4.96 (m, 1H), 4.74-4.62 (m, 1H), 2.89-2.73 (m, 1H), 2.11-2.04 (m, 1H), 1.97-1.86 (m, 2H), 1.80-1.70 (m, 1H), 1.67-1.59 (m, 2H), 1.40-1.34 (m, 12H), 1.32-1.28 (m, 2H), 1.27-1.21 (m, 6H).

Intermediate 5E. Methyl 3-(4-(((1S,3S)-3-(isopropoxycarbonyl)cyclohexyl)oxy)phenyl)-1,5-dimethyl-1H-pyrazole-4-carboxylate

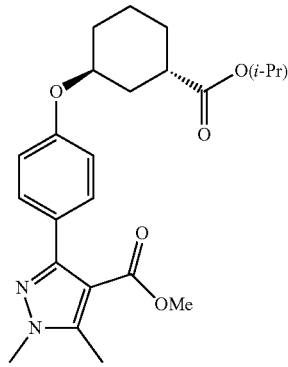

A mixture of Intermediate 5D (32 mg, 0.082 mmol), Intermediate 5B (19 mg, 0.082 mmol), and bis(di-tert-butyl (4-dimethylaminophenyl)phosphine) dichloropalladium(II) (7 mg, 8 μmol) in MeCN (1 mL) and water (0.05 mL) was stirred at 100° C. in a microwave reactor for 1 h, then was cooled to RT. The reaction mixture was diluted with water (25 mL) and extracted with EtOAc (2×50 mL); the combined organic layers were washed with water and brine (50 mL each), dried (Na$_2$SO$_4$), and concentrated in vacuo. The crude product was chromatographed (12 g SiO$_2$; continuous gradient from 0% to 50% EtOAc in hexane over 10 min) to give the title compound (20 mg, 0.048 mmol, 59.2% yield) as a clear oil. $^1$H NMR (400 MHz, CDCl$_3$) δ 7.61-7.46 (m, 2H), 7.08-6.85 (m, 2H), 5.14-4.94 (m, 1H), 4.73-4.58 (m, 1H), 3.90-3.82 (m, 3H), 3.81-3.70 (m, 3H), 2.88-2.74 (m, 1H), 2.62-2.48 (m, 3H), 2.17-2.03 (m, 1H), 1.97-1.87 (m, 3H), 1.84-1.72 (m, 1H), 1.65-1.53 (m, 3H), 1.33-1.20 (m, 6H).

Intermediate 5

A mixture of Intermediate 1E (60 mg, 0.145 mmol) and LiI (97 mg, 0.724 mmol) in DMF (0.5 mL) was heated in a microwave reactor at 180° C. for 30 min, then was cooled to RT and concentrated in vacuo. The residue was purified via preparative HPLC (C18 30×100 mm column; detection at 220 un; flow rate=40 mL/min; continuous gradient from 0% B to 100% B over 10 min+2 min hold time at 100% B, where A=90:10:0.1 H$_2$O:MeCN:TFA and B=90:10:0.1 MeCN:H$_2$O:TFA) to give the title compound (20 mg, 0.050 mmol, 34.5% yield). LCMS, [M+H]$^+$=401.2.

Example 1. (1S,3S)-3-((4-methyl-2-(1-methyl-5-(((2-phenyl-2H-1,2,3-triazol-4-yl)amino)methyl)-1H-pyrazol-4-yl)pyrimidin-5-yl)oxy)cyclohexane-1-carboxylicacid

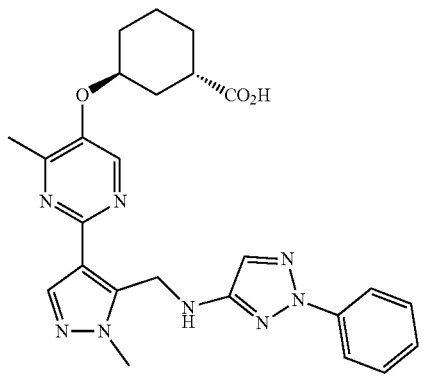 [SMILES: Cc1nc(-c2cnn(C)c2CNc2cnn(-c3ccccc3)n2)ncc1O[C@H]1CCC[C@H](C(=O)O)C1]

To a solution of Intermediate 3 (30 mg, 0.078 mmol) and 2-phenyl-2H-1,2,3-triazol-4-amine (19 mg, 0.12 mmol) in DCM (0.5 mL) was added NaBH(OAc)$_3$ (33 mg, 0.16 mmol) and TFA (0.012 mL, 0.16 mmol) portionwise. The reaction mixture was stirred for 18 h at RT. NaBH$_4$ (20 mg, 0.529 mmol) and MeOH (1 mL) were added and the reaction was stirred at RT for 24 h, then was concentrated in vacuo. The residue was dissolved in DCM and washed with 1N aq. NaOH and then concentrated in vacuo. The residue was stirred with 1N aq. NaOH (0.1 mL) in MeOH (1 mL) at RT for 18 h, then was concentrated in vacuo. The crude product was purified by preparative HPLC (Sunfire C18 30×100 mm column; detection at 220 nm; flow rate=40 mL/min; continuous gradient from 30% B to 100% B over 10 min+2 min hold time at 100% B, where A=90:10:0.1 H$_2$O:MeCN:TFA and B=90:10:0.1 MeCN:H$_2$O:TFA) to give the title compound (bis-TFA salt; 18 mg, 0.025 mmol, 31.7% yield) as a clear oil. [M+H]$^+$=489.2; 1H NMR (400 MHz, CDCl$_3$) δ 8.51 (s, 1H), 8.22 (s, 1H), 7.93-7.80 (m, 2H), 7.51-7.36 (m, 2H), 7.30-7.22 (m, 1H), 7.20 (s, 1H), 4.83-4.73 (m, 3H), 4.19 (s, 3H), 2.95-2.83 (m, 1H), 2.59 (s, 3H), 2.22-1.58 (m, 8H). hLPA$_1$ IC$_{50}$=35 nM.

Example 2. (1S,3S)-3-((2-(5-(((3-isopropyl-1,2,4-thiadiazol-5-yl)amino)methyl)-1-methyl-1H-pyrazol-4-yl)-4-methylpyrimidin-5-yl)oxy)cyclohexane-1-carboxylic acid

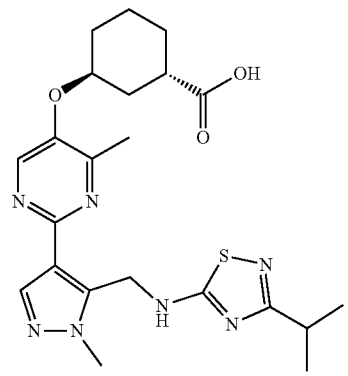 [SMILES: Cc1nc(-c2cnn(C)c2CNc2nc(C(C)C)ns2)ncc1O[C@H]1CCC[C@H](C(=O)O)C1]

2A. Isopropyl (1S,3S)-3-((4-methyl-2-(1-methyl-5-(((tetrahydro-2H-pyran-2-yl)oxy)methyl)-1H-pyrazol-4-yl)pyrimidin-5-yl)oxy)cyclohexane-1-carboxylate

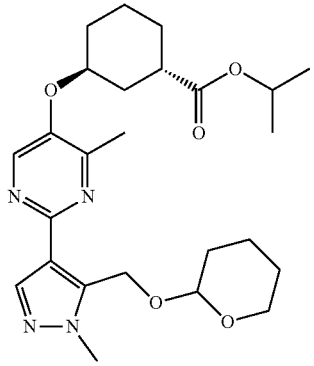 [SMILES: Cc1nc(-c2cnn(C)c2COC2CCCCO2)ncc1O[C@H]1CCC[C@H](C(=O)OC(C)C)C1]

A mixture of bis(di-tert-butyl(4-dimethylaminophenyl)phosphine)dichloro-palladium(II) (Pd(amphos)Cl$_2$); 0.267 g, 0.377 mmol), Intermediate 2C (4.86 g, 45% pure, 6.79 mmol), Intermediate 3D (1.18 g, 3.77 mmol) and aq. 2M Na$_2$CO$_3$ (5.66 mL, 11.3 mmol) in MeCN (10 mL) was sealed, evacuated and recharged with N$_2$ (3 times). The reaction was microwaved at 120° C. for 1.5 h, then was cooled to RT, diluted with satd aq. NaHCO$_3$ (10 mL), and extracted with EtOAc (3×10 mL). The combined organic extracts were washed with brine, dried (Na$_2$SO$_4$), and concentrated in vacuo. The crude product was chromatographed (220 g SiO$_2$, continuous gradient from 0% to 100% EtOAc in hexanes over 25 min, then hold for 10 min) to provide the title compound (463 mg, 0.968 mmol, 25.7% yield) as a slightly colored oil. LCMS, [M+H]$^+$=473.3. $^1$H NMR (500 MHz, DMSO-d$_6$) δ 8.39 (s, 1H), 7.90 (s, 1H), 5.28 (d, J=11.9 Hz, 1H), 5.06 (d, J=12.0 Hz, 1H), 4.89 (p, J=6.2 Hz, 1H), 4.80 (s, 1H), 4.73 (d, J=3.5 Hz, 1H), 3.88 (s, 3H), 3.79 (t, J=9.7 Hz, 1H), 3.48-3.40 (m, 1H), 2.70-2.61 (m, 1H), 2.40 (s, 3H), 2.01-1.38 (m, 14H), 1.17 (d, J=6.2 Hz, 6H).

2B. Isopropyl (1S,3S)-3-((2-(5-(hydroxymethyl)-1-methyl-H-pyrazol-4-yl)-4-methylpyrimidin-5-yl)oxy)cyclohexane-1-carboxylate

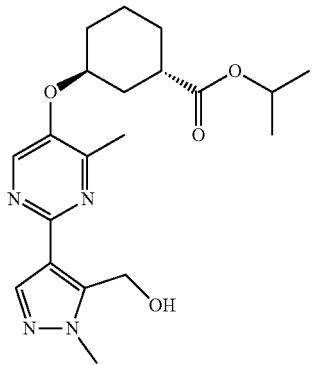 [SMILES: Cc1nc(-c2cnn(C)c2CO)ncc1O[C@H]1CCC[C@H](C(=O)OC(C)C)C1]

To a solution of 2A (463 mg, 0.98 mmol) in MeOH (5 mL) added PPTS (0.932 g, 3.71 mmol). The reaction mixture was heated to 60° C. for 2 h, then was cooled to RT, diluted with water and sat. aq. NaHCO₃, then was extracted with EtOAc (3×10 mL). The combined organic extracts were concentrated in vacuo and chromatographed (40 g SiO₂; continuous gradient from 0% to 100% EtOAc/hexanes over 12 min, then hold for 10 min) to give the title compound as a white solid (323 mg, 0.790 mmol, 81% yield). LCMS, [M+H]⁺=389.3. 1H NMR (500 MHz, DMSO-d6) δ 8.43 (s, 1H), 7.88 (s, 1H), 5.48 (t, J=5.7 Hz, 1H), 5.00 (d, J=5.8 Hz, 2H), 4.90 (p, J=6.3 Hz, 1H), 4.82 (s, 1H), 3.90 (s, 3H), 2.67 (d, J=10.3 Hz, 1H), 2.42 (s, 3H), 2.04-1.44 (m, 8H), 1.18 (d, J=6.2 Hz, 6H).

2C. Isopropyl (1S,3S)-3-((2-(5-(bromomethyl)-1-methyl-H-pyrazol-4-yl)-4-methylpyrimidin-5-yl)oxy)cyclohexane-1-carboxylate

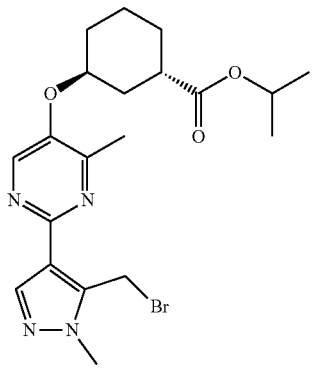 [SMILES: Cc1nc(-c2cnn(C)c2CBr)ncc1O[C@H]1CCC[C@H](C(=O)OC(C)C)C1]

To a 0° C. solution of 2B (423 mg, 1.089 mmol) in DCM (15 mL) was added PBr₃ (0.15 mL, 1.63 mmol). The reaction was stirred overnight at RT, then was cooled to 0° C. and neutralized with satd aq. NaHCO₃ to pH 7. The mixture was partitioned between DCM (20 mL) and water (10 mL), and the aqueous layer was extracted with DCM (3×10 mL). The combined organic extracts were dried (MgSO₄) and concentrated in vacuo. The residue was chromatographed (24 g SiO₂; continuous gradient from 0% to 100% of EtOAc/hexanes over 12 min) to give the title compound (450 mg, 0.997 mmol, 92% yield) as a white solid. LCMS, [M+H]⁺=451.2. ¹H NMR (400 MHz, CDCl₃) δ 8.26 (s, 1H), 8.11 (s, 1H), 5.24 (s, 2H), 5.05 (hept, J=6.3 Hz, 1H), 4.74 (dp, J=5.1, 2.7 Hz, 1H), 3.97 (s, 3H), 2.78 (tt, J=9.8, 4.0 Hz, 1H), 2.52 (s, 3H), 2.16-1.56 (m, 8H), 1.27 (dd, J=6.2, 2.2 Hz, 6H).

2D. Isopropyl (1S,3S)-3-((2-(5-(aminomethyl)-1-methyl-1H-pyrazol-4-yl)-4-methylpyrimidin-5-yl)oxy)cyclohexane-1-carboxylate

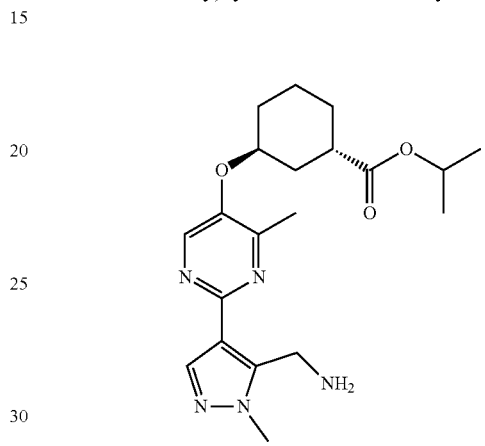

To a solution of 2C (338 mg, 0.817 mmol) in THF (6 mL) and H₂O (2.0 mL) was added Ph₃P (257 mg, 0.981 mmol). The reaction was stirred at RT overnight, then was taken up in EtOAc and water (10 mL each). The resulting mixture was stirred at RT for 15 min; the aqueous layer was extracted with EtOAc (3×5 mL). The combined organic extracts were dried (Na₂SO₄) and concentrated in vacuo. The residue was chromatographed (12 g SiO₂; 100% EtOAc for 10 min, then a continuous gradient from 0% to 75% MeOH in EtOAc over 4 min, and hold for 75% MeOH/EtOAc for 10 min; flow rate=30 mL/min) to give the title compound (269 mg, 0.694 mmol, 85% yield) as a sticky yellow oil. LCMS, [M+H]⁺=388.3. ¹H NMR (500 MHz, CD₃CN) δ 8.28 (s, 1H), 7.90 (s, 1H), 4.97 (hept, J=6.2 Hz, 1H), 4.73 (dp, J=5.4, 2.8 Hz, 1H), 4.09 (br s, 2H), 3.88 (s, 3H), 2.75 (tt, J=9.9, 4.0 Hz, 1H), 2.44 (s, 3H), 2.11-1.53 (m, 8H), 1.22 (d, J=6.3 Hz, 6H).

Example 2

To a solution of 2D (8 mg, 0.02 mmol) in n-BuOH (0.5 mL) was added 5-chloro-3-isopropyl-1,2,4-thiadiazole (5 mg, 0.03 mmol) and iPr₂NEt (11 μL, 0.06 mmol). The mixture was heated in a microwave reactor at 180° C. for 120 min, then was cooled to RT. THF (0.5 mL)/H₂O (0.5 mL)/MeOH (0.5 mL) and LiOH.H₂O (4 mg, 0.1 mmol) were added to the reaction mixture, which was stirred at RT overnight. Volatiles were removed in vacuo and the residue was diluted with H₂O (2 mL). The mixture was adjusted with 1N aq. HCl to pH ~5 and extracted with EtOAc (3×3 mL). The combined organic extracts were washed with brine (2 mL), dried (MgSO₄) and concentrated in vacuo. The crude product was purified by preparative LC/MS: Column: XBridge C18, 200 mm×19 mm, 5-μm particles; Mobile Phase A: 5:95 MeCN:H₂O with 0.1% TFA; Mobile Phase B:

95:5 MeCN:H₂O with 0.1% TFA; Gradient: a 0-min hold at 24% B, 24-64% B over 20 min, then a 4-min hold at 100% B; Flow Rate: 20 mL/min; Column Temperature: 25° C. Fractions containing the desired product were combined and dried via centrifugal evaporation to give the title compound (5 mg, 33% yield; 97% purity by LC/MS). LCMS, [M+H]⁺= 472.2. ¹H NMR (500 MHz, DMSO-d) 8.40 (s, 1H), 7.91 (s, 1H), 5.02 (d, J=5.0 Hz, 2H), 4.81 (s, 1H), 3.98 (s, 3H), 2.84 (p, J=6.9 Hz, 1H), 2.66-2.58 (m, 1H), 2.40 (s, 3H), 2.03-1.40 (m, 8H), 1.14 (d, J=6.9 Hz, 6H). hLPA₁ IC₅₀=1857 nM.

Example 3. (1S,3S)-3-((4-methyl-2-(1-methyl-5-((3-propyl-1,2,4-thiadiazol-5-yl)amino)-1H-pyrazol-4-yl)pyrimidin-5-yl)oxy)cyclohexane-1-carboxylic acid

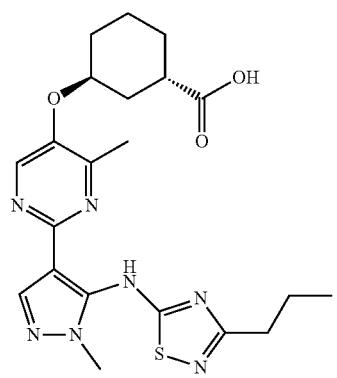 [SMILES: CCCc1nsc(Nc2c(-c3ncc(O[C@H]4CCC[C@H](C(=O)O)C4)c(C)n3)cnn2C)n1]

3A. Isopropyl (1S,3S)-3-((2-bromo-4-methylpyrimidin-5-yl)oxy)cyclohexane-1-carboxylate

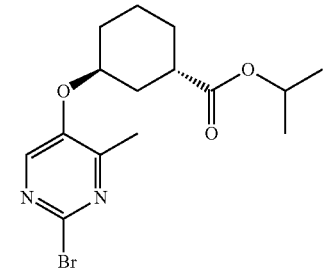 [SMILES: Cc1nc(Br)ncc1O[C@H]1CCC[C@H](C(=O)OC(C)C)C1]

A mixture of (E)-diazene-1,2-diylbis(piperidin-1-yl-methanone) (3.47 g, 13.8 mmol), toluene (30 mL) and Bu₃P (3.44 mL, 13.76 mmol) in a pressure vial was stirred at RT for 30 min, after which 2-bromo-4-methylpyrimidin-5-ol (1.30 g, 6.9 mmol) and isopropyl (1S,3R)-3-hydroxycyclohexane-1-carboxylate (2.31 g, 12.4 mmol) were successively added. The reaction mixture was heated to 85° C. for 9 h, then was cooled to RT and diluted with DCM (10 mL), filtered and concentrated in vacuo. The crude oily product was chromatographed (120 g SiO₂; continuous gradient from 0% to 90% EtOAc in hexane over 25 min, hold at 90% EtOAc for 20 min) to provide the title compound (1.80 g, 5.04 mmol, 73% yield) as a light yellow oil. ¹H NMR (500 MHz, DMSO-d₆) δ 8.32 (d, J=3.7 Hz, 1H), 4.90 (p, J=6.4 Hz, 1H), 4.80 (s, 1H), 2.70-2.59 (m, 1H), 2.38 (s, 3H), 2.01-1.46 (m, 8H), 1.18 (d, J=6.3 Hz, 6H). [M+H]⁺=357.

3B. tert-butyl 1-methyl-4-(4,4,5,5-tetramethyl-1,3,2-dioxaborolan-2-yl)-1H-pyrazole-5-carboxylate

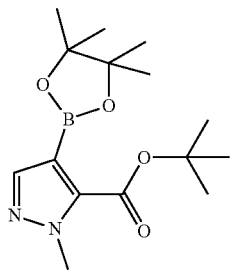 [SMILES: Cn1ncc(B2OC(C)(C)C(C)(C)O2)c1C(=O)OC(C)(C)C]

Ar was vigorously bubbled through a stirred mixture of 3A (1.50 g, 5.74 mmol), KOAc (1.69 g, 17.2 mmol) and B₂pin₂ (2.19 g, 8.62 mmol) in 1,4-dioxane (20 mL) for 5 min, followed by addition of Pd(dppf)Cl₂—CH₂Cl₂ (0.47 g, 0.57 mmol). The reaction mixture was flushed with Ar, then was heated to 100° C. for 16 h. LCMS analysis at this point indicated that the reaction was complete. The reaction mixture was cooled to RT; CH₂Cl₂ and H₂O were added (20 mL each) and the resulting mixture was stirred vigorously. The organic layer was dried (Na₂SO₄) and concentrated in vacuo to give the crude title compound, which was used in the next step without further purification. [M+H]⁺=309.2.

3C. Tert-butyl 4-(5-(((1S,3S)-3-(isopropoxycarbonyl)cyclohexyl)oxy)-4-methylpyrimidin-2-yl)-1-methyl-1H-pyrazole-5-carboxylate

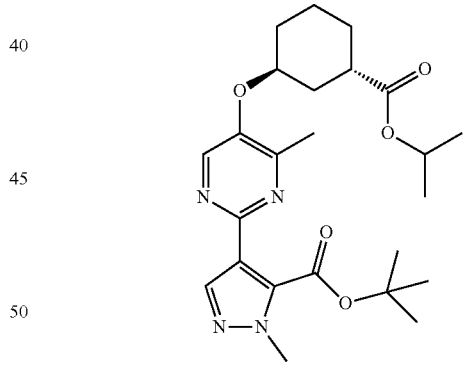

A mixture of bis(di-tert-butyl(4-dimethylaminophenyl)phosphine)dichloro-palladium (II) (0.169 g, 0.239 mmol), 3B (0.884 g, 2.87 mmol) and 3A (0.854 g, 2.392 mmol) in aq. 2M Na₂CO₃ (5.98 mL, 12.0 mmol) and MeCN (12 mL) was heated at 100° C. in a microwave reactor for 1 h, then was cooled to RT. The mixture was diluted with satd aq. NaHCO₃ and extracted with EtOAc (3×10 mL). The combined organic extracts were washed with brine, dried (Na₂SO₄), and concentrated in vacuo. The crude product was chromatographed (80 g SiO₂, continuous gradient from 0%-90% EtOAc:hexanes) to provide the title compound (1.08 g, 2.36 mmol, 98% yield) as a beige solid. [M+H]⁺= 459.3.

3D. 4-(5-(((1S,3S)-3-(isopropoxycarbonyl)cyclohexyl)oxy)-4-methylpyrimidin-2-yl)-1-methyl-1H-pyrazole-5-carboxylic acid

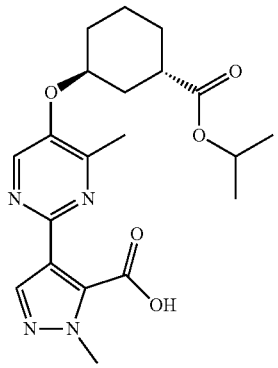 [SMILES: Cc1nc(-c2cnn(C)c2C(=O)O)ncc1O[C@H]1CCC[C@H](C(=O)OC(C)C)C1]

To a solution of 3C (1.08 g, 2.355 mmol) in DCM (20 mL) was added TFA (9.07 mL, 118 mmol) dropwise. The reaction was stirred at RT for 20 h, then was concentrated in vacuo to afford the crude title compound (1.20 g, 2.89 mmol, >100% yield) as a colored oil, which was used in the next step without further purification. $^1$H NMR (500 MHz, DMSO-d$_6$) δ 8.62 (s, 1H), 8.14 (s, 1H), 4.94-4.87 (m, 2H), 4.12 (s, 3H), 2.72-2.62 (m, 1H), 2.49 (s, 3H), 2.08-1.44 (m, 8H), 1.19 (dd, J=6.4, 1.9 Hz, 6H). [M+H]$^+$=403.2.

3E. Isopropyl (1S,3S)-3-((2-(5-((tert-butoxycarbonyl)amino)-1-methyl-H-pyrazol-4-yl)-4-methylpyrimidin-5-yl)oxy)cyclohexane-1-carboxylate

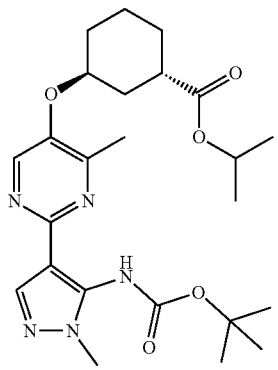 [SMILES: Cc1nc(-c2cnn(C)c2NC(=O)OC(C)(C)C)ncc1O[C@H]1CCC[C@H](C(=O)OC(C)C)C1]

A mixture of crude 3D (600 mg, 1.49 mmol), (PhO)$_2$PON$_3$ (0.58 mL, 2.68 mmol), tert-butyl alcohol (331 mg, 2.23 mmol), Et$_3$N (0.83 mL, 5.95 mmol) in toluene (3 mL) was stirred at 80° C. for 2 h, then was cooled to RT and concentrated in vacuo. The crude product was chromatographed (80 g SiO$_2$; continuous gradient from 0% to 100% EtOAc:hexane over 25 min) to afford the title compound (248 mg, 0.524 mmol, 35.2% yield) as a colorless oil. $^1$H NMR (500 MHz, CDCl$_3$) (about 1: rotamers) δ 8.71 (s, 1H), 8.23 (s, 0.5H), 8.04 (s, 0.5H), 5.05 (p, J=6.3 Hz, 1H), 4.76 (s, 0.5H), 4.72 (s, 0.5H), 3.89 (s, 3H), 2.82-2.72 (m, 1H), 2.51 (br s, 3H), 2.15-1.47 (m, 8H), 1.27 (br s, 15H). [M+H]$^+$=474.3.

3F. Isopropyl (1S,3S)-3-((2-(5-amino-1-methyl-H-pyrazol-4-yl)-4-methylpyrimidin-5-yl)oxy)cyclohexane-1-carboxylate To a solution of 3E (238 mg, 0.503 mmol) in DCM (5 mL) was added TFA (3.87 mL, 50.3 mmol) dropwise at RT. The mixture was stirred at RT for 20 h, then was concentrated in vacuo, azeotroped with toluene (3×5 mL) and dried in vacuo for 24 h to afford the title compound (TFA salt; 220 mg, 0.561 mmol, 92% yield) as a slightly colored oil. $^1$H NMR (500 MHz, DMSO-d$_6$) δ 8.32 (s, 1H), 7.64 (s, 1H), 6.31 (s, 2H), 4.89 (p, J=6.2 Hz, 1H), 4.71 (s, 1H), 2.70-2.63 (m, 1H), 2.39 (s, 3H), 2.00-1.42 (m, 8H), 1.18 (d, J=6.2 Hz, 6H). (the protons of the —CH$_3$ group on pyrazole was not observed due to water-suppression). [M+H]$^+$=374.3.

Example 3

A solution of (9,9-dimethyl-9H-xanthene-4,5-diyl)bis(diphenylphosphane) (5 mg, 8.0 μmol), 3F (15 mg, 0.040 mmol), 5-chloro-3-propyl-1,2,4-thiadiazole (10 mg, 0.06 mmol), BINAP (5 mg, 8.0 μmol), Pd$_2$(dba)$_3$ (2 mg, 4 μmol) and Cs$_2$CO$_3$ (20 mg, 0.06 mmol) in toluene (1 mL) was heated in a sealed tube at 110° C. overnight, then was cooled to RT and concentrated in vacuo. The residue was dissolved in THF (0.5 mL), MeOH (0.5 mL), and H$_2$O (0.5 mL). LiOH.H$_2$O (17 mg, 0.4 mmol) was added and the reaction was stirred at RT for 14 h, then was concentrated in vacuo. The residue was taken up in EtOAc (2 mL)/H$_2$O (1 mL), and the solution was adjusted to pH ~5 with 1N aq. HCl. The mixture was extracted with EtOAc (3×2 mL); the combined organic extracts were dried (MgSO$_4$) and concentrated in vacuo. The residue was dissolved in DMF and purified via preparative LC/MS: Column: XBridge C18, 200 mm×19 mm, 5-μm particles; Mobile Phase A: 5:95 MeCN:H$_2$O with 10 mM NH$_4$OAc; Mobile Phase B: 95:5 MeCN:H$_2$O with 10 mM NH$_4$OAc; Gradient: a 0-min hold at 10% B, 10-50% B over 20 min, then a 4-min hold at 100% B; Flow Rate: 20 mL/min; Column Temperature: 25° C. Fractions containing the desired product were combined and dried via centrifugal evaporation to give the title compound (3.0 mg, 15% yield; 92% purity by LC-MS). LCMS, [M+H]$^+$=457.9. H NMR (500 MHz, DMSO-d6) δ 8.32 (s, 1H), 7.96 (s, 1H), 4.78 (s, 1H), 2.63-2.57 (m, 1H), 2.28 (s, 3H), 1.99-1.43 (m, 10H), 0.81 (t, J=7.4 Hz, 3H). (The N—CH$_3$ on pyrazole and the —CH$_2$ off the thiadiazole are not observed due to water-suppression). hLPA$_1$ IC$_{50}$=437 nM.

Example 4. (1S,3S)-3-((2-(5-(((5-isopentyl-1,2,4-oxadiazol-3-yl)amino)methyl)-1-methyl-1H-pyrazol-4-yl)-4-methylpyrimidin-5-yl)oxy)cyclohexane-1-carboxylic acid, bis TFA salt

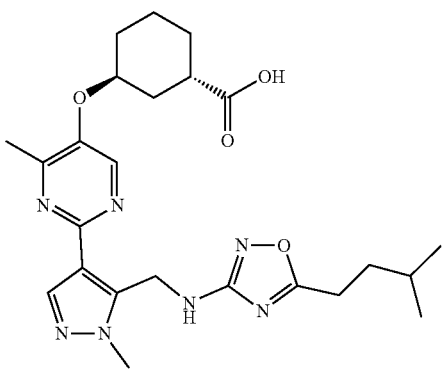 [SMILES: Cc1nc(-c2cnn(C)c2CNc2noc(CCC(C)C)n2)ncc1O[C@H]1CCC[C@H](C(=O)O)C1]

4A. Isopropyl (1S,3S)-3-((2-(5-(((5-isopentyl-1,2,4-oxadiazol-3-yl)amino)methyl)-1-methyl-1H-pyrazol-4-yl)-4-methylpyrimidin-5-yl)oxy)cyclohexane-1-carboxylate, 2 TFA

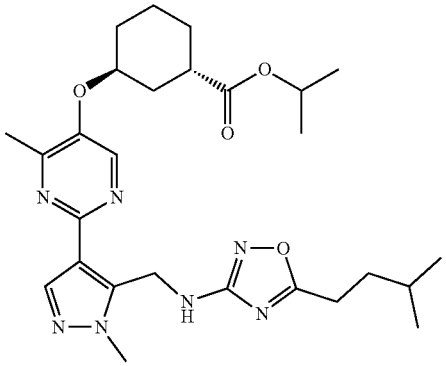 [SMILES: Cc1nc(-c2cnn(C)c2CNc2noc(CCC(C)C)n2)ncc1O[C@H]1CCC[C@H](C(=O)OC(C)C)C1]

To a solution of Intermediate 3 (30 mg, 0.078 mmol) and Intermediate 4 (12 mg, 0.078 mmol) in MeOH (1.1 mL) was added HOAc (0.022 mL, 0.388 mmol). The reaction was stirred in a sealed vial at 65° C. for 2 h, then was cooled to RT. NaBH$_3$CN (10 mg, 0.155 mmol) was added to the reaction mixture, which was stirred at RT for 18 h, then was quenched with sat aq. NaHCO$_3$. The aqueous layer was extracted with EtOAc. The organic layer was washed with brine, dried (Na$_2$SO$_4$) and concentrated in vacuo. The crude material was purified by preparative HPLC: Column: Sunfire Prep C18 OBD, 30×0.100 mm, 5-µm particles; Mobile Phase A: 10:90 MeCN:H$_2$O with 0.1% TFA; Mobile Phase B: 90:10 MeCN:H$_2$O with 0.1% TFA; Gradient: 20-100% B over 12 min, then a 3-min hold at 100% B; Flow: 40 mL/min. Fractions containing the desired product were combined and dried via centrifugal evaporation to afford the title compound (27 mg, 46%). LCMS, [M+H]$^+$=526.4.

Example 4

To a solution of 4A (27 mg, 0.036 mmol) in MeOH (1 mL) was added 1N aq. NaOH (0.36 mL, 0.36 mmol). The reaction mixture was stirred at RT for 18 h, then was adjusted with 1N aq. HCl to pH ~4 and extracted with EtOAc (3×5 mL). The combined organic extracts were washed with brine, dried (Na$_2$SO$_4$) and concentrated in vacuo. The crude material was purified by preparative LC/MS: Column: XBridge C18, 200 mm×19 mm, 5-µm particles; Mobile Phase A: 5:95 MeCN:H$_2$O with 0.1% TFA; Mobile Phase B: 95:5 MeCN:H$_2$O with 0.1% TFA; Gradient: a 0-min hold at 31% B, 31-71% B over 20 min, then a 4-min hold at 100% B; Flow Rate: 20 mL/min; Column Temperature: 25 C. Fractions containing the desired product were combined and dried via centrifugal evaporation to afford the title compound (16.9 mg, 63%). LC-MS, [M+H]$^+$=484.4. $^1$H NMR (500 MHz, DMSO-d$_6$) δ 8.44 (s, 1H), 7.90 (s, 1H), 4.83 (br s, 1H), 4.76 (br s, 2H), 3.92 (s, 3H), 2.71 (br t, J=7.3 Hz, 2H), 2.67-2.61 (m, 1H), 2.41 (s, 3H), 2.08-1.98 (m, 1H), 1.87-1.77 (m, 3H), 1.68-1.45 (m, 7H), 0.86 (br d, J=5.8 Hz, 6H). hLPA$_1$ IC$_{50}$=10 nM.

Example 9: (1S,3S)-3-((2-(5-((4-(cyclopropylmethyl)-1H-1,2,3-triazol-1-yl)methyl)-1-methyl-1H-pyrazol-4-yl)-4-methylpyrimidin-5-yl)oxy)cyclohexane-1-carboxylic acid

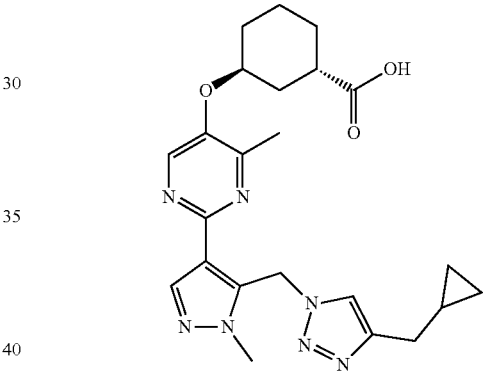

To a solution of azide Intermediate 2I (14.5 mg, 0.035 mmol) and prop-2-yn-1-yl cyclopropane (8.4 mg, 0.105 mmol) in tBuOH (175 µL)/water (175 µL) was added sodium ascorbate (1.4 mg, 7.01 µmol) and CuSO$_4$.5H$_2$O (0.9 mg, 3.51 µmol). The mixture was heated at 37° C. for 16 h, then was cooled to RT and concentrated in vacuo. The residue was dissolved in THF (0.5 mL), MeOH (0.5 mL), and water (0.5 mL). Aq. 4M UGH (88 µL, 0.351 mmol) was added and the reaction was stirred at RT for 14 h, then was concentrated in vacuo. The residue was taken up in EtOAc (2 mL)/water (1 mL), and the pH was adjusted to ~5 with 1N aq. HCl. The mixture was extracted with EtOAc (3×2 mL). The combined organic extracts were dried (MgSO$_4$) and concentrated in vacuo. The crude material was purified by preparative LC/MS (Column: XBridge C18, 200 mm×19 mm, 5-µm particles; Mobile Phase A: 5:95 MeCN:H$_2$O with 0.1% TFA; Mobile Phase B: 95:5 MeCN:H$_2$O with 0.1% TFA; Gradient: a 0-min hold at 18% B, 18-58% B over 20 min, then a 4-min hold at 100% B; Flow Rate: 20 mL/min; Column Temperature: 25° C.) to give the crude product. The material was further purified by preparative LC/MS: Column: XBridge C18,200 mm×19 mm, 5-µm particles; Mobile Phase A: 5:95 MeCN:H$_2$O with 10-mM aq. NH$_4$OAc; Mobile Phase B: 95:5 MeCN:H$_2$O with 10-mM aq. NH$_4$OAc; Gradient: a 0-min hold at 5% B, 5-45% B over 19 min, then a 5-min hold at 100% B; Flow Rate: 20 mL/min; Column Temperature: 25° C. Fraction collection was triggered by UV signals.

The material was further purified by preparative LC/MS (Column: XBridge C18, 200 mm×19 mm, 5-μm particles; Mobile Phase A: 5:95 MeCN:$H_2O$ with 10-mM $NH_4OAc$; Mobile Phase B: 95:5 MeCN:$H_2O$ with 10-mM $NH_4OAc$; Gradient: a 0-min hold at 20% B, 20-43% B over 25 min, then a 2-min hold at 100% B; Flow Rate: 20 mL/min; Column Temperature: 25° C. Fraction collection was triggered by UV signals. Fractions containing the desired product were combined and dried via centrifugal evaporation) to give the title compound (5.9 mg, 36% yield; LCMS purity=97%). $^1$H NMR (500 MHz, DMSO-$d_6$) δ 8.38 (s, 1H), 7.87 (s, 1H), 7.86 (s, 1H), 6.02 (s, 2H), 4.72 (s, 1H), 3.85 (s, 3H), 2.39 (d, J=7.9 Hz, 2H), 2.34 (s, 3H), 1.89-1.35 (m, 8H), 0.88-0.77 (m, 1H), 0.34-0.24 (m, 2H), 0.01 (d, J=4.8 Hz, 2H). (The proton α to the acid is not observed due to water-suppression). LCMS, [M+H]$^+$=451.9. hLPA$_1$ IC$_{50}$=636 nM.

The Examples in Table 1 below were synthesized according to the procedures described for the preparation of Examples 1 to 4 or 9.

TABLE 1

| Ex # | Structure & Name | Analytical & Biological Data | Method |
|---|---|---|---|
| 5 | 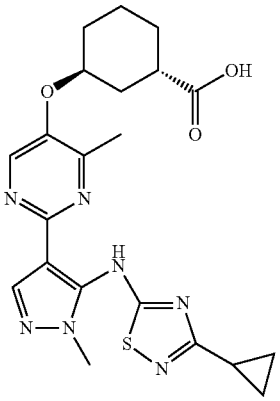<br>(1S,3S)-3-((2-(5-((3-cyclopropyl-1,2,4-thiadiazol-5-yl)amino)-1-methyl-1H-pyrazol-4-yl)-4-methylpyrimidin-5-yl)oxy)cyclohexane-1-carboxylic acid | LCMS, [M + H]$^+$ = 456.1; $^1$H NMR (500 MHz, DMSO-$d_6$) δ 8.32 (s, 1H), 7.95 (s, 1H), 4.78 (s, 1H), 2.64-2.57 (m, 1H), 2.28 (s, 3H), 2.00-1.41 (m, 9H), 0.86 (dt, J = 6.3, 3.1 Hz, 2H), 0.72 (dt, J = 6.7, 3.3 Hz, 2H). (the N—CH$_3$ on pyrazole is not observed due to water-suppression); hLPA$_1$ IC$_{50}$ = 341 nM. | Example 3 |
| 6 | 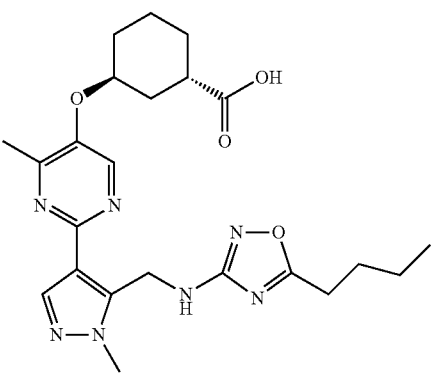<br>(1S,3S)-3-((2-(5-(((5-butyl-1,2,4-oxadiazol-3-yl)amino)methyl)-1-methyl-1H-pyrazol-4-yl)-4-methyl-pyrimidin-5-yl)oxy) cyclohexane-1-carboxylic acid, 2 TFA | LC-MS, [M + H]$^+$ = 470.4; $^1$H NMR (500 MHz, CD$_3$OD) δ 8.46 (s, 1H), 8.06 (s, 1H), 4.94-4.90 (m, 1H), 4.78 (s, 2H), 4.06 (s, 3H), 2.87-2.80 (m, 1H), 2.75 (t, J = 7.6 Hz, 2H), 2.57 (s, 3H), 2.16-2.08 (m, 1H), 2.06-1.91 (m, 3H), 1.83-1.64 (m, 6H), 1.40 (sxt, J = 7.4 Hz, 2H), 0.95 (t, J = 7.3 Hz, 3H); hLPA$_1$ IC$_{50}$ = 31 nM. | Example 4 |

TABLE 1-continued

| Ex # | Structure & Name | Analytical & Biological Data | Method |
|---|---|---|---|
| 7 | 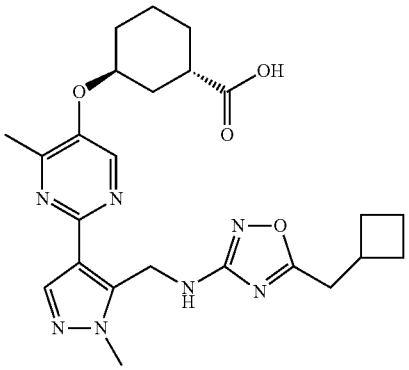<br>(1S,3S)-3-((2-(5-(((5-(cyclobutyl methyl)-1,2,4-oxadiazol-3-yl)amino)methyl)-1-methyl-1H-pyrazol-4-yl)-4-methylpyrimidin-5-yl)oxy)cyclo-hexane-1-carboxylic acid, 2 TFA | LC-MS, [M + H]$^+$ = 482.1; $^1$H NMR (500 MHz, DMSO-$d_6$) δ 8.34 (s, 1H), 7.89 (s, 1H), 4.78 (br s, 1H), 4.68 (br d, J = 4.6 Hz, 2H), 4.14-4.03 (m, 4H), 2.75 (d, J = 7.6 Hz, 2H), 2.65-2.58 (m, 1H), 2.37 (s, 3H), 2.02-1.92 (m, 3H), 1.85-1.70 (m, 5H), 1.68-1.41 (m, 6H); hLPA$_1$ IC$_{50}$ = 9 nM. | Example 4 |
| 8 | 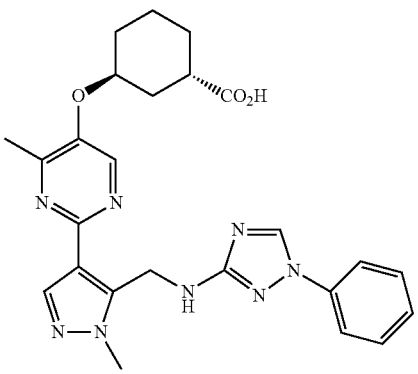<br>(1S,3S)-3-((4-methyl-2-(1-methyl-5-(((1-phenyl-1H-1,2,4-triazol-3-yl)amino)methyl)-1H-pyrazol-4-yl)pyrimidin-5-yl)oxy)cyclohexane-1-carboxylic acid | LCMS, [M + H]$^+$ = 489.2; $^1$H NMR (400 MHz, CDCl$_3$) δ 8.64 (s, 1H), 8.57 (s, 1H), 8.30 (s, 1H), 7.60-7.44 (m, 5H), 4.90 (s, 2H), 4.78 (br s, 1H), 4.22 (s, 3H), 2.93-2.83 (m, 1H), 2.65 (s, 3H), 2.20-1.59 (m, 8H); hLPA$_1$ IC$_{50}$ = 91 nM. | Example 1 |
| 10 | 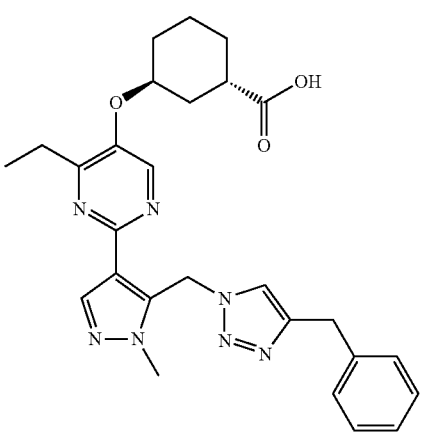<br>(1S,3S)-3-[(2-{5-[(4-benzyl-1H-1,2,3-triazol-1-yl)methyl]-1-methyl-1H-pyrazol-4-yl}-4-ethylpyrimidin-5-yl)oxy]cyclohexane-1-carboxylic acid | LCMS, [M + H]+ = 502.3; $^1$H NMR (500 MHz, DMSO-$d_6$) δ 8.45 (s, 1H), 7.98 (s, 1H), 7.81 (s, 1H), 7.28-7.21 (m, 3H), 7.20-7.15 (m, 2H), 6.16 (s, 2H), 4.85 (br s, 1H), 3.95-3.92 (m, 2H), 3.92-3.89 (m, 3H), 2.75 (q, J = 7.3 Hz, 2H), 2.69-2.59 (m, 1H), 2.02 (br d, J = 13.1 Hz, 1H), 1.83 (br d, J = 13.1 Hz, 4H), 1.68-1.47 (m, 4H), 1.15 (t, J = 7.5 Hz, 3H); hLPA$_1$ IC$_{50}$ = 26 nM. | Example 9 |

TABLE 1-continued

| Ex # | Structure & Name | Analytical & Biological Data | Method |
|---|---|---|---|
| 11 | (1S,3S)-3-[(2-{5-[(4-butyl-1H-1,2,3-triazol-1-yl)methyl]-1-methyl-1H-pyrazol-4-yl}-4-ethylpyrimidin-5-yl)oxy]cyclohexane-1-carboxylic acid | LCMS, [M + H]+ = 468.4; $^1$H NMR (500 MHz, DMSO-$d_6$) δ 8.48 (s, 1H), 7.98 (s, 1H), 7.79 (s, 1H), 6.16 (s, 2H), 4.83 (br s, 1H), 3.90 (s, 3H), 2.83-2.76 (m, 2H), 2.58-2.52 (m, 2H), 1.95 (br s, 1H), 1.85 (br s, 1H), 1.80 (br s, 2H), 1.68-1.56 (m, 3H), 1.56-1.39 (m, 4H), 1.29-1.13 (m, 5H), 0.83 (t, J = 7.3 Hz, 3H); hLPA$_1$ IC$_{50}$ = 399 nM. | Example 9 |
| 12 | (1S,3S)-3-{[2-(5-{[4-(cyclopropylmethyl)-1H-1,2,3-triazol-1-yl]methyl}-1-methyl-1H-pyrazol-4-yl)-4-ethylpyrimidin-5-yl]oxy}cyclo-hexane-1-carboxylic acid | LCMS, [M + H]+ = 466.2; $^1$H NMR (500 MHz, DMSO-$d_6$) δ 8.48 (s, 1H), 7.98 (s, 1H), 7.87 (s, 1H), 6.16 (s, 2H), 4.82 (br s, 1H), 3.95-3.89 (m, 3H), 2.79 (q, J = 7.6 Hz, 2H), 1.91 (br s, 1H), 1.83 (br s, 1H), 1.76 (br s, 2H), 1.63 (br d, J = 11.6 Hz, 1H), 1.57 (br s, 1H), 1.52 (br s, 2H), 1.20 (t, J = 7.5 Hz, 3H), 0.91 (br s, 1H), 0.37 (br d, J = 7.0 Hz, 2H), 0.09 (br d, J = 4.3 Hz, 2H); 3 missing protons due to water suppression; hLPA$_1$ IC$_{50}$ = 230 nM. | Example 9 |

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:
1. A compound selected from:
   (1S,3S)-3-((4-methyl-2-(1-methyl-5-(((2-phenyl-2H-1,2,3-triazol-4-yl)amino)methyl)-1H-pyrazol-4-yl)pyrimidin-5-yl)oxy)cyclohexane-1-carboxylic acid;
   (1S,3S)-3-((2-(5-(((3-isopropyl-1,2,4-thiadiazol-5-yl)amino)methyl)-1-methyl-1H-pyrazol-4-yl)-4-methylpyrimidin-5-yl)oxy)cyclohexane-1-carboxylic acid;
   (1S,3S)-3-((4-methyl-2-(1-methyl-5-((3-propyl-1,2,4-thiadiazol-5-yl)amino)-1H-pyrazol-4-yl)pyrimidin-5-yl)oxy)cyclohexane-1-carboxylic acid;
   (1S,3S)-3-((2-(5-(((5-isopentyl-1,2,4-oxadiazol-3-yl)amino)methyl)-1-methyl-1H-pyrazol-4-yl)-4-methylpyrimidin-5-yl)oxy)cyclohexane-1-carboxylic acid;
   (1S,3S)-3-((2-(5-((4-(cyclopropylmethyl)-1H-1,2,3-triazol-1-yl)methyl)-1-methyl-1H-pyrazol-4-yl)-4-methylpyrimidin-5-yl)oxy)cyclohexane-1-carboxylic acid;
   (1S,3S)-3-((2-(5-((3-cyclopropyl-1,2,4-thiadiazol-5-yl)amino)-1-methyl-1H-pyrazol-4-yl)-4-methylpyrimidin-5-yl)oxy) cyclohexane-1-carboxylic acid;
   (1S,3S)-3-((2-(5-(((5-butyl-1,2,4-oxadiazol-3-yl)amino)methyl)-1-methyl-1H-pyrazol-4-yl)-4-methyl-pyrimidin-5-yl)oxy) cyclohexane-1-carboxylic acid;
   (1S,3S)-3-((2-(5-(((5-(cyclobutyl methyl)-1,2,4-oxadiazol-3-yl)amino) methyl)-1-methyl-1H-pyrazol-4-yl)-4-methylpyrimidin-5-yl)oxy)cyclo-hexane-1-carboxylic acid;
   (1S,3S)-3-((4-methyl-2-(1-methyl-5-(((1-phenyl-1H-1,2,4-triazol-3-yl) amino)methyl)-1H-pyrazol-4-yl) pyrimidin-5-yl)oxy)cyclohexane-1-carboxylic acid;

(1S,3S)-3-[(2-{5-[(4-benzyl-1H-1,2,3-triazol-1-yl)methyl]-1-methyl-1H-pyrazol-4-yl}-4-ethylpyrimidin-5-yl)oxy]cyclohexane-1-carboxylic acid;

(1S,3S)-3-[(2-{5-[(4-butyl-1H-1,2,3-triazol-1-yl)methyl]-1-methyl-1H-pyrazol-4-yl}-4-ethylpyrimidin-5-yl) oxy]cyclohexane-1-carboxylic acid;

(1S,3S)-3-{[2-(5-{[4-(cyclopropyl methyl)-1H-1,2,3-triazol-1-yl] methyl}-1-methyl-1H-pyrazol-4-yl)-4-ethylpyrimidin-5-yl]oxy}cyclo-hexane-1-carboxylic acid;

or a pharmaceutically acceptable salt.

2. A pharmaceutical composition comprising one or more compounds according to claim 1, or a pharmaceutically acceptable salt; and a pharmaceutically acceptable carrier or diluent.

3. A method of treating idiopathic pulmonary fibrosis (IPF), in a patient having IPF, comprising administering a therapeutically effective amount of a compound or a pharmaceutically acceptable salt thereof according to claim 1.

\* \* \* \* \*